United States Patent
De Silva et al.

(10) Patent No.: US 9,028,817 B2
(45) Date of Patent: May 12, 2015

(54) STABLE ANTI-TNFR1 POLYPEPTIDES, ANTIBODY VARIABLE DOMAINS AND ANTAGONISTS

(75) Inventors: Inusha De Silva, Cambridge (GB); Armin Sepp, Cambridge (GB); Adriaan Allart Stoop, Cambridge (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 13/504,525

(22) PCT Filed: Oct. 25, 2010

(86) PCT No.: PCT/EP2010/066046
§ 371 (c)(1),
(2), (4) Date: Apr. 27, 2012

(87) PCT Pub. No.: WO2011/051217
PCT Pub. Date: May 5, 2011

(65) Prior Publication Data
US 2012/0213787 A1     Aug. 23, 2012

Related U.S. Application Data

(60) Provisional application No. 61/225,235, filed on Oct. 27, 2009.

(51) Int. Cl.
*A61K 38/00*    (2006.01)
*C12Q 1/68*    (2006.01)
*C12Q 1/70*    (2006.01)

(52) U.S. Cl.
CPC ............. *C12Q 1/6851* (2013.01); *C12Q 1/70* (2013.01)

(58) Field of Classification Search
None
See application file for complete search history.

(56) References Cited

U.S. PATENT DOCUMENTS

| | | | |
|---|---|---|---|
| 2011/0301335 A1* | 12/2011 | Duffield et al. | 530/387.3 |
| 2012/0107330 A1* | 5/2012 | Stoop | 424/174.1 |

FOREIGN PATENT DOCUMENTS

| WO | WO 9501997 A1 * | 1/1995 |
|---|---|---|
| WO | WO 2006/038027 A2 | 4/2006 |
| WO | WO 2008/096158 A2 | 8/2008 |
| WO | WO 2008/149143 A2 | 12/2008 |
| WO | WO 2010/094720 A2 | 8/2010 |
| WO | WO 2010/094723 A2 | 8/2010 |

* cited by examiner

*Primary Examiner* — Sean Aeder
*Assistant Examiner* — Julie Wu
(74) *Attorney, Agent, or Firm* — Robert H. Brink

(57) ABSTRACT

The invention relates to storage-stable anti-TNFR1 antibody single variable domains (dAbs), antagonists and multispecific ligands, as well as methods and uses of these. The anti-TNFR1 polypeptides, antibody single variable domains (dAbs), antagonists and multispecific ligands are useful for treating and/or preventing inflammatory disease, such as arthritis or COPD, as well as for pulmonary administration, oral administration, delivery to the lung and delivery to the GI tract of a patient.

8 Claims, 6 Drawing Sheets

Figure 1C:
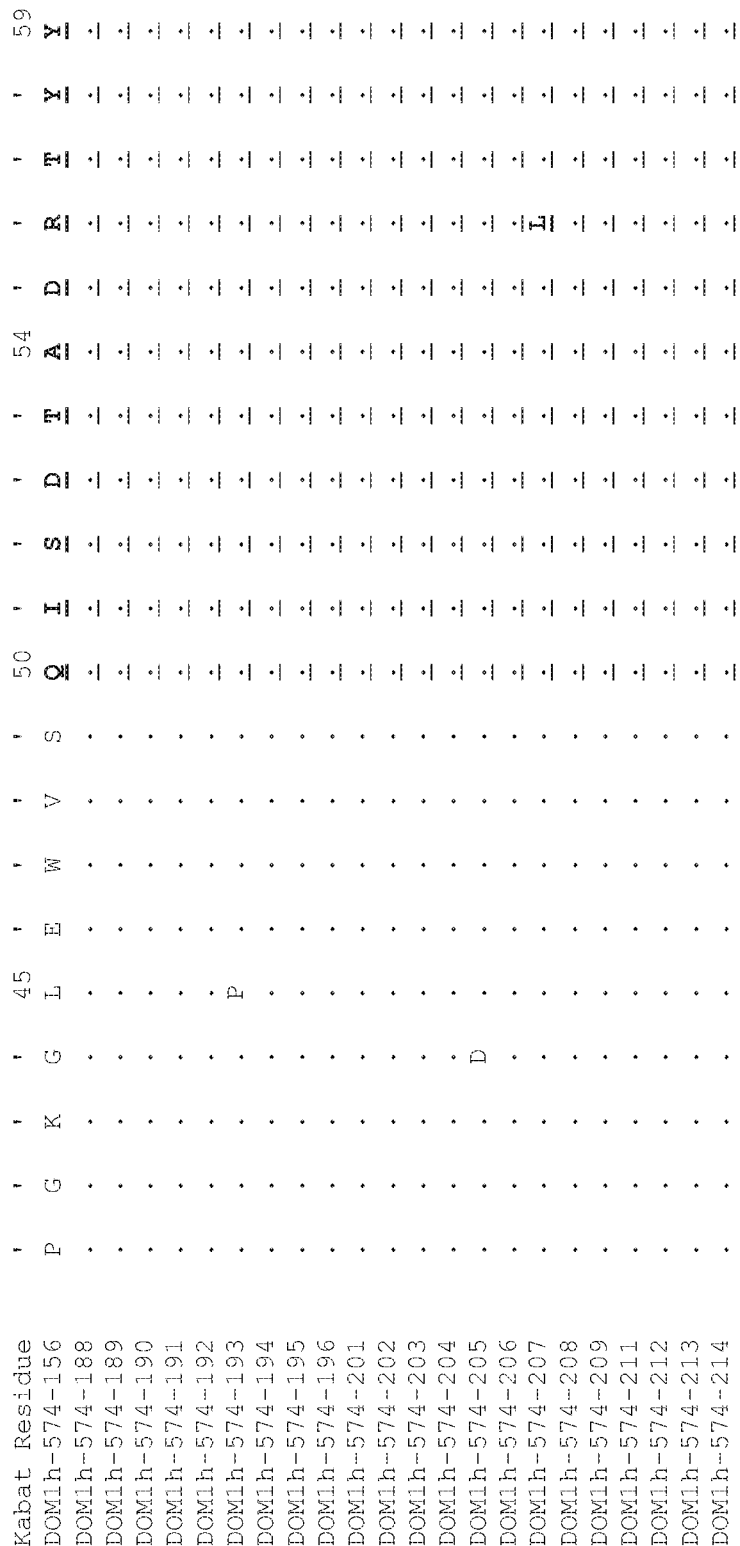

| Kabat Residue | 1 E | 2 V | 3 Q | 4 L | 5 L | 6 E | 7 S | 8 G | 9 G | 10 G | 11 L | 12 V | 13 Q | 14 P | 15 G | 16 G | 17 S | 18 L | 19 R | 20 L |
|---|---|---|---|---|---|---|---|---|---|---|---|---|---|---|---|---|---|---|---|---|
| DOM1h-574-156 | . | . | . | . | . | . | . | . | . | . | . | . | . | . | . | . | . | . | . | . |
| DOM1h-574-188 | . | . | . | . | . | . | . | . | . | . | . | . | . | . | . | . | . | . | . | . |
| DOM1h-574-189 | . | . | . | . | . | . | . | . | . | . | . | . | . | . | . | . | . | . | . | . |
| DOM1h-574-190 | . | . | . | . | . | . | . | . | . | . | . | . | . | . | . | . | . | . | . | . |
| DOM1h-574-191 | . | . | . | . | . | . | . | . | . | . | . | . | . | . | . | . | . | . | . | . |
| DOM1h-574-192 | . | . | . | . | . | . | . | . | . | . | . | . | . | . | . | . | . | . | . | . |
| DOM1h-574-193 | . | . | . | . | . | . | . | . | . | . | . | . | . | . | . | . | . | . | . | . |
| DOM1h-574-194 | . | . | . | . | . | . | . | . | . | . | . | . | . | . | . | . | . | . | . | . |
| DOM1h-574-195 | . | . | . | . | . | . | . | . | . | . | . | . | . | . | . | . | . | . | . | . |
| DOM1h-574-196 | . | . | . | . | . | . | . | . | . | . | . | . | . | . | . | . | . | . | . | . |
| DOM1h-574-201 | . | . | . | . | . | . | . | . | . | . | . | . | . | . | . | . | . | . | . | . |
| DOM1h-574-202 | . | . | . | . | . | . | . | . | . | . | . | . | . | . | . | . | . | . | . | . |
| DOM1h-574-203 | . | . | . | . | . | . | . | . | . | . | . | . | . | . | . | . | . | . | . | . |
| DOM1h-574-204 | . | . | . | . | . | . | . | . | . | . | . | . | . | . | . | . | . | . | . | . |
| DOM1h-574-205 | . | . | . | . | . | D | . | . | . | . | . | . | . | . | . | . | . | . | . | . |
| DOM1h-574-206 | . | . | . | . | . | . | . | . | . | . | . | . | . | . | . | . | . | . | . | . |
| DOM1h-574-207 | . | . | . | . | . | . | . | . | . | . | M | . | . | . | . | . | . | . | . | . |
| DOM1h-574-208 | . | . | . | . | . | . | . | . | . | . | . | . | . | . | . | . | . | . | . | . |
| DOM1h-574-209 | . | . | . | . | . | . | . | . | . | . | . | . | . | . | . | . | . | . | . | . |
| DOM1h-574-211 | . | . | . | . | . | . | . | . | . | . | . | . | . | . | . | . | . | . | . | . |
| DOM1h-574-212 | . | . | . | . | . | . | . | . | . | . | . | . | . | . | . | . | . | . | . | . |
| DOM1h-574-213 | . | . | . | . | . | . | . | . | . | . | . | . | . | . | . | . | . | . | . | . |
| DOM1h-574-214 | . | . | . | . | . | . | . | . | . | . | . | . | . | . | . | . | . | . | . | . |

FIGURE 1A

| Kabat Residue | S | C | A | A | S(25) | G | F | T | F | D(30) | K | Y | S | M | G(35) | W | V | R | Q | A(40) |
|---|---|---|---|---|---|---|---|---|---|---|---|---|---|---|---|---|---|---|---|---|
| DOM1h-574-156 | S | C | A | A | S | G | F | T | F | D | K | Y | S | M | G | W | V | R | Q | A |
| DOM1h-574-188 | . | . | . | . | . | . | . | . | . | . | . | . | . | . | . | . | . | . | . | . |
| DOM1h-574-189 | . | . | . | . | . | . | . | . | . | . | . | . | . | . | . | . | . | . | . | . |
| DOM1h-574-190 | . | . | . | . | . | . | . | . | . | S | . | . | . | . | . | . | . | . | . | . |
| DOM1h-574-191 | . | . | . | . | . | . | . | . | . | S | . | . | . | . | . | . | . | . | . | . |
| DOM1h-574-192 | . | . | . | . | . | . | . | . | . | D | . | . | . | . | . | . | . | . | . | . |
| DOM1h-574-193 | . | . | . | . | . | . | . | . | . | V | . | . | . | . | . | . | . | . | . | . |
| DOM1h-574-194 | . | . | . | . | . | . | . | . | . | . | . | N | . | . | . | . | . | . | . | . |
| DOM1h-574-195 | . | . | . | . | . | . | . | . | . | S | . | . | . | . | . | . | . | . | . | . |
| DOM1h-574-196 | . | . | . | . | . | . | . | . | . | D | . | . | . | . | . | . | . | . | . | . |
| DOM1h-574-201 | . | . | . | . | . | . | . | . | . | . | . | . | . | . | . | . | . | . | . | . |
| DOM1h-574-202 | . | . | . | . | . | . | . | . | . | . | . | . | . | . | . | . | . | . | . | . |
| DOM1h-574-203 | . | . | . | . | . | . | . | . | . | . | . | . | . | . | . | . | . | . | . | . |
| DOM1h-574-204 | . | . | . | . | . | . | . | . | . | D | . | . | . | . | . | . | . | . | . | . |
| DOM1h-574-205 | . | . | . | . | . | . | . | . | . | . | . | . | . | . | . | . | . | . | . | . |
| DOM1h-574-206 | . | . | . | . | . | . | . | . | . | S | . | . | . | . | . | . | . | . | . | . |
| DOM1h-574-207 | . | . | . | . | . | . | . | . | . | D | . | . | . | . | . | . | . | . | . | . |
| DOM1h-574-208 | . | . | . | . | . | . | . | . | . | . | . | . | . | . | . | . | . | . | . | . |
| DOM1h-574-209 | . | . | S | . | . | . | . | . | . | A | . | . | . | . | . | . | . | . | . | . |
| DOM1h-574-211 | . | . | . | . | . | . | . | . | . | S | . | . | . | . | . | . | . | . | . | . |
| DOM1h-574-212 | . | . | . | . | . | . | . | . | . | D | . | . | . | . | . | . | . | . | . | . |
| DOM1h-574-213 | . | . | . | . | . | . | . | . | . | S | . | . | . | . | . | . | I | . | . | . |
| DOM1h-574-214 | . | . | . | . | . | . | . | . | . | . | . | . | . | . | . | . | . | . | . | . |

| Kabat Residue | G | R | W | V | P | F | E | Y | W | G | Q | G | T | L | V | T | V | S | S |
|---|---|---|---|---|---|---|---|---|---|---|---|---|---|---|---|---|---|---|---|
| | | | | | 100a' | | | | | 104 | | | | | 109 | | | | |
| DOM1h-574-156 | G | R | W | V | P | F | E | Y | W | G | Q | G | T | L | V | T | V | S | S |
| DOM1h-574-188 | . | . | . | . | . | . | . | . | . | . | . | . | . | . | . | . | . | . | . |
| DOM1h-574-189 | . | . | . | E | . | . | . | . | . | . | . | . | . | . | . | . | . | . | . |
| DOM1h-574-190 | . | . | . | A | . | . | . | . | . | . | . | . | . | . | . | . | . | . | . |
| DOM1h-574-191 | . | . | . | . | . | . | . | N | . | . | . | . | . | . | . | . | . | . | . |
| DOM1h-574-192 | . | . | . | E | . | . | . | . | . | . | . | . | . | . | . | . | . | . | . |
| DOM1h-574-193 | . | . | . | . | . | . | . | . | . | . | . | . | . | . | . | . | . | . | . |
| DOM1h-574-194 | . | . | . | E | . | . | . | . | . | . | . | . | . | . | . | . | . | . | . |
| DOM1h-574-195 | . | . | . | E | . | . | . | . | . | . | . | . | . | . | . | . | . | . | . |
| DOM1h-574-196 | . | . | . | . | . | . | . | . | . | . | . | . | . | . | . | . | . | . | . |
| DOM1h-574-201 | . | . | . | A | . | . | . | . | . | . | . | . | . | . | . | . | . | . | . |
| DOM1h-574-202 | . | . | . | A | . | . | . | . | . | . | . | . | . | . | . | . | . | . | . |
| DOM1h-574-203 | . | . | . | A | . | . | . | . | . | . | . | . | . | . | . | . | . | . | . |
| DOM1h-574-204 | . | Q | . | E | . | Y | . | . | . | . | H | . | . | . | . | . | . | . | . |
| DOM1h-574-205 | . | . | . | A | . | . | . | N | . | . | . | . | . | . | . | . | . | . | . |
| DOM1h-574-206 | . | . | . | A | . | . | . | . | . | . | . | . | . | . | . | . | . | . | . |
| DOM1h-574-207 | . | . | . | . | . | . | . | . | . | . | . | . | . | . | . | . | . | . | . |
| DOM1h-574-208 | . | Q | . | E | . | Y | . | . | . | . | . | . | . | . | . | . | . | . | . |
| DOM1h-574-209 | . | . | . | . | . | . | . | . | . | . | . | . | . | . | . | . | . | . | . |
| DOM1h-574-211 | . | . | . | . | . | . | . | . | . | . | . | . | . | . | . | . | . | R | A |
| DOM1h-574-212 | . | . | . | . | . | . | . | . | . | . | . | . | . | . | . | . | . | . | . |
| DOM1h-574-213 | . | . | . | . | . | . | . | . | . | . | . | . | . | . | . | . | . | . | . |
| DOM1h-574-214 | . | . | . | . | . | . | . | . | . | . | . | . | . | . | . | . | . | . | . |

SEQUENCE LISTING

<160> NUMBER OF SEQ ID NOS: 76

<210> SEQ ID NO 1
<211> LENGTH: 21
<212> TYPE: DNA
<213> ORGANISM: Artificial Sequence
<220> FEATURE:
<223> OTHER INFORMATION: PCR Primer

<400> SEQUENCE: 1
caggaaacag ctatgaccat g                                         21

<210> SEQ ID NO 2
<211> LENGTH: 20
<212> TYPE: DNA
<213> ORGANISM: Artificial Sequence
<220> FEATURE:
<223> OTHER INFORMATION: PCR Primer

<400> SEQUENCE: 2
ttcaggctgc gcaactgttg                                           20

<210> SEQ ID NO 3
<211> LENGTH: 22
<212> TYPE: DNA
<213> ORGANISM: Artificial Sequence
<220> FEATURE:
<223> OTHER INFORMATION: PCR Primer

<400> SEQUENCE: 3
cgccaagctt gcatgcaaat tc                                        22

```
<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
ttgtaaaacg acggccagtg                                                    20

<210> SEQ ID NO 5
<211> LENGTH: 19
<212> TYPE: DNA
<213> ORGANISM: Artificial Sequence
<220> FEATURE:
<223> OTHER INFORMATION: PCR Primer

<400> SEQUENCE: 5
cttaaacagc ttgataccg                                                     19

<210> SEQ ID NO 6
<211> LENGTH: 18
<212> TYPE: DNA
<213> ORGANISM: Artificial Sequence
<220> FEATURE:
<223> OTHER INFORMATION: PCR Primer

<400> SEQUENCE: 6
gacagccctc atagttag                                                      18

<210> SEQ ID NO 7
<211> LENGTH: 36
<212> TYPE: DNA
<213> ORGANISM: Artificial Sequence
<220> FEATURE:
<223> OTHER INFORMATION: PCR Primer

<400> SEQUENCE: 7
ttcttttgct agcgctcgag acggtgacca gggttc                                  36

<210> SEQ ID NO 8
<211> LENGTH: 102
<212> TYPE: DNA
<213> ORGANISM: Artificial Sequence
<220> FEATURE:
<223> OTHER INFORMATION: PCR Primer

<400> SEQUENCE: 8
ggaattccat atgaaatacc tgctgccgac cgctgctgct ggtctgctgc tcctcgctgc        60
ccagccggcg atggccgagg tgcagctgtt ggagtctggg gg                          102

<210> SEQ ID NO 9
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 9
gaggtgcagc tgttggagtc tgggggaggc ttggtacagc ctggggggtc cctgcgtctc        60
tcctgtgcag cctccggatt cacctttgat aagtattcaa tggggtgggt ccgccaggct       120
ccagggaagg gtctagagtg ggtctcacag atttcggata ctgctgatcg tacatactac       180
```

```
gcacactccg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactggggt cagggaaccc tggtcaccgt ctcgagc       357
```

<210> SEQ ID NO 10
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 10

```
gaggtgcagc tgttggagtc tgggggaggc ttggtacagc ctgggggtc cctgcgtctc     60 tcctgtgcag cctccggatt cacctttttc aagtattcga tggggtgggt ccgccaggct   120
ccagggaagg gtctagagtg ggtctcacag atttcggata ctgctgatcg tacatactac   180
gcacactccg tgaagggccg gttcaccatc tcccgcgaca attccaagaa cacgctgtat   240
ctgcaaatga acagcctgcg tgctgaggac accgcggttt attactgtgc ggtatatact   300
gggcgttggg agccttttga gtactggggt cagggaaccc tggtcaccgt ctcgagc     357
```

<210> SEQ ID NO 11
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 11

```
gaggtgcagc tgttggagtc tgggggaggc ttggtacagc ctgggggtc cctgcgtctc     60 tcctgtgcag cctccggatt cacctttttc aagtattcga tggggtggat ccgccaggct   120
ccaggtaagg gtctagagtg ggtctcacag atttcggata ctgctgatcg tacatactac   180
gcacactccg tgaagggccg gttcaccatc tcccgcgaca attccaagaa cacgctgtat   240
ctgcaaatga acagcctgcg tgccgaggac accgcggtat attactgtgc ggtatatacg   300
ggtcggtggg cgccttttga gtactggggt cagggaaccc tggtcaccgt ctcgagc     357
```

<210> SEQ ID NO 12
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 12

```
gaggtgcagc tgttggagtc tgggggaggc ttggtacagc ctgggggtc cctgcgtctc     60 tcctgtgcag cctccggatt cacatttcc aagtattcga tggggtgggt ccgccaggct    120
ccagggaagg gtctagagtg ggtctcacag atttcggata ctgctgatcg tacatactac   180
gcacactccg tgaagggccg gttcaccatc tcccgcgaca attccaagaa cacgctgtat   240
ctgcaaatga acagcctgcg tgctgaggac accgcggtat attactgtgc gatatatact   300
gggcgttggg tgccttttga gtactggggt cagggaaccc tggtcaccgt ctcgagc     357
```

<210> SEQ ID NO 13
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 13

```
gaggtgcagc tgttggagtc tgggggaggc ttggtacagc ctgggggtc cctgcgtctc      60
tcctgtgcag cctccggatt cacctttttcc aagtattcga tggggtgggt ccgccaggct    120
ccagggaagg gtctagagtg gtctcacag atttcggata ctgctgatcg tacatactac     180
gcacactccg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gaactggggt cagggaaccc tggtcaccgt ctcgagc       357
```

<210> SEQ ID NO 14
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 14

```
gaggtgcagc tgttggagtc tgggggaggc ttggtacagc ctgggggtc cctccgtctc      60
tcctgtgcag cctccggatt cacctttgat aagtattcga tggggtgggt ccgccaggct    120
ccagggaagg gtccagagtg gtctcacag atttcggata ctgctgatcg tacatactac     180
gcacactccg tgaagggccg gttcaccaac tcccgcgaca attccaagaa cacgctgtat    240
ctgcaaatga acagcctgcg tgctgaggac accgcggtat attactgtgc gatatatact    300
gggcgttggg agccttttga gtactggggt cagggaaccc tggtcaccgt ctcgagc       357
```

<210> SEQ ID NO 15
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 15

```
gaggtgcagc tgttggagtc tgggggaggc ttggtacagc ctgggggtc cctgcgtctc      60
tcctgtgcag cctccggatt cacctttgtt aagtattcga tggggtgggt ccgccaggct    120
ccagggaagg gtctagagtg gtctcacag atttcggata ctgctgatcg tacatactac     180
gcacacgcgg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccatttga gtactggggt cagggaaccc tggtcaccgt ctcgagc       357
```

<210> SEQ ID NO 16
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 16

```
gaggtgcagc tgttggagtc tgggggaggc ttggtacagc ctgggggtc cctgcgtctc      60
tcctgtgcag cctccggatt cacctttttc aagtattcga tggggtgggt ccgccaggct    120
cctgggaagg gtctagagtg gtctcacag atttcggata ctgctgatcg tacatactac     180
gcacactccg tgaagggccg gttcaccatc tcccgcgaca attccaagaa cacgctgtat    240
ctgcaaatga acagcctgcg tgctgaggac accgcggtat attactgtgc gatatatact    300
```

```
gggcgctggg agccttttga gtactgggga cagggaaccc tggtcaccgt ctcgagc      357
```

```
<210> SEQ ID NO 17
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 17
gaggtgcagc tgttggagtc tgggggaggc ttggtacagc ctgggggttc cctgcgtctc      60
tcctgtgcag cctccggatt cacctttttcc aagtattcga tggggtgggt ccgccaggct     120
ccagggaagg gtctagagtg ggtctcacag atttcggata ctgctgatcg tacatactac     180
gcacactccg tgaagggccg gttcaccatc tcccgcgaca attccaagaa cacgctgtat     240
ctgcaaatga acagcctgcg tgctgaggac accgcggtat attactgtgc gatatatact     300
gggcgttggg agccttttga gtactggggt cagggaaccc tggtcaccgt ctcgagc      357
```

```
<210> SEQ ID NO 18
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 18
gaggtgcagc tgttggagtc tgggggaggc ttggtacagc ctgggggttc cctgcgtctc      60
tcctgtgcag cctccggatt caccttttgat aagaattcga tggggtgggt ccgccaggct    120
ccagggaagg gtctagagtg ggtctcacag atatcggata cagctgatcg tacatactac     180
gcacactcac tgaagggccg gttcaccatc tcccgcgaca attccaagaa cacgctgtat     240
ctgcaaatga acagcctgcg tgctgaggac accgcggtat attactgtgc gatatatact     300
gggcgttggg tgccttttga gtactggggt cagggaaccc tggtcaccgt ctcgagc      357
```

```
<210> SEQ ID NO 19
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 19
gaggtgcagc tgttggagtc tgggggaggc ttggtacagc ctgggggttc cctgcgtctc      60
tcctgtgcag cctccggatt cacctttttc aagtattcga tggggtgggt ccgccaggct     120
ccagggaagg gtctagagtg gtatcacag atatcggata ctgctgatcg tacatactac      180
gcacactccg tgaagggccg gttcaccatc tcccgcgaca attccaagaa cacgctgtat     240
ctgcaaatga acagcctgcg tgccgaggac accgcggtat attactgtgc ggtatatacg     300
ggtcggtggg cgccttttga gtactggggt cagggaaccc tggtcaccgt ctcgagc      357
```

```
<210> SEQ ID NO 20
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 20
gaggtgcagc tgttggagtc tgggggaggc ttggtacagc ctgggggttc cctgcgtctc      60
```

```
tcctgtgcag cctccggatt cacctttttc aagtattcga tggggtgggt ccgccaggct    120
ccagggaagg gtctagagtg ggtctcacag atttcggata ctgctgatcg tacatactac   180
gcacactccg tgaagggccg gttcaccatc tcccgcgacg attccaagaa cacgctgtat   240
ctgcaaatga acagcctgcg cgccgaggac accgcggtat attactgcgc gatatatacg   300
ggtcggtggg cgccttttga gtactggggt cagggaaccc tggtcaccgt ctcgagc     357
```

<210> SEQ ID NO 21
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 21

```
gaggtgcagc tgttggagtc tgggggaggc ttggtacagc ctgggggtc cctgcgtctc    60 tcctgtgcag cctccggatt cacctttttc aagtattcga tggggtgggt ccgccaggct   120
ccagggaagg gtctagagtg ggtctcacag atttcggata ctgctgatcg tacatactac   180
gcacactccg tgaagggccg gttcaccatc tcccgcgaca attccaagaa cacgctgtat   240
ctgcaaatga acagcctgcg tgtcgaggac accgcggtat attactgtgc gatatatacg   300
ggtcagtggg cgccttatga gtactggggt cagggaaccc tggtcaccgt tcgagcg     357
```

<210> SEQ ID NO 22
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 22

```
gaggtgcagc tgttggagtc tgggggaggc ttggtacagc ctgggggtc cctgcgtctc    60 tcctgtgcag cctccggatt caccttgat aagtattcga tggggtgggt ccgccaggct   120
ccagggaagg atctagagtg ggtctcacag atttcggata ctgctgaccg tacatactac   180
gcacactccg tgaagggccg gttcaccatc tcccgcgaca attccaagaa cacgctgtat   240
ctgcaaatga acagtctgcg tgctgaggac accgcggtat attactgtgc gatatatact   300
gggcgttggg tgccttttga gaactggggt cacggaaccc tggtcaccgt ctcgagc     357
```

<210> SEQ ID NO 23
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 23

```
gaggtgcagt tgttggattc tgggggaggc ttggtacagc ctgggggtc cctgcgtctc    60 tcctgtgcag cctccggatt cacctttttc aagtattcga tggggtgggt ccgccaggct   120
ccagggaagg gtctagagtg ggtctcacag atttcggata ctgctgatcg tacatactac   180
tcaccctccg tgaagggccg gttcaccatc tcccgcgaca attccgggaa cacgctgaat   240
ctgcaaatga ccccctgcg tgctgaggac accgcggtat attactgtgc gatatatact   300
gggcgttggg agccttttga gtactggggt cagggaaccc tggtcaccgt ctcgagc     357
```

<210> SEQ ID NO 24

<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 24

```
gaggtgcagc tgttggagtc tgggggaggc atggtacagc cggggggtc cctgcgtctc      60
tcctgtgcat cctccggatt caccttttcc aagtattcga tggggtgggt ccgccaggct    120
ccagggaaag gtctagagtg gtctcacag atttccgata ctgctgatct tacatactac    180
gcacactccg tgaagggccg gttcaccatc tcccgcgaca attccaagaa cacgctgtat    240
ctgcaaatga acagcctgcg tgccgaggac accgcggaat attactgtgc gatatatacg    300
ggtcggtggg cgccttttga gtactggggt caggaaccc tggtcaccgt ctcgagc        357
```

<210> SEQ ID NO 25
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 25

```
gaggtgcagc tgttggagtc tgggggaggc ttggtacagc ctggggggtc cctgcgtctc     60
tcctgtgcag cctccggatt cacctttgat aagtattcga tggggtgggt ccgccaggct    120
ccagggaagg gtctagagtg gtctcacag atttcggata ctgctgatcg tacatactac    180
gcacacgcg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactggggt caggaaccc tggtcaccgt ctcgagc        357
```

<210> SEQ ID NO 26
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 26

```
gaggtgcagc tgttggagtc tgggggaggc ttggtacagc ctggggggtc cctgcgtctc     60
tcctgtgcag cctccggatt cacctttttc aagtattcga tgggtgggt ccgccaggct    120
ccagggaagg gtctagagtg gtctcacag atttcggata ctgctgatcg tacatactac    180
gcacactccg tgaagggccg gttcaccatc tcccgcgaca attccaagaa cacgctgtat    240
ctgcaaatga acagcctgcg tgtcgaggac accgcggtat attactgtgc gatatatacg    300
ggtcagtggg cgccttatga gtactggggt caggaaccc tggtcaccgt ctcgagc        357
```

<210> SEQ ID NO 27
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 27

```
gaggtgcagc tgttggagtc tgggggaggc ttggtacagc ctggggggtc cctgcgtctc     60
tcctgtgcag cctccggatt cacctttgct aagtattcga tggggtgggt ccgccaggct    120
ccagggaagg gtctagagtg gtctcacag atttcggata ctgctgatcg tacatactac    180
```

```
gcacacgcgg tgaagggccg gttcaccatc tcccgcgaca attccaagaa cacgctgtat      240
ctgcaaatga acagcctgcg tgctgaggac accgcggtat attactgtgc gatatatact      300
gggcgttggg tgccttttga gtactggggt cagggaaccc tggtcaccgt ctcgagc         357
```

<210> SEQ ID NO 28
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 28

```
gaggtgcagc tgttggagtc tgggggaggc ttggtacagc ctgggggggtc cctgcgtctc      60 tcctgtgcag cctccggatt caccttttcc aagtattcga tggggtgggt ccgccaggct     120
ccagggaagg gtctagagtg ggtctcacag atttcggata ctgctgatcg tacatactac     180
gcacactccg tgaagggccg gttcaccatc tcccgcgaca attccaagaa cacactgtac     240
ctgcaaatga acagcctgcg tgctgaggac accgcggtat attactgtgc gatatatact     300
gggcgttggg tgccttttga gtactggggt cagggaaccc tggtcaccgt ctcgagc        357
```

<210> SEQ ID NO 29
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 29

```
gaggtgcagc tgttggagtc tgggggaggc ttggtacagc ctgggggggtc cctccgtctc      60 tcctgtgcag cctccggatt cacctttgat aagtattcga tggggtgggt ccgccaggct     120
ccagggaagg gtctagagtg ggtctcacag atttcggata ctgctgatcg tacatactac     180
gcacactccg taaagggccg gttcaccatc acccgcgaca attccaagaa cacgctgtat     240
ctgcaaatga acagcctgcg tgctgaggac accgcggtat attactgtgc gatatatact     300
gggcgttggg agccttttga gtactggggt cagggaaccc tggtcaccgt ctcgagc        357
```

<210> SEQ ID NO 30
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 30

```
gaggtgcagc tgttggagtc tgggggaggc ttggtacagc ccggggggtc cctgcgtctc      60
tcctgtgcag cctccggatt caccttttcc aagtattcga tggggtgggt ccgccaggct     120
ccagggaagg gtctagagtg ggtctcacag atttcggata ctgctgatcg tacatactac     180
gcagactccg tgaagggccg gttcaccatc tcccgcgaca attccaagaa cacgctgtat     240
ctgcaaatga acagcctgcg tgccgaggac accgcggtat attactgtgc gatatacact     300
gggcgttggg tgccttttga gtactggggt cagggaaccc tggtcaccgt ctcgagc        357
```

<210> SEQ ID NO 31
<211> LENGTH: 690
<212> TYPE: DNA
<213> ORGANISM: Artificial Sequence
<220> FEATURE:

<223> OTHER INFORMATION: Derived from a human germline sequence

<400> SEQUENCE: 31

```
gaggtgcagc tgttggagtc tgggggaggc ttggtacagc ctggggggtc cctgcgtctc      60
tcctgtgcag cctccggatt caccttttcc aagtattcga tggggtgggt ccgccaggct     120
ccagggaagg gtctagagtg ggtctcacag atttcggata ctgctgatcg tacatactac     180
gcacactccg tgaagggccg gttcaccatc tcccgcgaca attccaagaa cacgctgtat     240
ctgcaaatga acagcctgcg tgctgaggac accgcggtat attactgtgc gatatatact     300
gggcgttggg agccttttga gtactggggt cagggaaccc tggtcaccgt ctcgagcgct     360
agcaccgaca tccagatgac ccagtctcca tcctccctgt ctgcatctgt aggagaccgt     420
gtcaccatca cttgccgggc aagtcgtccg attgggacga cgttaagttg gtaccagcag     480
aaaccaggga aagcccctaa gctcctgatc ctttggaatt cccgtttgca aagtggggtc     540
ccatcacgtt tcagtggcag tggatctggg acagatttca ctctcaccat cagcagtctg     600
caacctgaag attttgctac gtactactgt gcgcaggctg ggacgcatcc tacgacgttc     660
ggccaaggga ccaaggtgga aatcaaacgg                                      690
```

<210> SEQ ID NO 32
<211> LENGTH: 690
<212> TYPE: DNA
<213> ORGANISM: Artificial Sequence
<220> FEATURE:
<223> OTHER INFORMATION: Derived from a human germline sequence

<400> SEQUENCE: 32

```
gaggtgcagc tgttggagtc tgggggaggc ttggtacagc ctggggggtc cctgcgtctc      60
tcctgtgcag cctccggatt cacctttgat aagtattcga tggggtgggt ccgccaggct     120
ccagggaagg gtctagagtg ggtctcacag atttcggata ctgctgatcg tacatactac     180
gcacacgcgg tgaagggccg gttcaccatc tcccgcgaca attccaagaa cacgctgtat     240
ctgcaaatga acagcctgcg tgctgaggac accgcggtat attactgtgc gatatatact     300
gggcgttggg tgccttttga gtactggggt cagggaaccc tggtcaccgt ctcgagcgct     360
agcaccgaca tccagatgac ccagtctcca tcctccctgt ctgcatctgt aggagaccgt     420
gtcaccatca cttgccgggc aagtcgtccg attgggacga cgttaagttg gtaccagcag     480
aaaccaggga aagcccctaa gctcctgatc ctgtggaatt cccgtttgca aagtggggtc     540
ccatcacgtt tcagtggcag tggatctggg acagatttca ctctcaccat cagcagtctg     600
caacctgaag attttgctac gtactactgt gcgcaggctg ggacgcatcc tacgacgttc     660
ggccaaggga ccaaggtgga aatcaaacgg                                      690
```

<210> SEQ ID NO 33
<211> LENGTH: 690
<212> TYPE: DNA
<213> ORGANISM: Artificial Sequence
<220> FEATURE:
<223> OTHER INFORMATION: Derived from a human germline sequence

<400> SEQUENCE: 33

```
gaggtgcagc tgttggagtc tgggggaggc ttggtacagc ccggggggtc cctgcgtctc      60
tcctgtgcag cctccggatt caccttttcc aagtattcga tggggtgggt ccgccaggct     120
ccagggaagg gtctagagtg ggtctcacag atttcggata ctgctgatcg tacatactac     180
gcagactccg tgaagggccg gttcaccatc tcccgcgaca attccaagaa cacgctgtat     240
```

```
ctgcaaatga acagcctgcg tgccgaggac accgcggtat attactgtgc gatatacact    300
gggcgttggg tgccttttga gtactggggt cagggaaccc tggtcaccgt ctcgagcgct    360
agcaccgaca tccagatgac ccagtctcca tcctccctgt ctgcatctgt aggagaccgt    420
gtcaccatca cttgccgggc aagtcgtccg attgggacga cgttaagttg gtaccagcag    480
aaaccaggga aagcccctaa gctcctgatc ctttggaatt cccgtttgca aagtggggtc    540
ccatcacgtt tcagtggcag tggatctggg acagatttca ctctcaccat cagcagtctg    600
caacctgaag attttgctac gtactactgt gcgcaggctg ggacgcatcc tacgacgttc    660
ggccaaggga ccaaggtgga aatcaaacgg                                     690
```

<210> SEQ ID NO 34
<211> LENGTH: 690
<212> TYPE: DNA
<213> ORGANISM: Artificial Sequence
<220> FEATURE:
<223> OTHER INFORMATION: Derived from a human germline sequence

<400> SEQUENCE: 34

```
gaggtgcagc tgttggagtc tgggggaggc ttggtacagc ctgggggtc cctgcgtctc      60 tcctgtgcag cctccggatt cacctttgat aagtattcaa tggggtgggt ccgccaggct    120
ccagggaagg gtctagagtg ggtctcacag atttcggata ctgctgatcg tacatactac    180
gcacactccg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactggggt cagggaaccc tggtcaccgt ctcgagcgct    360
agcaccgaca tccagatgac ccagtctcca tcctccctgt ctgcatctgt aggagaccgt    420
gtcaccatca cttgccgggc aagtcgtccg attgggacga cgttaagttg gtaccagcag    480
aaaccaggga aagcccctaa gctcctgatc ctttggaatt cccgtttgca aagtggggtc    540
ccatcacgtt tcagtggcag tggatctggg acagatttca ctctcaccat cagcagtctg    600
caacctgaag attttgctac gtactactgt gcgcaggctg ggacgcatcc tacgacgttc    660
ggccaaggga ccaaggtgga aatcaaacgg                                     690
```

<210> SEQ ID NO 35
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 35

```
gaggtgcagc tgttggagtc tgggggaggc ttggtacagc ctgggggtc cctgcgtctc      60 tcctgtgcag cctccggatt cacctttgtt aagtattcga tggggtgggt ccgccaggct    120
ccagggaagg gtctagagtg ggtctcacag atttcgaata ctgctgatcg tacatactac    180
gcacactccg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactggggt cagggaaccc tggtcaccgt ctcgagc      357
```

<210> SEQ ID NO 36
<211> LENGTH: 357
<212> TYPE: DNA
<213> ORGANISM: Artificial Sequence
<220> FEATURE:

<223> OTHER INFORMATION: Derived from a human germline sequence

<400> SEQUENCE: 36

| gaggtgcagc tgttggagtc tgggggaggc ttggtacagc ctgggggggtc cctgcgtctc | 60 |
| tcctgtgcag cctccggatt cacctttgtt aagtattcga tggggtgggt ccgccaggct | 120 |
| ccagggaagg gtctagagtg ggtctcacag atttcggata ctgctgatcg tacatactac | 180 |
| gcacactccg tgaagggccg gttcaccatc tcccgcgaca attccaagaa cacgctgtat | 240 |
| ctgcaaatga acagcctgcg tgctgaggac accgcggtat attactgtgc gatatatact | 300 |
| gggcgttggg tgccttttga gtactggggt cagggaaccc tggtcaccgt ctcgagc | 357 |

<210> SEQ ID NO 37
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 37

| gaggtgcagc tgttggagtc tgggggaggc ttggtacagc ctgggggggtc cctgcgtctc | 60 |
| tcctgtgcag cctccggatt cacctttgtt aagtattcga tggggtgggt ccgccaggct | 120 |
| ccagggaagg gtctagagtg ggtctcacag atttcggata ctgctgatcg tacatactac | 180 |
| gatcactccg tgaagggccg gttcaccatc tcccgcgaca attccaagaa cacgctgtat | 240 |
| ctgcaaatga acagcctgcg tgccgaggac accgcggtat attactgtgc gatatatacg | 300 |
| ggtcgttggg agccttttgt ctactggggt cagggaaccc tggtcaccgt ctcgagc | 357 |

<210> SEQ ID NO 38
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 38

| gaggtgcagc tgttggagtc tgggggaggc ttggtacagc ctgggggggtc cctgcgtctc | 60 |
| tcctgtgcag cctccggatt cacctttttc aagtattcga tggggtgggt ccgccaggct | 120 |
| ccagggaagg gtctagagtg ggtctcacag atttcggata ctgctgatcg tacatactac | 180 |
| gcacactccg tgaagggccg gttcaccatc tcccgcgaca attccaagaa cacgctgtat | 240 |
| ctgcaaatga acagcctgcg tgccgaggac accgcggtat attactgtgc gatatatacg | 300 |
| ggtcggtggg cgccttttga gtactggggt cagggaaccc tggtcaccgt ctcgagc | 357 |

<210> SEQ ID NO 39
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 39

| gaggtgcagc tgttggagtc tgggggaggc ttggtacagc ctgggggggtc cctgcgtctc | 60 |
| tcctgtgcag cctccggatt cacctttttc aagtattcga tggggtgggt ccgccaggct | 120 |
| ccagggaagg gtctagagtg ggtctcacag atttcggata ctgctgatcg tacatactac | 180 |
| gcacactccg tgaagggccg gttcaccatc tcccgcgaca attccaagaa cacgctgtat | 240 |
| ctgcaaatga acagcctgcg tgctgaggac accgcggtat attactgtgc gatatatact | 300 |

```
gggcgttggg tgccttttga gtactggggt cagggaaccc tggtcaccgt ctcgagc      357
```

<210> SEQ ID NO 40
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 40

```
gaggtgcagc tgttggagtc tgggggaggc ttggtacagc ctgggggtc cctgcgtctc      60
tcctgtgcag cctccggatt cacctttgtt aagtattcga tggggtgggt ccgccaggct    120
ccagggaagg gtctagagtg gtctcacag atttcggata ctgctgatcg tacatactac    180
gcacacgcgg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactggggt cagggaaccc tggtcaccgt ctcgagc      357
```

<210> SEQ ID NO 41
<211> LENGTH: 357
<212> TYPE: DNA
<213> ORGANISM: Artificial Sequence
<220> FEATURE:
<223> OTHER INFORMATION: Derived from a human germline sequence

<400> SEQUENCE: 41

```
gaggtgcagc tgttggagtc tgggggaggc ttggtacagc ctgggggtc cctgcgtctc      60
tcctgtgcag cctccggatt cacctttttc aagtattcga tggggtgggt ccgccaggct    120
ccagggaagg gtctagagtg gtctcacag atttcggata ctgctgatcg tacatactac    180
tcacactccg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactggggt cagggaaccc tggtcaccgt ctcgagc      357
```

<210> SEQ ID NO 42
<211> LENGTH: 324
<212> TYPE: DNA
<213> ORGANISM: Artificial Sequence
<220> FEATURE:
<223> OTHER INFORMATION: Derived from a human germline sequence

<400> SEQUENCE: 42

```
gacatccaga tgacccagtc tccatcctcc ctgtctgcat ctgtaggaga ccgtgtcacc      60
atcacttgcc gggcaagtcg tccgattggg acgacgttaa gttggtacca gcagaaacca    120
gggaaagccc ctaagctcct gatcctttgg aattcccgtt tgcaaagtgg ggtcccatca    180
cgtttcagtg gcagtggatc tgggacagat ttcactctca ccatcagcag tctgcaacct    240
gaagattttg ctacgtacta ctgtgcgcag gctgggacgc atcctacgac gttcggccaa    300
gggaccaagg tggaaatcaa acgg                                           324
```

<210> SEQ ID NO 43
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 44
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Tyr Thr Gly Arg Trp Glu Pro Phe Glu Tyr Trp Gly Gln Gly
            100                 105                 110

Thr Leu Val Thr Val Ser Ser
        115

<210> SEQ ID NO 45
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

Ser Met Gly Trp Ile Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Val Tyr Thr Gly Arg Trp Ala Pro Phe Glu Tyr Trp Gly Gln Gly
            100                 105                 110

Thr Leu Val Thr Val Ser Ser
        115

<210> SEQ ID NO 46
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 46

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Lys Tyr
                 20                  25                  30

Ser Met Gly Trp Val Arg Gln Ala Pro Gly Lys Gly Leu Glu Trp Val
             35                  40                  45

Ser Gln Ile Ser Asp Thr Ala Asp Arg Thr Tyr Tyr Ala His Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 47
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 47

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Lys Tyr
                 20                  25                  30

Ser Met Gly Trp Val Arg Gln Ala Pro Gly Lys Gly Leu Glu Trp Val
             35                  40                  45

Ser Gln Ile Ser Asp Thr Ala Asp Arg Thr Tyr Tyr Ala His Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Val Pro Phe Glu Asn Trp Gly Gln Gly
            100                 105                 110

Thr Leu Val Thr Val Ser Ser
```

```
<210> SEQ ID NO 48
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 48

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Lys Tyr
            20                  25                  30

Ser Met Gly Trp Val Arg Gln Ala Pro Gly Lys Gly Pro Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Asn Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Glu Tyr Trp Gly Gln Gly
            100                 105                 110

Thr Leu Val Thr Val Ser Ser
        115

<210> SEQ ID NO 49
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 49

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 50
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 50
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Glu Tyr Trp Gly Gln Gly
                100                 105                 110

Thr Leu Val Thr Val Ser Ser
        115

<210> SEQ ID NO 51
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Glu Tyr Trp Gly Gln Gly
                100                 105                 110

Thr Leu Val Thr Val Ser Ser
        115

<210> SEQ ID NO 52
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Lys Asn
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Leu

```
                    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Ile Tyr Thr Gly Arg Trp Val Pro Phe Glu Tyr Trp Gly Gln Gly
                100                 105                 110

Thr Leu Val Thr Val Ser Ser
                115

<210> SEQ ID NO 53
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 53

Glu Val Gln Leu Leu Glu Ser Gly Gly Gly Leu Val Gln Pro Gly Gly
 1                5                  10                  15

Ser Leu Arg Leu Ser Cys Ala Ala Ser Gly Phe Thr Phe Lys Tyr
                 20                  25                  30

Ser Met Gly Trp Val Arg Gln Ala Pro Gly Lys Gly Leu Glu Trp Val
            35                  40                  45

Ser Gln Ile Ser Asp Thr Ala Asp Arg Thr Tyr Tyr Ala His Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Val Tyr Thr Gly Arg Trp Ala Pro Phe Glu Tyr Trp Gly Gln Gly
                100                 105                 110

Thr Leu Val Thr Val Ser Ser
                115

<210> SEQ ID NO 54
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 54

Glu Val Gln Leu Leu Glu Ser Gly Gly Gly Leu Val Gln Pro Gly Gly
 1                5                  10                  15

Ser Leu Arg Leu Ser Cys Ala Ala Ser Gly Phe Thr Phe Lys Tyr
                 20                  25                  30

Ser Met Gly Trp Val Arg Gln Ala Pro Gly Lys Gly Leu Glu Trp Val
            35                  40                  45

Ser Gln Ile Ser Asp Thr Ala Asp Arg Thr Tyr Tyr Ala His Ser Val
        50                  55                  60

Lys Gly Arg Phe Thr Ile Ser Arg Asp Asp Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Ile Tyr Thr Gly Arg Trp Ala Pro Phe Glu Tyr Trp Gly Gln Gly
                100                 105                 110
```

```
Thr Leu Val Thr Val Ser Ser
        115

<210> SEQ ID NO 55
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 55

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Ile Tyr Thr Gly Gln Trp Ala Pro Tyr Glu Tyr Trp Gly Gln Gly
            100                 105                 110

Thr Leu Val Thr Val Arg Ala
        115

<210> SEQ ID NO 56
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 56

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Lys Tyr
            20                  25                  30

Ser Met Gly Trp Val Arg Gln Ala Pro Gly Lys Asp Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Asn Trp Gly His Gly
            100                 105                 110

Thr Leu Val Thr Val Ser Ser
        115

<210> SEQ ID NO 57
<211> LENGTH: 119
<212> TYPE: PRT
<213> ORGANISM: Artificial Sequence
<220> FEATURE:
<223> OTHER INFORMATION: Derived from a human germline sequence
```

<400> SEQUENCE: 57

Glu Val Gln Leu Leu Asp Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ser Pro Ser Val
    50                  55                  60

Lys Gly Arg Phe Thr Ile Ser Arg Asp Asn Ser Gly Asn Thr Leu Asn
65                  70                  75                  80

Leu Gln Met Thr Pro Leu Arg Ala Glu Asp Thr Ala Val Tyr Tyr Cys
                85                  90                  95

Ala Ile Tyr Thr Gly Arg Trp Glu Pro Phe Glu Tyr Trp Gly Gln Gly
            100                 105                 110

Thr Leu Val Thr Val Ser Ser
        115

<210> SEQ ID NO 58
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 58

Glu Val Gln Leu Leu Glu Ser Gly Gly Gly Met Val Gln Pro Gly Gly
1               5                   10                  15

Ser Leu Arg Leu Ser Cys Ala Ser Ser Gly Phe Thr Phe Ser Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Leu Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Glu Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 59
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Lys Tyr
            20                  25                  30

Ser Met Gly Trp Val Arg Gln Ala Pro Gly Lys Gly Leu Glu Trp Val
        35                  40                  45

```
Ser Gln Ile Ser Asp Thr Ala Asp Arg Thr Tyr Tyr Ala His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
                100                 105                 110

Thr Leu Val Thr Val Ser Ser
            115

<210> SEQ ID NO 60
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
                20                  25                  30

Ser Met Gly Trp Val Arg Gln Ala Pro Gly Lys Gly Leu Glu Trp Val
            35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Ile Tyr Thr Gly Gln Trp Ala Pro Tyr Glu Tyr Trp Gly Gln Gly
                100                 105                 110

Thr Leu Val Thr Val Ser Ser
            115

<210> SEQ ID NO 61
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Lys Tyr
                20                  25                  30

Ser Met Gly Trp Val Arg Gln Ala Pro Gly Lys Gly Leu Glu Trp Val
            35                  40                  45

Ser Gln Ile Ser Asp Thr Ala Asp Arg Thr Tyr Tyr Ala His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
                100                 105                 110
```

Thr Leu Val Thr Val Ser Ser
         115

<210> SEQ ID NO 62
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 62

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Lys Tyr
             20                  25                  30

Ser Met Gly Trp Val Arg Gln Ala Pro Gly Lys Gly Leu Glu Trp Val
         35                  40                  45

Ser Gln Ile Ser Asp Thr Ala Asp Arg Thr Tyr Tyr Ala His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 63
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 63

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Lys Tyr
             20                  25                  30

Ser Met Gly Trp Val Arg Gln Ala Pro Gly Lys Gly Leu Glu Trp Val
         35                  40                  45

Ser Gln Ile Ser Asp Thr Ala Asp Arg Thr Tyr Tyr Ala His Ser Val
     50                  55                  60

Lys Gly Arg Phe Thr Ile Thr Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Glu Tyr Trp Gly Gln Gly
            100                 105                 110

Thr Leu Val Thr Val Ser Ser
        115

<210> SEQ ID NO 64
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
            115

<210> SEQ ID NO 65
<211> LENGTH: 230
<212> TYPE: PRT
<213> ORGANISM: Artificial Sequence
<220> FEATURE:
<223> OTHER INFORMATION: Derived from a human germline sequence

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Glu Tyr Trp Gly Gln Gly
            100                 105                 110

Thr Leu Val Thr Val Ser Ser Ala Ser Thr Asp Ile Gln Met Thr Gln
            115                 120                 125

Ser Pro Ser Ser Leu Ser Ala Ser Val Gly Asp Arg Val Thr Ile Thr
        130                 135                 140

Cys Arg Ala Ser Arg Pro Ile Gly Thr Thr Leu Ser Trp Tyr Gln Gln
145                 150                 155                 160

Lys Pro Gly Lys Ala Pro Lys Leu Leu Ile Leu Trp Asn Ser Arg Leu
                165                 170                 175

Gln Ser Gly Val Pro Ser Arg Phe Ser Gly Ser Gly Ser Gly Thr Asp
            180                 185                 190

Phe Thr Leu Thr Ile Ser Ser Leu Gln Pro Glu Asp Phe Ala Thr Tyr
        195                 200                 205

Tyr Cys Ala Gln Ala Gly Thr His Pro Thr Thr Phe Gly Gln Gly Thr
    210                 215                 220

```
Lys Val Glu Ile Lys Arg
225                 230

<210> SEQ ID NO 66
<211> LENGTH: 230
<212> TYPE: PRT
<213> ORGANISM: Artificial Sequence
<220> FEATURE:
<223> OTHER INFORMATION: Derived from a human germline sequence

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser Ala Ser Thr Asp Ile Gln Met Thr Gln
        115                 120                 125

Ser Pro Ser Ser Leu Ser Ala Ser Val Gly Asp Arg Val Thr Ile Thr
    130                 135                 140

Cys Arg Ala Ser Arg Pro Ile Gly Thr Thr Leu Ser Trp Tyr Gln Gln
145                 150                 155                 160

Lys Pro Gly Lys Ala Pro Lys Leu Leu Ile Leu Trp Asn Ser Arg Leu
                165                 170                 175

Gln Ser Gly Val Pro Ser Arg Phe Ser Gly Ser Gly Ser Gly Thr Asp
            180                 185                 190

Phe Thr Leu Thr Ile Ser Ser Leu Gln Pro Glu Asp Phe Ala Thr Tyr
        195                 200                 205

Tyr Cys Ala Gln Ala Gly Thr His Pro Thr Thr Phe Gly Gln Gly Thr
    210                 215                 220

Lys Val Glu Ile Lys Arg
225                 230

<210> SEQ ID NO 67
<211> LENGTH: 230
<212> TYPE: PRT
<213> ORGANISM: Artificial Sequence
<220> FEATURE:
<223> OTHER INFORMATION: Derived from a human germline sequence

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Val Pro Phe Glu Tyr Trp Gly Gln Gly
            100                 105                 110

Thr Leu Val Thr Val Ser Ser Ala Ser Thr Asp Ile Gln Met Thr Gln
            115                 120                 125

Ser Pro Ser Ser Leu Ser Ala Ser Val Gly Asp Arg Val Thr Ile Thr
130                 135                 140

Cys Arg Ala Ser Arg Pro Ile Gly Thr Thr Leu Ser Trp Tyr Gln Gln
145                 150                 155                 160

Lys Pro Gly Lys Ala Pro Lys Leu Leu Ile Leu Trp Asn Ser Arg Leu
                165                 170                 175

Gln Ser Gly Val Pro Ser Arg Phe Ser Gly Ser Gly Ser Gly Thr Asp
            180                 185                 190

Phe Thr Leu Thr Ile Ser Ser Leu Gln Pro Glu Asp Phe Ala Thr Tyr
            195                 200                 205

Tyr Cys Ala Gln Ala Gly Thr His Pro Thr Thr Phe Gly Gln Gly Thr
210                 215                 220

Lys Val Glu Ile Lys Arg
225                 230

<210> SEQ ID NO 68
<211> LENGTH: 230
<212> TYPE: PRT
<213> ORGANISM: Artificial Sequence
<220> FEATURE:
<223> OTHER INFORMATION: Derived from a human germline sequence

<400> SEQUENCE: 68

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Asp Lys Tyr
                 20                  25                  30

Ser Met Gly Trp Val Arg Gln Ala Pro Gly Lys Gly Leu Glu Trp Val
            35                  40                  45

Ser Gln Ile Ser Asp Thr Ala Asp Arg Thr Tyr Tyr Ala His Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Val Pro Phe Glu Tyr Trp Gly Gln Gly
            100                 105                 110

Thr Leu Val Thr Val Ser Ser Ala Ser Thr Asp Ile Gln Met Thr Gln
            115                 120                 125

Ser Pro Ser Ser Leu Ser Ala Ser Val Gly Asp Arg Val Thr Ile Thr
130                 135                 140

Cys Arg Ala Ser Arg Pro Ile Gly Thr Thr Leu Ser Trp Tyr Gln Gln
145                 150                 155                 160

Lys Pro Gly Lys Ala Pro Lys Leu Leu Ile Leu Trp Asn Ser Arg Leu
                165                 170                 175

Gln Ser Gly Val Pro Ser Arg Phe Ser Gly Ser Gly Ser Gly Thr Asp
            180                 185                 190
```

```
Phe Thr Leu Thr Ile Ser Ser Leu Gln Pro Glu Asp Phe Ala Thr Tyr
        195                 200                 205

Tyr Cys Ala Gln Ala Gly Thr His Pro Thr Thr Phe Gly Gln Gly Thr
    210                 215                 220

Lys Val Glu Ile Lys Arg
225                 230

<210> SEQ ID NO 69
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 70
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115
```

-continued

```
<210> SEQ ID NO 71
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 71

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asp Thr Ala Asp Arg Thr Tyr Tyr Asp His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 72
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 72

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Phe Lys Tyr
             20                  25                  30

Ser Met Gly Trp Val Arg Gln Ala Pro Gly Lys Gly Leu Glu Trp Val
         35                  40                  45

Ser Gln Ile Ser Asp Thr Ala Asp Arg Thr Tyr Tyr Ala His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 73
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 73

Glu Val Gln Leu Leu Glu Ser Gly Gly Gly Leu Val Gln Pro Gly Gly
  1               5                  10                  15
```

```
Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
            35                  40                  45

Ser Gln Ile Ser Asp Thr Ala Asp Arg Thr Tyr Tyr Ala His Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
            115
```

<210> SEQ ID NO 74
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 74

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
            35                  40                  45

Ser Gln Ile Ser Asp Thr Ala Asp Arg Thr Tyr Tyr Ala His Ala Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
            115
```

<210> SEQ ID NO 75
<211> LENGTH: 119
<212> TYPE: PRT
<213> ORGANISM: Artificial Sequence
<220> FEATURE:
<223> OTHER INFORMATION: Derived from a human germline sequence

<400> SEQUENCE: 75

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
            35                  40                  45

Ser Gln Ile Ser Asp Thr Ala Asp Arg Thr Tyr Tyr Ser His Ser Val
        50                  55                  60

Lys Gly Arg Phe Thr Ile Ser Arg Asp Asn Ser Lys Asn Thr Leu Tyr
```

-continued

```
                65                  70                  75                  80
Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 76
<211> LENGTH: 108
<212> TYPE: PRT
<213> ORGANISM: Artificial Sequence
<220> FEATURE:
<223> OTHER INFORMATION: Derived from a human germline sequence

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Gly Thr Thr
            20                  25                  30

Leu Ser Trp Tyr Gln Gln Lys Pro Gly Lys Ala Pro Lys Leu Leu Ile
        35                  40                  45

Leu Trp Asn Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Ala Gly Thr His Pro Thr
                85                  90                  95

Thr Phe Gly Gln Gly Thr Lys Val Glu Ile Lys Arg
            100                 105
```

US 9,028,817 B2

STABLE ANTI-TNFR1 POLYPEPTIDES, ANTIBODY VARIABLE DOMAINS AND ANTAGONISTS

This application is a 371 of International Application No. PCT/EP2010/066046, filed 25 Oct. 2010, which claims the benefit of U.S. Provisional Application No. 61/255,235, filed 27 Oct. 2009, both of which are herein incorporated by reference in their entireties.

The present invention relates to anti-Tumor Necrosis Factor 1 (TNFR1, p55, CD120a, P60, TNF receptor superfamily member 1A, TNFRSF1A) polypeptides, immunoglobulin (antibody) single variable domains and antagonists comprising these. The invention further relates to methods, uses, formulations, compositions and devices comprising or using such anti-TNFR1 ligands.

BACKGROUND OF THE INVENTION

TNFR1

TNFR1 is a transmembrane receptor containing an extracellular region that binds ligand and an intracellular domain that lacks intrinsic signal transduction activity but can associate with signal transduction molecules. The complex of TNFR1 with bound TNF contains three TNFR1 chains and three TNF chains. (Banner et al., *Cell*, 73(3) 431-445 (1993).) The TNF ligand is present as a trimer, which is bound by three TNFR1 chains. (Id.) The three TNFR1 chains are clustered closely together in the receptor-ligand complex, and this clustering is a prerequisite to TNFR1-mediated signal transduction. In fact, multivalent agents that bind TNFR1, such as anti-TNFR1 antibodies, can induce TNFR1 clustering and signal transduction in the absence of TNF and are commonly used as TNFR1 agonists. (See, e.g., Belka et al., *EMBO*, 14(6):1156-1165 (1995); Mandik-Nayak et al., *J. Immunol*, 167:1920-1928 (2001).) Accordingly, multivalent agents that bind TNFR1 are generally not effective antagonists of TNFR1 even if they block the binding of TNFα to TNFR1.

SEQ ID numbers in this paragraph refer to the numbering used in WO2006038027. The extracellular region of TNFR1 comprises a thirteen amino acid amino-terminal segment (amino acids 1-13 of SEQ ID NO:603 (human); amino acids 1-13 of SEQ ID NO:604 (mouse)), Domain 1 (amino acids 14-53 of SEQ ID NO:603 (human); amino acids 14-53 of SEQ ID NO:604 (mouse)), Domain 2 (amino acids 54-97 of SEQ ID NO: 603 (human); amino acids 54-97 of SEQ ID NO:604 (mouse)), Domain 3 (amino acids 98-138 of SEQ ID NO: 603 (human); amino acid 98-138 of SEQ ID NO:604 (mouse)), and Domain 4 (amino acids 139-167 of SEQ ID NO:603 (human); amino acids 139-167 of SEQ ID NO:604 (mouse)) which is followed by a membrane-proximal region (amino acids 168-182 of SEQ ID NO:603 (human); amino acids 168-183 SEQ ID NO: 604 (mouse)). (See, Banner et al., *Cell* 73(3) 431-445 (1993) and Loetscher et al., *Cell* 61(2) 351-359 (1990).) Domains 2 and 3 make contact with bound ligand (TNFβ, TNFα). (Banner et al., *Cell*, 73(3) 431-445 (1993).) The extracellular region of TNFR1 also contains a region referred to as the pre-ligand binding assembly domain or PLAD domain (amino acids 1-53 of SEQ ID NO:603 (human); amino acids 1-53 of SEQ ID NO:604 (mouse)) (The Government of the USA, WO 01/58953; Deng et al., *Nature Medicine*, doi: 10.1038/nm1304 (2005)).

TNFR1 is shed from the surface of cells in vivo through a process that includes proteolysis of TNFR1 in Domain 4 or in the membrane-proximal region (amino acids 168-182 of SEQ ID NO:603; amino acids 168-183 of SEQ ID NO:604), to produce a soluble form of TNFR1. Soluble TNFR1 retains the capacity to bind TNFα, and thereby functions as an endogenous inhibitor of the activity of TNFα.

WO2006038027, WO2008149144 and WO2008149148 disclose anti-TNFR1 immunoglobulin single variable domains and antagonists comprising these. These documents also disclose the use of such domains and antagonists for the treatment and/or prevention of conditions mediated by TNFα. It would be desirable to provide anti-human TNFR1 immunoglobulin single variable domains with improved storage stability, antagonists, ligands and products comprising these. The aim of these would be to provide improved diagnostic reagents for detecting human TNFR1 in samples, as well as or alternatively to provide improved therapeutics for the treatment and/or prophylaxis of TNFR1-mediated conditions and diseases in humans or other mammals. It would be particularly desirable to provide anti-TNFR1 immunoglobulin single variable domains, antagonists, ligands and products comprising these that are potent neutralizers of TNFR1, especially of human TNFR1

The various aspects of the present invention meet these desirable characteristics.

SUMMARY OF THE INVENTION

In one aspect, the invention provides an anti-TNFα receptor type 1 (TNFR1; p55) immunoglobulin single variable domain comprising an amino acid sequence that is at least 95, 96, 97, 98 or 99% identical (or is 100% identical) to the amino acid sequence of DOM1h-574-188, DOM1h-574-189, DOM1h-574-190, DOM1h-574-191, DOM1h-574-192, DOM1h-574-195, DOM1h-574-196, DOM1h-574-201, DOM1h-574-202, DOM1h-574-203, DOM1h-574-204, DOM1h-574-205, DOM1h-574-206, DOM1h-574-207, DOM1h-574-208, DOM1h-574-209, DOM1h-574-211, DOM1h-574-212, DOM1h-574-213 or DOM1h-574-214, wherein the single variable domain has an $OD_{320}<1.0$, $<0.9$, $<0.8$, $<0.7$, $<0.6$, $<0.5$, or $<0.4$ after incubation in PBS at 40° C. for 40 hours. In one embodiment, the single variable domain has an $OD_{320}<1.0$, $<0.9$, $<0.8$, $<0.7$, $<0.6$, $<0.5$, or $<0.4$ determined by the following test a) 100 µl of 1 mg/ml single variable domain in PBS (phosphate buffered saline) is dispensed onto a PCR plate;
b) The plate is incubated for 40 hours at 40° C.; and
c) An aliquot of 50 µl is removed and the $OD_{320}$ is measured, for example, in a microplate reader (eg, one from Molecular Devices).

In one aspect, the invention provides an anti-TNFα receptor type 1 (TNFR1; p55) immunoglobulin single variable domain comprising an amino acid sequence that is at least 95, 96, 97, 98 or 99% identical (or is 100% identical) to the amino acid sequence of DOM1h-574-188, DOM1h-574-189, DOM1h-574-190, DOM1h-574-191, DOM1h-574-192, DOM1h-574-193, DOM1h-574-194, DOM1h-574-195, DOM1h-574-196, DOM1h-574-201, DOM1h-574-202, DOM1h-574-203, DOM1h-574-204, DOM1h-574-205, DOM1h-574-206, DOM1h-574-207, DOM1h-574-208, DOM1h-574-209, DOM1h-574-211, DOM1h-574-212, DOM1h-574-213 or DOM1h-574-214.

In one aspect, the invention provides an anti-TNFα receptor type 1 (TNFR1; p55) immunoglobulin single variable domain comprising an amino acid sequence that is identical to an amino acid sequence selected from DOM1h-574-188, DOM1h-574-189, DOM1h-574-190, DOM1h-574-191, DOM1h-574-192, DOM1h-574-193, DOM1h-574-194, DOM1h-574-195, DOM1h-574-196, DOM1h-574-201, DOM1h-574-202, DOM1h-574-203, DOM1h-574-204, DOM1h-574-205, DOM1h-574-206, DOM1h-574-207, DOM1h-574-208, DOM1h-574-209, DOM1h-574-211, DOM1h-574-212, DOM1h-574-213 and DOM1h-574-214 or has 1 or 2 amino acid changes compared to said selected amino acid sequence.

In one aspect, the invention provides a nucleic acid comprising a nucleotide sequence that encodes an anti-TNFα receptor type 1 (TNFR1; p55) immunoglobulin single variable domain, wherein the variable domain comprises an amino acid sequence that is at least 95, 96, 97, 98 or 99% identical (or is 100% identical) to the amino acid sequence of DOM1h-574-188, DOM1h-574-189, DOM1h-574-190, DOM1h-574-191, DOM1h-574-192, DOM1h-574-193, DOM1h-574-194, DOM1h-574-195, DOM1h-574-196, DOM1h-574-201, DOM1h-574-202, DOM1h-574-203, DOM1h-574-204, DOM1h-574-205, DOM1h-574-206, DOM1h-574-207, DOM1h-574-208, DOM1h-574-209, DOM1h-574-211, DOM1h-574-212, DOM1h-574-213 or DOM1h-574-214.

In one aspect, the invention provides a nucleic acid comprising a nucleotide sequence that encodes an anti-TNFα receptor type 1 (TNFR1; p55) immunoglobulin single variable domain, wherein the nucleotide sequence is at least 70, 75 80, 85, 90, 95, 96, 97, 98 or 99% identical (or is 100% identical) to the nucleotide sequence of DOM1h-574-188, DOM1h-574-189, DOM1h-574-190, DOM1h-574-191, DOM1h-574-192, DOM1h-574-193, DOM1h-574-194, DOM1h-574-195, DOM1h-574-196, DOM1h-574-201, DOM1h-574-202, DOM1h-574-203, DOM1h-574-204, DOM1h-574-205, DOM1h-574-206, DOM1h-574-207, DOM1h-574-208, DOM1h-574-209, DOM1h-574-211, DOM1h-574-212, DOM1h-574-213 or DOM1h-574-214.

In one aspect, the invention relates to a multispecific ligand comprising an immunoglobulin single variable domain of the present invention and optionally at least one immunoglobulin single variable domain that specifically binds serum albumin (SA). In one embodiment, the multispecific ligand is, or comprises, an amino acid sequence selected from the amino acid sequence of any construct labeled "DMS" disclosed herein, for example, any one of DMS5535, 5541, 5542 and 5544. In one embodiment, the multispecific ligand is, or comprises, an amino acid sequence encoded by the nucleotide sequence of any DMS disclosed herein, for example, any one of the nucleotide sequences of DMS5535, 5541, 5542 and 5544. In one embodiment, the invention provides a nucleic acid encoding a multispecific ligand comprising an anti-TNFR1 immunoglobulin single variable domain and an anti-SA single variable domain, wherein the nucleic acid comprises the nucleotide sequence of any DMS disclosed herein, for example, any one of the nucleotide sequences of DMS5535, 5541, 5542 and 5544. There is provided a vector comprising such a nucleic acid, as well as a host cell comprising such a vector.

In one aspect, the invention provides a multispecific ligand comprising (i) an anti-TNFα receptor type 1 (TNFR1; p55) immunoglobulin single variable domain which comprises an amino acid sequence that is at least 95, 96, 97, 98 or 99% identical (or is 100% identical) to the amino acid sequence of DOM1h-574-188, DOM1h-574-189, DOM1h-574-190, DOM1h-574-191, DOM1h-574-192, DOM1h-574-193, DOM1h-574-194, DOM1h-574-195, DOM1h-574-196, DOM1h-574-201, DOM1h-574-202, DOM1h-574-203, DOM1h-574-204, DOM1h-574-205, DOM1h-574-206, DOM1h-574-207, DOM1h-574-208, DOM1h-574-209, DOM1h-574-211, DOM1h-574-212, DOM1h-574-213 or DOM1h-574-214, (ii) at least one anti-serum albumin (SA) immunoglobulin single variable domain that specifically binds SA, wherein the anti-SA single variable domain comprises an amino acid sequence that is at least 80% identical to the sequence of DOM7h-11-3, and (iii) optionally wherein a linker is provided between the anti-TNFR1 single variable domain and the anti-SA single variable domain.

In one embodiment, the linker comprises the amino acid sequence AST, optionally ASTSGPS. Alternatively, the linker is $AS(G_4S)_n$, where n is 1, 2, 3, 4, 5, 6, 7 or 8, for example $AS(G_4S)_3$.

In one aspect, the invention provides a TNFR1 antagonist comprising a single variable domain, polypeptide or multispecific ligand of any preceding aspect of the invention.

In one aspect, the invention provides a TNFα receptor type 1 (TNFR1; p55) antagonist of the invention, for oral delivery, delivery to the GI tract of a patient, pulmonary delivery, delivery to the lung of a patient or systemic delivery.

In one aspect, the invention provides a TNFR1 antagonist of the invention for treating and/or prophylaxis of an inflammatory condition.

In one aspect, the invention provides the use of the TNFR1 antagonist of the invention in the manufacture of a medicament for treating and/or prophylaxis of an inflammatory condition.

Another aspect of the invention provides multispecific ligand comprising or consisting of DMS5535, DMS5541, DMS5542 or DMS5544. An aspect of the invention provides a nucleic acid encoding either multispecific ligand. Another aspect of the invention provides a nucleic acid comprising a nucleotide sequence that is at least 80% identical to the nucleotide sequence of DMS5535, DMS5541, DMS5542 or DMS5544. The invention further provides a vector comprising the nucleic acid, as well as a host, optionally a non-human embryonic cell, comprising the vector.

BRIEF DESCRIPTION OF THE FIGURE

FIG. 1. Amino-acid sequence alignment for dAbs from stability selections and purified for characterisation. The sequences are aligned against DOM1h-574-156, a dAb representative for those used as starting dAb for the stability selections. A "." at a particular position indicates the same amino as found in DOM1h-574-156 at that position. The CDRs are indicated by underlining and bold text (the first underlined sequence is CDR1, the second underlined sequence is CDR2 and the third underlined sequence is CDR3).

DETAILED DESCRIPTION OF THE INVENTION

Within this specification the invention has been described, with reference to embodiments, in a way which enables a clear and concise specification to be written. It is intended and should be appreciated that embodiments may be variously combined or separated without parting from the invention.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) $4^{th}$ Ed, John Wiley & Sons, Inc. which are incorporated herein by reference) and chemical methods.

The immunoglobulin single variable domains (dAbs) described herein contain complementarity determining regions (CDR1, CDR2 and CDR3). The locations of CDRs and frame work (FR) regions and a numbering system have been defined by Kabat et al. (Kabat, E. A. et al., *Sequences of Proteins of Immunological Interest*, Fifth Edition, U.S. Department of Health and Human Services, U.S. Government Printing Office (1991)). The amino acid sequences of the CDRs (CDR1, CDR2, CDR3) of the $V_H$ and $V_L$ ($V_K$) dAbs disclosed herein will be readily apparent to the person of skill in the art based on the well known Kabat amino acid numbering system and definition of the CDRs. According to the Kabat numbering system heavy chain CDR-H3 have varying lengths, insertions are numbered between residue H100 and H101 with letters up to K (i.e. H100, H100A . . . H100K, H101). CDRs can alternatively be determined using the system of Chothia (Chothia et al., (1989) Conformations of immunoglobulin hypervariable regions; Nature 342, p877-883), according to AbM or according to the Contact method as follows. See http://www.bioinf.org.uk/abs/ for suitable methods for determining CDRs.

Once each residue has been numbered, one can then apply the following CDR definitions ("-" means same residue numbers as shown for Kabat):
Kabat—most commonly used method based on sequence variability
    (using Kabat numbering):
    CDR H1: 31-35/35A/35B
    CDR H2: 50-65
    CDR H3: 95-102
    CDR L1: 24-34
    CDR L2: 50-56
    CDR L3: 89-97
Chothia—based on location of the structural loop regions
    (using Chothia numbering):
    CDR H1: 26-32
    CDR H2: 52-56
    CDR H3: 95-102
    CDR L1: 24-34
    CDR L2: 50-56
    CDR L3: 89-97
AbM—compromise between Kabat and Chothia
    (using Kabat numbering): (using Chothia numbering):
    CDR H1: 26-35/35A/35B 26-35
    CDR H2: 50-58 -
    CDR H3: 95-102 -
    CDR L1: 24-34 -
    CDR L2: 50-56 -
    CDR L3: 89-97 -
Contact—based on crystal structures and prediction of contact residues with antigen (using Kabat numbering): (using Chothia numbering):
    CDR H1: 30-35/35A/35B 30-35
    CDR H2: 47-58 -
    CDR H3: 93-101 -
    CDR L1: 30-36 -
    CDR L2: 46-55 -
    CDR L3: 89-96 -

As used herein, the term "antagonist of Tumor Necrosis Factor Receptor 1 (TNFR1)" or "anti-TNFR1 antagonist" or the like refers to an agent (e.g., a molecule, a compound) which binds TNFR1 and can inhibit a (i.e., one or more) function of TNFR1. For example, an antagonist of TNFR1 can inhibit the binding of TNFα to TNFR1 and/or inhibit signal transduction mediated through TNFR1. Accordingly, TNFR1-mediated processes and cellular responses (e.g., TNFα-induced cell death in a standard L929 cytotoxicity assay) can be inhibited with an antagonist of TNFR1.

As used herein, "peptide" refers to about two to about 50 amino acids that are joined together via peptide bonds.

As used herein, "polypeptide" refers to at least about 50 amino acids that are joined together by peptide bonds. Polypeptides generally comprise tertiary structure and fold into functional domains.

As used herein, a peptide or polypeptide (e.g. a domain antibody (dAb)) that is "resistant to protease degradation" is not substantially degraded by a protease when incubated with the protease under conditions suitable for protease activity. A polypeptide (e.g., a dAb) is not substantially degraded when no more than about 25%, no more than about 20%, no more than about 15%, no more than about 14%, no more than about 13%, no more than about 12%, no more than about 11%, no more than about 10%, no more than about 9%, no more than about 8%, no more than about 7%, no more than about 6%, no more than about 5%, no more than about 4%, no more than about 3%, no more that about 2%, no more than about 1%, or substantially none of the protein is degraded by protease after incubation with the protease for about one hour at a temperature suitable for protease activity, for example at 37 or 50 degrees C. Protein degradation can be assessed using any suitable method, for example, by SDS-PAGE or by functional assay (e.g., ligand binding) as described herein.

As used herein, "display system" refers to a system in which a collection of polypeptides or peptides are accessible for selection based upon a desired characteristic, such as a physical, chemical or functional characteristic. The display system can be a suitable repertoire of polypeptides or peptides (e.g., in a solution, immobilized on a suitable support). The display system can also be a system that employs a cellular expression system (e.g., expression of a library of nucleic acids in, e.g., transformed, infected, transfected or transduced cells and display of the encoded polypeptides on the surface of the cells) or an acellular expression system (e.g., emulsion compartmentalization and display). Exemplary display systems link the coding function of a nucleic acid and physical, chemical and/or functional characteristics of a polypeptide or peptide encoded by the nucleic acid. When such a display system is employed, polypeptides or peptides that have a desired physical, chemical and/or functional characteristic can be selected and a nucleic acid encoding the selected polypeptide or peptide can be readily isolated or recovered. A number of display systems that link the coding function of a nucleic acid and physical, chemical and/or functional characteristics of a polypeptide or peptide are known in the art, for example, bacteriophage display (phage display, for example phagemid display), ribosome display, emulsion compartmentalization and display, yeast display, puromycin display, bacterial display, display on plasmid, covalent display and the like. (See, e.g., EP 0436597 (Dyax), U.S. Pat. No. 6,172,197 (McCafferty et al.), U.S. Pat. No. 6,489,103 (Griffiths et al.).)

As used herein, "repertoire" refers to a collection of polypeptides or peptides that are characterized by amino acid sequence diversity. The individual members of a repertoire can have common features, such as common structural features (e.g., a common core structure) and/or common functional features (e.g., capacity to bind a common ligand (e.g., a generic ligand or a target ligand, TNFR1)).

As used herein, "functional" describes a polypeptide or peptide that has biological activity, such as specific binding activity. For example, the term "functional polypeptide" includes an antibody or antigen-binding fragment thereof that binds a target antigen through its antigen-binding site.

As used herein, "generic ligand" refers to a ligand that binds a substantial portion (e.g., substantially all) of the functional members of a given repertoire. A generic ligand (e.g., a common generic ligand) can bind many members of a given repertoire even though the members may not have binding specificity for a common target ligand. In general, the presence of a functional generic ligand-binding site on a polypeptide (as indicated by the ability to bind a generic ligand) indicates that the polypeptide is correctly folded and functional. Suitable examples of generic ligands include superantigens, antibodies that bind an epitope expressed on a substantial portion of functional members of a repertoire, and the like.

"Superantigen" is a term of art that refers to generic ligands that interact with members of the immunoglobulin superfamily at a site that is distinct from the target ligand-binding sites of these proteins. Staphylococcal enterotoxins are examples of superantigens which interact with T-cell receptors. Superantigens that bind antibodies include Protein G, which binds the IgG constant region (Bjorck and Kronvall, *J. Immunol.*, 133:969 (1984)); Protein A which binds the IgG constant region and $V_H$ domains (Forsgren and Sjoquist, *J. Immunol.*, 97:822 (1966)); and Protein L which binds $V_L$ domains (Bjorck, *J. Immunol.*, 140:1194 (1988)).

As used herein, "target ligand" refers to a ligand which is specifically or selectively bound by a polypeptide or peptide. For example, when a polypeptide is an antibody or antigen-binding fragment thereof, the target ligand can be any desired antigen or epitope. Binding to the target antigen is dependent upon the polypeptide or peptide being functional.

As used herein an antibody refers to IgG, IgM, IgA, IgD or IgE or a fragment (such as a Fab, F(ab')$_2$, Fv, disulphide linked Fv, scFv, closed conformation multispecific antibody, disulphide-linked scFv, diabody) whether derived from any species naturally producing an antibody, or created by recombinant DNA technology; whether isolated from serum, B-cells, hybridomas, transfectomas, yeast or bacteria.

As used herein, "antibody format", "formatted" or similar refers to any suitable polypeptide structure in which one or more antibody variable domains can be incorporated so as to confer binding specificity for antigen on the structure. A variety of suitable antibody formats are known in the art, such as, chimeric antibodies, humanized antibodies, human antibodies, single chain antibodies, bispecific antibodies, antibody heavy chains, antibody light chains, homodimers and heterodimers of antibody heavy chains and/or light chains, antigen-binding fragments of any of the foregoing (e.g., a Fv fragment (e.g., single chain Fv (scFv), a disulfide bonded Fv), a Fab fragment, a Fab' fragment, a F(ab')$_2$ fragment), a single antibody variable domain (e.g., a dAb, $V_H$, $V_{HH}$, $V_L$), and modified versions of any of the foregoing (e.g., modified by the covalent attachment of polyethylene glycol or other suitable polymer or a humanized $V_{HH}$).

The phrase "immunoglobulin single variable domain" refers to an antibody variable domain ($V_H$, $V_{HH}$, $V_L$) that specifically binds an antigen or epitope independently of other V regions or domains. An immunoglobulin single variable domain can be present in a format (e.g., homo- or heteromultimer) with other variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" as the term is used herein. A "single immunoglobulin variable domain" is the same as an "immunoglobulin single variable domain" as the term is used herein. A "single antibody variable domain" or an "antibody single variable domain" is the same as an "immunoglobulin single variable domain" as the term is used herein. An immunoglobulin single variable domain is in one embodiment a human antibody variable domain, but also includes single antibody variable domains from other species such as rodent (for example, as disclosed in WO 00/29004, the contents of which are incorporated herein by reference in their entirety), nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. The $V_{HH}$ may be humanized.

A "domain" is a folded protein structure which has tertiary structure independent of the rest of the protein. Generally, domains are responsible for discrete functional properties of proteins, and in many cases may be added, removed or transferred to other proteins without loss of function of the remainder of the protein and/or of the domain. A "single antibody variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

The term "library" refers to a mixture of heterogeneous polypeptides or nucleic acids. The library is composed of members, each of which has a single polypeptide or nucleic acid sequence. To this extent, "library" is synonymous with "repertoire." Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids. In one embodiment, each individual organism or cell contains only one or a limited number of library members. In one embodiment, the nucleic acids are incorporated into expression vectors, in order to allow expression of the polypeptides encoded by the nucleic acids. In an aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of diverse polypeptides.

A "universal framework" is a single antibody framework sequence corresponding to the regions of an antibody conserved in sequence as defined by Kabat ("Sequences of Proteins of Immunological Interest", US Department of Health and Human Services) or corresponding to the human germline immunoglobulin repertoire or structure as defined by Chothia and Lesk, (1987) J. Mol. Biol. 196:910-917. Libraries and repertoires can use a single framework, or a set of such frameworks, which has been found to permit the derivation of virtually any binding specificity though variation in the hypervariable regions alone.

As used herein, the term "dose" refers to the quantity of ligand administered to a subject all at one time (unit dose), or in two or more administrations over a defined time interval. For example, dose can refer to the quantity of ligand (e.g., ligand comprising an immunoglobulin single variable domain that binds target antigen) administered to a subject over the course of one day (24 hours) (daily dose), two days, one week, two weeks, three weeks or one or more months (e.g., by a single administration, or by two or more administrations). The interval between doses can be any desired amount of time.

As used herein, "hydrodynamic size" refers to the apparent size of a molecule (e.g., a protein molecule, ligand) based on the diffusion of the molecule through an aqueous solution. The diffusion, or motion of a protein through solution can be processed to derive an apparent size of the protein, where the size is given by the "Stokes radius" or "hydrodynamic radius" of the protein particle. The "hydrodynamic size" of a protein depends on both mass and shape (conformation), such that two proteins having the same molecular mass may have differing hydrodynamic sizes based on the overall conformation of the protein.

As referred to herein, the term "competes" means that the binding of a first target to its cognate target binding domain is inhibited in the presence of a second binding domain that is specific for the cognate target. For example, binding may be inhibited sterically, for example by physical blocking of a binding domain or by alteration of the structure or environment of a binding domain such that its affinity or avidity for a target is reduced. See WO2006038027 for details of how to perform competition ELISA and competition BiaCore experiments to determine competition between first and second binding domains.

Calculations of "homology" or "identity" or "similarity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In an embodiment, the length of a reference sequence aligned for comparison purposes is at least 30%, or at least 40%, or at least 50%, or at least 60%, or at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "homology" is equivalent to amino acid or nucleic acid "identity"). The percent identity between the two sequences is a function of the number of identical positions shared by the sequences, taking into account the number of gaps, and the length of each gap, which need to be introduced for optimal alignment of the two sequences Amino acid and nucleotide sequence alignments and homology, similarity or identity, as defined herein may be prepared and determined using the algorithm BLAST 2 Sequences, using default parameters (Tatusova, T. A. et al., *FEMS Microbiol Lett*, 174:187-188 (1999)).

In one embodiment of any aspect of the invention, the anti-TNFR1 single variable, antagonist, ligand or polypeptide neutralizes TNFR1 (eg, human TNFR1) with an ND50 of (or about of) 5, 4, 3, 2 or 1 nM or less in a standard MRC5 assay as determined by inhibition of TNF alpha-induced IL-8 secretion.

In one embodiment of any aspect of the invention, the anti-TNFR1 single variable, antagonist, ligand or polypeptide neutralizes TNFR1 (eg, murine TNFR1) with an ND50 of 150, 100, 50, 40, 30 or 20 nM or less; or from (about) 150 to 10 nM; or from (about) 150 to 20 nM; or from (about) 110 to 10 nM; or from (about) 110 to 20 nM in a standard L929 assay as determined by inhibition of TNF alpha-induced cytotoxicity.

In one embodiment of any aspect of the invention, the anti-TNFR1 single variable, antagonist, ligand or polypeptide neutralises TNFR1 (eg, Cynomologus monkey TNFR1) with an ND50 of 5, 4, 3, 2 or 1 nM or less; or (about) 5 to (about) 1 nM in a standard Cynomologus KI assay as determined by inhibition of TNF alpha-induced IL-8 secretion.

In one embodiment of any aspect of the invention, the single variable domain comprises a terminal, optionally C-terminal, cysteine residue. For example, the cysteine residue can be used to attach PEG to the variable domain, eg, using a maleimide linkage (see, eg, WO04081026). In an embodiment of any aspect of the invention, the single variable domain is linked to a polyalkylene glycol moiety, optionally a polyethylene glycol moiety. See, eg, WO04081026, for suitable PEG moieties and conjugation methods and tests. These disclosures are incorporated herein in order to provide disclosure, for example of specific PEGs to be included in claims below.

In one aspect, the invention relates to a polypeptide comprising an immunoglobulin single variable domain of the present invention and an effector group or an antibody constant domain, optionally an antibody Fc region, optionally wherein the N-terminus of the Fc is linked (optionally directly linked) to the C-terminus of the variable domain. Any "effector group" as described in WO04058820 can be used in this aspect of the present invention, and the description of the effector groups in WO04058820 and methods of linking them to variable domains disclosed in that publication are explicitly incorporated herein by reference to provide description herein that can be used, for example, in claims herein.

In one aspect, the invention relates to a multispecific ligand comprising an immunoglobulin single variable domain of the present invention and optionally at least one immunoglobulin single variable domain that specifically binds serum albumin (SA). In one embodiment, the multispecific ligand binds TNFR1 (eg, human TNFR1) with a KD that is at least two-fold lower than the KD of the TNFR1 monomer. Additionally or alternatively, in one embodiment, the multispecific ligand has a half-life that is at least 5, 10, 20, 30, 40, 50 or 100 times that of the monomer. Additionally or alternatively, in one embodiment, the multispecific ligand has a terminal half-life of at least 15, 16, 17, 18, 19, 20, 21, 22, 23, 24 or 25 days in man (for example as determined empirically in human volunteers or as calculated using conventional techniques familiar to the skilled person by extrapolating from the half-life of the ligand in an animal system such as mouse, dog and/or non-human primate (eg, Cynomolgus monkey, baboon, rhesus monkey)), for example where the anti-SA domain is cross-reactive between human SA and SA from the animal.

In one embodiment of the multispecific ligands of the invention, the ligand is an antagonist of TNFR1 (eg, human TNFR1), optionally of TNFR1-mediated signaling.

In one embodiment, the present invention provides the variable domain, multispecific ligand or antagonist according to the invention that has a tβ half-life in the range of (or of about) 2.5 hours or more. In one embodiment, the lower end of the range is (or is about) 3 hours, 4 hours, 5 hours, 6 hours, 7 hours, 10 hours, 11 hours, or 12 hours. In addition, or alternatively, the tβ half-life is (or is about) up to and including 21 or 25 days. In one embodiment, the upper end of the range is (or is about) 12 hours, 24 hours, 2 days, 3 days, 5 days, 10 days, 15 days, 19 days 20 days, 21 days or 22 days. For example, the variable domain or antagonist according to the invention will have a tβ half life in the range 12 to 60 hours (or about 12 to 60 hours). In a further embodiment, it will be in the range 12 to 48 hours (or about 12 to 48 hours). In a further embodiment still, it will be in the range 12 to 26 hours (or about 12 to 26 hours).

As an alternative to using two-compartment modeling, the skilled person will be familiar with the use of non-compartmental modeling, which can be used to determine terminal half-lives (in this respect, the term "terminal half-life" as used herein means a terminal half-life determined using non-compartmental modeling). The WinNonlin analysis package, eg version 5.1 (available from Pharsight Corp., Mountain View, Calif. 94040, USA) can be used, for example, to model the curve in this way. In this instance, in one embodiment the single variable domain, multispecific ligand or antagonist has a terminal half life of at least (or at least about) 8 hours, 10 hours, 12 hours, 15 hours, 28 hours, 20 hours, 1 day, 2 days, 3 days, 7 days, 14 days, 15 days, 16 days, 17 days, 18 days, 19 days, 20 days, 21 days, 22 days, 23 days, 24 days or 25 days. In one embodiment, the upper end of this range is (or is about) 24 hours, 48 hours, 60 hours or 72 hours or 120 hours. For example, the terminal half-life is (or is about) from 8 hours to 60 hours, or 8 hours to 48 hours or 12 to 120 hours, eg, in man.

In addition, or alternatively to the above criteria, the variable domain or antagonist according to the invention has an AUC value (area under the curve) in the range of (or of about) 1 mg·min/ml or more. In one embodiment, the lower end of the range is (or is about) 5, 10, 15, 20, 30, 100, 200 or 300 mg·min/ml. In addition, or alternatively, the variable domain, multispecific ligand or antagonist according to the invention has an AUC in the range of (or of about) up to 600 mg·min/ml. In one embodiment, the upper end of the range is (or is about) 500, 400, 300, 200, 150, 100, 75 or 50 mg·min/ml. Advantageously the variable domain or antagonist will have a AUC in (or about in) the range selected from the group consisting of the following: 15 to 150 mg·min/ml, 15 to 100 mg·min/ml, 15 to 75 mg·min/ml, and 15 to 50 mg·min/ml.

One or more of the t alpha, t beta and terminal half-lives as well as the AUCs quoted herein can be obtained in a human and/or animal (eg, mouse or non-human primate, eg, baboon, rhesus, Cynomolgus monkey) by providing one or more anti-TNFR1 single variable domains (or other binding moieties defined herein) linked to either a PEG or a single variable domain (or binding moiety) that specifically binds to serum albumin, eg mouse and/or human serum albumin (SA). The PEG size can be (or be about) at least 20 kDa, for example, 30, 40, 50, 60, 70 or 80 kDa. In one embodiment, the PEG is 40 kDa, eg 2×20 kDa PEG. In one embodiment, to obtain at alpha, t beta and terminal half-lives or an AUC quoted herein, there is provide an antagonist comprising an anti-TNFR1 immunoglobulin single variable domain linked to an anti-SA immunoglobulin single variable domain. In one embodiment, the PEG is 40 kDa, eg 2×20 kDa PEG. For example, the antagonist comprises only one such anti-TNFR1 variable domains, for example one such domain linked to only one anti-SA variable domains. In one embodiment, to obtain at alpha, t beta and terminal half-lives or a AUC quoted herein, there is provide an antagonist comprising an anti-TNFR1 immunoglobulin single variable domain linked to PEG, eg, 40-80 kDa PEG, eg, 40 kDa PEG. For example, the antagonist comprises only one such anti-TNFR1 variable domains, for example one such domain linked to 40 kDa PEG.

In one embodiment of the multispecific ligand of the invention, the ligand comprises an anti-SA (eg, HSA) single variable domain that comprises an amino acid sequence that is identical to, or at least 80, 85, 90, 91, 92, 93, 94, 95, 96, 97, 98 or 99% identical to, the sequence of DOM7h-11, DOM7h-11-3, DOM7h-11-12, DOM7h-11-15, DOM7h-14, DOM7h-14-10, DOM7h-14-18 or DOM7m-16 (see WO04003019, WO2008096158 and co-pending patent applications U.S. Ser. No. 61/163,987 and 61/163,990 filed 27 Mar. 2009, the disclosures of which are incorporated herein, including the anti-serum albumin dAb sequences specifically). Alternatively or additionally, in an embodiment, the multispecific ligand comprises a linker provided between the anti-TNFR1 single variable domain and the anti-SA single variable domain, the linker comprising the amino acid sequence AST, optionally ASTSGPS. Alternatively, the linker is $AS(G_4S)_n$, where n is 1, 2, 3, 4, 5, 6, 7 or 8, for example $AS(G_4S)_3$. For example, the ligand comprises (N- to C-terminally) DOM1h-574-16-AST-DOM7h-11; or DOM1h-574-72-ASTSGPS-DOM7m-16; or DOM1h-574-72-ASTSGPS-DOM7h-11-12.

In one aspect, the invention provides a multispecific ligand comprising (i) an anti-TNFα receptor type 1 (TNFR1; p55) immunoglobulin single variable domain which comprises an amino acid sequence that is identical to, or at least 93, 94, 95, 96, 97, 98 or 99% identical to, the amino acid sequence of DOM1h-574-188, DOM1h-574-189, DOM1h-574-190, DOM1h-574-191, DOM1h-574-192, DOM1h-574-193, DOM1h-574-194, DOM1h-574-195, DOM1h-574-196, DOM1h-574-201, DOM1h-574-202, DOM1h-574-203, DOM1h-574-204, DOM1h-574-205, DOM1h-574-206, DOM1h-574-207, DOM1h-574-208, DOM1h-574-209, DOM1h-574-211, DOM1h-574-212, DOM1h-574-213 or DOM1h-574-214, (ii) at least one anti-serum albumin (SA) immunoglobulin single variable domain that specifically binds SA, wherein the anti-SA single variable domain comprises an amino acid sequence that is identical to, or at least 80, 85, 90, 91, 92, 93, 94, 95, 96, 97, 98 or 99% identical to, the sequence of DOM7h-11-3, and (iii) optionally wherein a linker is provided between the anti-TNFR1 single variable domain and the anti-SA single variable domain, the linker comprising the amino acid sequence AST, optionally ASTSGPS. Alternatively, the linker is $AS(G_4S)_n$, where n is 1, 2, 3, 4, 5, 6, 7 or 8, for example $AS(G_4S)_3$. For example, the ligand comprises DOM1h-574-156 and DOM7h-11-3 optionally linked by AST or ASTSGPS. Alternatively, the linker is $AS(G_4S)_n$, where n is 1, 2, 3, 4, 5, 6, 7 or 8, for example $AS(G_4S)_3$. In this example or aspect, the ligand is optionally adapted for administration to a patient by intravascularly, sub-cutaneously, intramuscularly, peritoneally or by inhalation. In one example, the ligand is provided as a dry-powder or lyophilized composition (which optionally is mixed with a diluent prior to administration).

In one aspect, the invention provides a multispecific ligand comprising (i) an anti-TNFα receptor type 1 (TNFR1; p55) immunoglobulin single variable domain which comprises an amino acid sequence that is identical to, or at least 93, 94, 95, 96, 97, 98 or 99% identical to, the amino acid sequence of DOM1h-574-188, DOM1h-574-189, DOM1h-574-190, DOM1h-574-191, DOM1h-574-192, DOM1h-574-193, DOM1h-574-194, DOM1h-574-195, DOM1h-574-196, DOM1h-574-201, DOM1h-574-202, DOM1h-574-203, DOM1h-574-204, DOM1h-574-205, DOM1h-574-206, DOM1h-574-207, DOM1h-574-208, DOM1h-574-209, DOM1h-574-211, DOM1h-574-212, DOM1h-574-213 or DOM1h-574-214, (ii) at least one anti-serum albumin (SA) immunoglobulin single variable domain that specifically binds SA, wherein the anti-SA single variable domain comprises an amino acid sequence that is identical to, or at least 80, 85, 90, 91, 92, 93, 94, 95, 96, 97, 98 or 99% identical to, the sequence of DOM7h-14-10, and (iii) optionally wherein a linker is provided between the anti-TNFR1 single variable domain and the anti-SA single variable domain, the linker comprising the amino acid sequence AST, optionally ASTS- GPS. Alternatively, the linker is AS(G$_4$S)$_n$, where n is 1, 2, 3, 4, 5, 6, 7 or 8, for example AS(G$_4$S)$_3$. In this example or aspect, the ligand is optionally adapted for administration to a patient by intravascularly, sub-cutaneously, intramuscularly, peritoneally or by inhalation. In one example, the ligand is provided as a dry-powder or lyophilized composition (which optionally is mixed with a diluent prior to administration).

The invention provides a TNFR1 antagonist comprising a single variable domain, polypeptide or multispecific ligand of any aspect or embodiment of the invention. For example, the antagonist or variable domain of the invention is monovalent for TNFR1 binding. For example, the antagonist or variable domain of the invention is monovalent or substantially monovalent as determined by standard SEC-MALLS. Substantial monovalency is indicated by no more than 5, 4, 3, 2 or 1% of the variable domain or antagonist being present in a non-monovalent form as determined by standard SEC-MALLS.

In one embodiment, the antagonist of the invention comprises first and second anti-TNFR1 immunoglobulin single variable domains, wherein each variable domain is according to any aspect or embodiment of the invention. The first and second immunoglobulin single variable domains are in one example identical. In another example they are different.

In one example, the antagonist the amino acid sequence of the or each anti-TNFR1 single variable domain in an antagonist of the invention is identical to the amino acid sequence of DOM1h-574-188, DOM1h-574-189, DOM1h-574-190, DOM1h-574-191, DOM1h-574-192, DOM1h-574-193, DOM1h-574-194, DOM1h-574-195, DOM1h-574-196, DOM1h-574-201, DOM1h-574-202, DOM1h-574-203, DOM1h-574-204, DOM1h-574-205, DOM1h-574-206, DOM1h-574-207, DOM1h-574-208, DOM1h-574-209, DOM1h-574-211, DOM1h-574-212, DOM1h-574-213 or DOM1h-574-214.

In one aspect, the invention provides a TNFα receptor type 1 (TNFR1; p55) antagonist comprising an anti-TNFR1 variable domain according any aspect of the invention, for oral delivery, delivery to the GI tract of a patient, pulmonary delivery, delivery to the lung of a patient or systemic delivery. In another aspect, the invention provides the use of the TNFR1 antagonist of any aspect of the invention in the manufacture of a medicament for oral delivery. In another aspect, the invention provides the use of the TNFR1 antagonist of any aspect of the invention in the manufacture of a medicament for delivery to the GI tract of a patient. In one example of the antagonist or the variable domain is resistant to trypsin, elastase and/or pancreatin (see WO2008149143).

In one aspect, the invention provides the use of a TNFR1 antagonist of any aspect of the invention in the manufacture of a medicament for pulmonary delivery. In another aspect, the invention provides the use of a TNFR1 antagonist of any aspect of the invention in the manufacture of a medicament for delivery to the lung of a patient. In one example of the antagonist or the variable domain is resistant to leucozyme.

In one aspect, the invention provides a method of oral delivery or delivery of a medicament to the GI tract of a patient or to the lung or pulmonary tissue of a patient, wherein the method comprises administering to the patient a pharmaceutically effective amount of a TNFR1 antagonist of the invention.

In one aspect, the invention provides a TNFα receptor type 1 (TNFR1; p55) antagonist for binding human, murine or Cynomologus monkey TNFR1, the antagonist having a CDR1 sequence that is identical to, or at least 50, 60, 70, 80, 90, 95 or 98% identical to, the CDR1 sequence of DOM1h-574-188, DOM1h-574-189, DOM1h-574-190, DOM1h-574-191, DOM1h-574-192, DOM1h-574-193, DOM1h-574-194, DOM1h-574-195, DOM1h-574-196, DOM1h-574-201, DOM1h-574-202, DOM1h-574-203, DOM1h-574-204, DOM1h-574-205, DOM1h-574-206, DOM1h-574-207, DOM1h-574-208, DOM1h-574-209, DOM1h-574-211, DOM1h-574-212, DOM1h-574-213 or DOM1h-574-214. Optionally, the antagonist also has a CDR2 sequence that is identical to, or at least 50, 60, 70, 80, 90, 95 or 98% identical to, the CDR2 sequence of the selected sequence. Optionally, additionally or alternatively, the antagonist also has a CDR3 sequence that is identical to, or at least 50, 60, 70, 80, 90, 95 or 98% identical to, the CDR3 sequence of the selected sequence.

In one aspect, the invention provides a TNFα receptor type 1 (TNFR1; p55) antagonist for binding human, murine or Cynomologus monkey TNFR1, the antagonist having a CDR2 sequence that is identical to, or at least 50, 60, 70, 80, 90, 95 or 98% identical to, the CDR2 sequence of DOM1h-574-188, DOM1h-574-189, DOM1h-574-190, DOM1h-574-191, DOM1h-574-192, DOM1h-574-193, DOM1h-574-194, DOM1h-574-195, DOM1h-574-196, DOM1h-574-201, DOM1h-574-202, DOM1h-574-203, DOM1h-574-204, DOM1h-574-205, DOM1h-574-206, DOM1h-574-207, DOM1h-574-208, DOM1h-574-209, DOM1h-574-211, DOM1h-574-212, DOM1h-574-213 or DOM1h-574-214. Optionally, the antagonist also has a CDR3 sequence that is identical to, or at least 50, 60, 70, 80, 90, 95 or 98% identical to, the CDR3 sequence of the selected sequence.

In one aspect, the invention provides a TNFα receptor type 1 (TNFR1; p55) antagonist for binding human, murine or Cynomologus monkey TNFR1, the antagonist having a CDR3 sequence that is identical to, or at least 50, 60, 70, 80, 90, 95 or 98% identical to, the CDR3 sequence of DOM1h-574-188, DOM1h-574-189, DOM1h-574-190, DOM1h-574-191, DOM1h-574-192, DOM1h-574-193, DOM1h-574-194, DOM1h-574-195, DOM1h-574-196, DOM1h-574-201, DOM1h-574-202, DOM1h-574-203, DOM1h-574-204, DOM1h-574-205, DOM1h-574-206, DOM1h-574-207, DOM1h-574-208, DOM1h-574-209, DOM1h-574-211, DOM1h-574-212, DOM1h-574-213 or DOM1h-574-214.

In one aspect, the invention provides a TNFα receptor type 1 (TNFR1; p55) antagonist for binding human, murine or Cynomologus monkey TNFR1, the antagonist comprising an immunoglobulin single variable domain comprising the sequence of CDR1, CDR2, and/or CDR3 of a single variable domain selected from DOM1h-574-188, DOM1h-574-189, DOM1h-574-190, DOM1h-574-191, DOM1h-574-192, DOM1h-574-193, DOM1h-574-194, DOM1h-574-195, DOM1h-574-196, DOM1h-574-201, DOM1h-574-202, DOM1h-574-203, DOM1h-574-204, DOM1h-574-205, DOM1h-574-206, DOM1h-574-207, DOM1h-574-208, DOM1h-574-209, DOM1h-574-211, DOM1h-574-212, DOM1h-574-213 or DOM1h-574-214.

The invention provides the TNFR1 antagonist of any aspect for treating and/or prophylaxis of an inflammatory condition. The invention provides the use of the TNFR1 antagonist of any aspect in the manufacture of a medicament for treating and/or prophylaxis of an inflammatory condition. In one embodiment of the antagonist or use, the condition is selected from the group consisting of arthritis, multiple sclerosis, inflammatory bowel disease and chronic obstructive pulmonary disease. In one example, the arthritis is rheumatoid arthritis or juvenile rheumatoid arthritis. In one example, the inflammatory bowel disease is selected from the group consisting of Crohn's disease and ulcerative colitis. In one example, the chronic obstructive pulmonary disease is selected from the group consisting of chronic bronchitis, chronic obstructive bronchitis and emphysema. In one example, the pneumonia is bacterial pneumonia. In one example, the bacterial pneumonia is Staphylococcal pneumonia.

The invention provides a TNFR1 antagonist of any aspect for treating and/or prophylaxis of a respiratory disease. The invention provides the use of the TNFR1 antagonist of any aspect in the manufacture of a medicament for treating and/or prophylaxis of a respiratory disease. In one example the respiratory disease is selected from the group consisting of lung inflammation, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, non-tuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, and Wegener's granulomatosis.

Polypeptides, dAbs & Antagonists

The polypeptide, ligand, dAb, ligand or antagonist can be expressed in *E. coli* or in *Pichia* species (e.g., *P. pastoris*). In one embodiment, the ligand or dAb monomer is secreted in a quantity of at least about 0.5 mg/L when expressed in *E. coli* or in *Pichia* species (e.g., *P. pastoris*). Although, the ligands and dAb monomers described herein can be secretable when expressed in *E. coli* or in *Pichia* species (e.g., *P. pastoris*), they can be produced using any suitable method, such as synthetic chemical methods or biological production methods that do not employ *E. coli* or *Pichia* species.

In some embodiments, the polypeptide, ligand, dAb, ligand or antagonist does not comprise a Camelid immunoglobulin variable domain, or one or more framework amino acids that are unique to immunoglobulin variable domains encoded by Camelid germline antibody gene segments, eg at position 108, 37, 44, 45 and/or 47. In one embodiment, the anti-TNFR1 variable domain of the invention comprises a G residue at position 44 according to Kabat and optionally comprises one or more Camelid-specific amino acids at other positions, eg at position 37 or 103.

Antagonists of TNFR1 according to the invention can be monovalent or multivalent. In some embodiments, the antagonist is monovalent and contains one binding site that interacts with TNFR1, the binding site provided by a polypeptide or dAb of the invention. Monovalent antagonists bind one TNFR1 and may not induce cross-linking or clustering of TNFR1 on the surface of cells which can lead to activation of the receptor and signal transduction. Monovalent antagonists according to the invention may bind Domain 1, Domain 2, Domain 3 or Domain 4 of TNFR1. In an embodiment, the monovalent antagonist binds Domain 4 of TNFR1. In other embodiments, the monovalent antagonist binds to an epitope which spans more than one Domain of TNFR1. Thus, in one embodiment, the monovalent antagonist may bind to both Domains 1 and 2, Domains 1 and 3, Domains 1 and 4, Domains 2 and 3, Domains 2 and 4, Domains 3 and 4, Domains 1, 2, and 3, Domains 1, 2 and 4, or Domains 1, 3 and 4 of TNFR1.

In other embodiments, the antagonist of TNFR1 is multivalent. Multivalent antagonists of TNFR1 can contain two or more copies of a particular binding site for TNFR1 or contain two or more different binding sites that bind TNFR1, at least one of the binding sites being provided by a polypeptide or dAb of the invention. For example, as described herein the antagonist of TNFR1 can be a dimer, trimer or multimer comprising two or more copies of a particular polypeptide or dAb of the invention that binds TNFR1, or two or more different polypeptides or dAbs of the invention that bind TNFR1. In one embodiment, a multivalent antagonist of TNFR1 does not substantially agonize TNFR1 (act as an agonist of TNFR1) in a standard cell assay (i.e., when present at a concentration of 1 nM, 10 nM, 100 nM, 1 µM, 10 µM, 100 µM, 1000 µM or 5,000 µM, results in no more than about 5% of the TNFR1-mediated activity induced by TNFα (100 pg/ml) in the assay).

In certain embodiments, the multivalent antagonist of TNFR1 contains two or more binding sites for a desired epitope or domain of TNFR1. For example, the multivalent antagonist of TNFR1 can comprise two or more binding sites that bind the same epitope in Domain 1 of TNFR1, or bind the same epitope in Domain 4 of TNFR1.

In other embodiments, the multivalent antagonist of TNFR1 contains two or more binding sites provided by polypeptides or dAbs of the invention that bind to different epitopes or domains of TNFR1. For example, the multivalent antagonists of TNFR1 can comprise binding sites for Domains 1 and 2, Domains 1 and 3, Domains 1 and 4, Domains 2 and 3, Domains 2 and 4, Domains 3 and 4, Domains 1, 2, and 3, Domains 1, 2 and 4, or Domains 1, 3 and 4 of TNFR1. In one embodiment, such multivalent antagonists do not agonize TNFR1 when present at a concentration of about 1 nM, or about 10 nM, or about 100 nM, or about 1 µM, or about 10 µM, in a standard L929 cytotoxicity assay or a standard HeLa IL-8 assay as described in WO2006038027.

Other antagonists of TNFR1 do no inhibit binding of TNFα to TNFR1. Such ligands (and antagonists) may have utility as diagnostic agents, because they can be used to bind and detect, quantify or measure TNFR1 in a sample and will not compete with TNF in the sample for binding to TNFR1. Accordingly, an accurate determination of whether or how much TNFR1 is in the sample can be made.

In other embodiments, the polypeptide, ligand, dAb or antagonist binds TNFR1 and antagonizes the activity of the TNFR1 in a standard cell assay with an $ND_{50}$ of ≤100 nM, and at a concentration of ≤10 µM the dAb agonizes the activity of the TNFR1 by ≤5% in the assay.

In particular embodiments, the polypeptide, ligand, dAb or antagonist does not substantially agonize TNFR1 (act as an agonist of TNFR1) in a standard cell assay (i.e., when present at a concentration of 1 nM, 10 nM, 100 nM, 1 µM, 10 µM, 100 µM, 1000 µM or 5,000 µM, results in no more than about 5% of the TNFR1-mediated activity induced by TNFα (100 pg/ml) in the assay).

In certain embodiments, the polypeptide, ligand, dAb or antagonist of the invention are efficacious in models of chronic inflammatory diseases when an effective amount is administered. Generally an effective amount is about 1 mg/kg to about 10 mg/kg (e.g., about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg). The models of chronic inflammatory disease (see those described in WO2006038027) are recognized by those skilled in the art as being predictive of therapeutic efficacy in humans.

In particular embodiments, the polypeptide, ligand, dAb or antagonist is efficacious in the standard mouse collagen-induced arthritis model (see WO2006038027 for details of the model). For example, administering an effective amount of the polypeptide, ligand, dAb or antagonist can reduce the average arthritic score of the summation of the four limbs in the standard mouse collagen-induced arthritis model, for example, by about 1 to about 16, about 3 to about 16, about 6 to about 16, about 9 to about 16, or about 12 to about 16, as compared to a suitable control. In another example, administering an effective amount of the polypeptide, ligand, dAb or antagonist can delay the onset of symptoms of arthritis in the standard mouse collagen-induced arthritis model, for example, by about 1 day, about 2 days, about 3 days, about 4 days, about 5 days, about 6 days, about 7 days, about 10 days, about 14 days, about 21 days or about 28 days, as compared to a suitable control. In another example, administering an effective amount of the polypeptide, ligand, dAb or antagonist can result in an average arthritic score of the summation of the four limbs in the standard mouse collagen-induced arthritis model of 0 to about 3, about 3 to about 5, about 5 to about 7, about 7 to about 15, about 9 to about 15, about 10 to about 15, about 12 to about 15, or about 14 to about 15.

In other embodiments, the polypeptide, ligand, dAb or antagonist is efficacious in the mouse ΔARE model of arthritis (see WO2006038027 for details of the model). For example, administering an effective amount of the polypeptide, ligand, dAb or antagonist can reduce the average arthritic score in the mouse ΔARE model of arthritis, for example, by about 0.1 to about 2.5, about 0.5 to about 2.5, about 1 to about 2.5, about 1.5 to about 2.5, or about 2 to about 2.5, as compared to a suitable control. In another example, administering an effective amount of the polypeptide, ligand, dAb or antagonist can delay the onset of symptoms of arthritis in the mouse ΔARE model of arthritis by, for example, about 1 day, about 2 days, about 3 days, about 4 days, about 5 days, about 6 days, about 7 days, about 10 days, about 14 days, about 21 days or about 28 days, as compared to a suitable control. In another example, administering an effective amount of the polypeptide, ligand, dAb or antagonist can result in an average arthritic score in the mouse ΔARE model of arthritis of 0 to about 0.5, about 0.5 to about 1, about 1 to about 1.5, about 1.5 to about 2, or about 2 to about 2.5.

In other embodiments, the polypeptide, ligand, dAb or antagonist is efficacious in the mouse ΔARE model of inflammatory bowel disease (IBD) (see WO2006038027 for details of the model). For example, administering an effective amount of the polypeptide, ligand, dAb or antagonist can reduce the average acute and/or chronic inflammation score in the mouse ΔARE model of IBD, for example, by about 0.1 to about 2.5, about 0.5 to about 2.5, about 1 to about 2.5, about 1.5 to about 2.5, or about 2 to about 2.5, as compared to a suitable control. In another example, administering an effective amount of the polypeptide, ligand, dAb or antagonist can delay the onset of symptoms of IBD in the mouse ΔARE model of IBD by, for example, about 1 day, about 2 days, about 3 days, about 4 days, about 5 days, about 6 days, about 7 days, about 10 days, about 14 days, about 21 days or about 28 days, as compared to a suitable control. In another example, administering an effective amount of the polypeptide, ligand, dAb or antagonist can result in an average acute and/or chronic inflammation score in the mouse ΔARE model of IBD of 0 to about 0.5, about 0.5 to about 1, about 1 to about 1.5, about 1.5 to about 2, or about 2 to about 2.5.

In other embodiments, the polypeptide, ligand, dAb or antagonist is efficacious in the mouse dextran sulfate sodium (DSS) induced model of IBD (see WO2006038027 for details of the model). For example, administering an effective amount of the polypeptide, ligand, dAb or antagonist can reduce the average severity score in the mouse DSS model of IBD, for example, by about 0.1 to about 2.5, about 0.5 to about 2.5, about 1 to about 2.5, about 1.5 to about 2.5, or about 2 to about 2.5, as compared to a suitable control. In another example, administering an effective amount of the polypeptide, ligand, dAb or antagonist can delay the onset of symptoms of IBD in the mouse DSS model of IBD by, for example, about 1 day, about 2 days, about 3 days, about 4 days, about 5 days, about 6 days, about 7 days, about 10 days, about 14 days, about 21 days or about 28 days, as compared to a suitable control. In another example, administering an effective amount of the polypeptide, ligand, dAb or antagonist can result in an average severity score in the mouse DSS model of IBD of 0 to about 0.5, about 0.5 to about 1, about 1 to about 1.5, about 1.5 to about 2, or about 2 to about 2.5.

In particular embodiments, the polypeptide, ligand, dAb or antagonist is efficacious in the mouse tobacco smoke model of chronic obstructive pulmonary disease (COPD) (see WO2006038027 and WO2007049017 for details of the model). For example, administering an effective amount of the ligand can reduce or delay onset of the symptoms of COPD, as compared to a suitable control.

Animal model systems which can be used to screen the effectiveness of the antagonists of TNFR1 (e.g, ligands, antibodies or binding proteins thereof) in protecting against or treating the disease are available. Methods for the testing of systemic lupus erythematosus (SLE) in susceptible mice are known in the art (Knight et al. (1978) *J. Exp. Med.*, 147: 1653; Reinersten et al. (1978) *New Eng. J. Med.*, 299: 515). Myasthenia Gravis (MG) is tested in SJL/J female mice by inducing the disease with soluble AchR protein from another species (Lindstrom et al. (1988) *Adv. Immunol.*, 42: 233). Arthritis is induced in a susceptible strain of mice by injection of Type II collagen (Stuart et al. (1984) *Ann. Rev. Immunol.*, 42: 233). A model by which adjuvant arthritis is induced in susceptible rats by injection of mycobacterial heat shock protein has been described (Van Eden et al. (1988) *Nature*, 331: 171). Thyroiditis is induced in mice by administration of thyroglobulin as described (Maron et al. (1980) *J. Exp. Med.*, 152: 1115). Insulin dependent diabetes mellitus (IDDM) occurs naturally or can be induced in certain strains of mice such as those described by Kanasawa et al. (1984) *Diabetologia*, 27: 113. EAE in mouse and rat serves as a model for MS in human. In this model, the demyelinating disease is induced by administration of myelin basic protein (see Paterson (1986) *Textbook of Immunopathology*, Mischer et al., eds., Grune and Stratton, New York, pp. 179-213; McFarlin et al. (1973) *Science*, 179: 478: and Satoh et al. (1987) *J. Immunol.*, 138: 179).

Generally, the present ligands (e.g., antagonists) will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) *Remington's Pharmaceutical Sciences,* 16th Edition). A variety of suitable formulations can be used, including extended release formulations.

The ligands (e.g., antagonits) of the present invention may be used as separately administered compositions or in conjunction with other agents. These can include various immunotherapeutic drugs, such as cylcosporine, methotrexate, adriamycin or cisplatinum, and immunotoxins. Pharmaceutical compositions can include "cocktails" of various cytotoxic or other agents in conjunction with the ligands of the present invention, or even combinations of ligands according to the present invention having different specificities, such as ligands selected using different target antigens or epitopes, whether or not they are pooled prior to administration.

The route of administration of pharmaceutical compositions according to the invention may be any of those commonly known to those of ordinary skill in the art. For therapy, including without limitation immunotherapy, the selected ligands thereof of the invention can be administered to any patient in accordance with standard techniques.

The administration can be by any appropriate mode, including parenterally, intravenously, intramuscularly, intraperitoneally, subcutaneously, transdermally, via the pulmonary route, or also, appropriately, by direct infusion with a catheter. The dosage and frequency of administration will depend on the age, sex and condition of the patient, concurrent administration of other drugs, counter indications and other parameters to be taken into account by the clinician. Administration can be local (e.g., local delivery to the lung by pulmonary administration, e.g., intranasal administration) or systemic as indicated.

The ligands of this invention can be lyophilised for storage and reconstituted in a suitable carrier prior to use. This technique has been shown to be effective with conventional immunoglobulins and art-known lyophilisation and reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate.

The compositions containing the present ligands (e.g., antagonists) or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 10.0 mg of ligand, e.g. dAb or antagonist per kilogram of body weight, with doses of 0.05 to 2.0 mg/kg/dose being more commonly used. For prophylactic applications, compositions containing the present ligands or cocktails thereof may also be administered in similar or slightly lower dosages, to prevent, inhibit or delay onset of disease (e.g., to sustain remission or quiescence, or to prevent acute phase). The skilled clinician will be able to determine the appropriate dosing interval to treat, suppress or prevent disease. When an ligand of TNFR1 (e.g., antagonist) is administered to treat, suppress or prevent a chronic inflammatory disease, it can be administered up to four times per day, twice weekly, once weekly, once every two weeks, once a month, or once every two months, at a dose off, for example, about 10 µg/kg to about 80 mg/kg, about 100 µg/kg to about 80 mg/kg, about 1 mg/kg to about 80 mg/kg, about 1 mg/kg to about 70 mg/kg, about 1 mg/kg to about 60 mg/kg, about 1 mg/kg to about 50 mg/kg, about 1 mg/kg to about 40 mg/kg, about 1 mg/kg to about 30 mg/kg, about 1 mg/kg to about 20 mg/kg, about 1 mg/kg to about 10 mg/kg, about 10 µg/kg to about 10 mg/kg, about 10 µg/kg to about 5 mg/kg, about 10 µg/kg to about 2.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg or about 10 mg/kg. In particular embodiments, the ligand of TNFR1 (e.g., antagonist) is administered to treat, suppress or prevent a chronic inflammatory disease once every two weeks or once a month at a dose of about 10 mg/kg to about 10 mg/kg (e.g., about 10 mg/kg, about 100 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg or about 10 mg/kg.)

Treatment or therapy performed using the compositions described herein is considered "effective" if one or more symptoms are reduced (e.g., by at least 10% or at least one point on a clinical assessment scale), relative to such symptoms present before treatment, or relative to such symptoms in an individual (human or model animal) not treated with such composition or other suitable control. Symptoms will obviously vary depending upon the disease or disorder targeted, but can be measured by an ordinarily skilled clinician or technician. Such symptoms can be measured, for example, by monitoring the level of one or more biochemical indicators of the disease or disorder (e.g., levels of an enzyme or metabolite correlated with the disease, affected cell numbers, etc.), by monitoring physical manifestations (e.g., inflammation, tumor size, etc.), or by an accepted clinical assessment scale, for example, the Expanded Disability Status Scale (for multiple sclerosis), the Irvine Inflammatory Bowel Disease Questionnaire (32 point assessment evaluates quality of life with respect to bowel function, systemic symptoms, social function and emotional status—score ranges from 32 to 224, with higher scores indicating a better quality of life), the Quality of Life Rheumatoid Arthritis Scale, or other accepted clinical assessment scale as known in the field. A sustained (e.g., one day or more, or longer) reduction in disease or disorder symptoms by at least 10% or by one or more points on a given clinical scale is indicative of "effective" treatment. Similarly, prophylaxis performed using a composition as described herein is "effective" if the onset or severity of one or more symptoms is delayed, reduced or abolished relative to such symptoms in a similar individual (human or animal model) not treated with the composition.

A composition containing a ligand (e.g., antagonist) or cocktail thereof according to the present invention may be utilised in prophylactic and therapeutic settings to aid in the alteration, inactivation, killing or removal of a select target cell population in a mammal. In addition, the selected repertoires of polypeptides described herein may be used extracorporeally or in vitro selectively to kill, deplete or otherwise effectively remove a target cell population from a heterogeneous collection of cells. Blood from a mammal may be combined extracorporeally with the ligands whereby the undesired cells are killed or otherwise removed from the blood for return to the mammal in accordance with standard techniques.

A composition containing a ligand (e.g., antagonist) according to the present invention may be utilised in prophylactic and therapeutic settings to aid in the alteration, inactivation, killing or removal of a select target cell population in a mammal.

The ligands (e.g., anti-TNFR1 antagonists, dAb monomers) can be administered and or formulated together with one or more additional therapeutic or active agents. When a ligand (eg, a dAb) is administered with an additional therapeutic agent, the ligand can be administered before, simultaneously with or subsequent to administration of the additional agent. Generally, the ligand and additional agent are administered in a manner that provides an overlap of therapeutic effect.

In one embodiment, the invention is a method for treating, suppressing or preventing a chronic inflammatory disease, comprising administering to a mammal in need thereof a therapeutically-effective dose or amount of a polypeptide, ligand, dAb or antagonist of TNFR1 according to the invention.

In one embodiment, the invention is a method for treating, suppressing or preventing arthritis (e.g., rheumatoid arthritis, juvenile rheumatoid arthritis, ankylosing spondylitis, psoriatic arthritis) comprising administering to a mammal in need thereof a therapeutically-effective dose or amount of a polypeptide, ligand, dAb or antagonist of TNFR1 according to the invention.

In another embodiment, the invention is a method for treating, suppressing or preventing psoriasis comprising administering to a mammal in need thereof a therapeutically-effective dose or amount of a polypeptide, ligand, dAb or antagonist of TNFR1 according to the invention.

In another embodiment, the invention is a method for treating, suppressing or preventing inflammatory bowel disease (e.g., Crohn's disease, ulcerative colitis) comprising administering to a mammal in need thereof a therapeutically-effective dose or amount of a polypeptide, ligand, dAb or antagonist of TNFR1 according to the invention.

In another embodiment, the invention is a method for treating, suppressing or preventing chronic obstructive pulmonary disease (e.g., chronic bronchitis, chronic obstructive bronchitis, emphysema), comprising administering to a mammal in need thereof a therapeutically-effective dose or amount of a polypeptide, ligand, dAb or antagonist of TNFR1 according to the invention.

In another embodiment, the invention is a method for treating, suppressing or preventing pneumonia (e.g., bacterial pneumonia, such as Staphylococcal pneumonia) comprising administering to a mammal in need thereof a therapeutically-effective dose or amount of a polypeptide, ligand, dAb or antagonist of TNFR1 according to the invention.

The invention provides a method for treating, suppressing or preventing other pulmonary diseases in addition to chronic obstructive pulmonary disease, and pneumonia. Other pulmonary diseases that can be treated, suppressed or prevented in accordance with the invention include, for example, cystic fibrosis and asthma (e.g., steroid resistant asthma). Thus, in another embodiment, the invention is a method for treating, suppressing or preventing a pulmonary disease (e.g., cystic fibrosis, asthma) comprising administering to a mammal in need thereof a therapeutically-effective dose or amount of a polypeptide, ligand, dAb or antagonist of TNFR1 according to the invention.

In particular embodiments, an antagonist of TNFR1 is administered via pulmonary delivery, such as by inhalation (e.g., intrabronchial, intranasal or oral inhalation, intranasal drops) or by systemic delivery (e.g., parenteral, intravenous, intramuscular, intraperitoneal, subcutaneous).

In another embodiment, the invention is a method treating, suppressing or preventing septic shock comprising administering to a mammal in need thereof a therapeutically-effective dose or amount of a polypeptide, ligand, dAb or antagonist of TNFR1 according to the invention.

In a further aspect of the invention, there is provided a composition comprising a a polypeptide, ligand, dAb or antagonist of TNFR1 according to the invention and a pharmaceutically acceptable carrier, diluent or excipient.

Moreover, the present invention provides a method for the treatment of disease using a polypeptide, ligand, dAb or antagonist of TNFR1 or a composition according to the present invention. In an embodiment the disease is cancer or an inflammatory disease, eg rheumatoid arthritis, asthma or Crohn's disease.

In a further aspect of the invention, there is provided a composition comprising a polypeptide, single variable domain, ligand or antagonist according to the invention and a pharmaceutically acceptable carrier, diluent or excipient.

In particular embodiments, the polypeptide, ligand, single variable domain, antagonist or composition is administered via pulmonary delivery, such as by inhalation (e.g, intrabronchial, intranasal or oral inhalation, intranasal drops) or by systemic delivery (e.g, parenteral, intravenous, intramuscular, intraperitoneal, subcutaneous).

An aspect of the invention provides a pulmonary delivery device containing a polypeptide, single variable domain, ligand, composition or antagonist according to the invention. The device can be an inhaler or an intranasal administration device.

In other embodiments, any of the ligands described herein (eg., antagonist or single variable domain) further comprises a half-life extending moiety, such as a polyalkylene glycol moiety, serum albumin or a fragment thereof, transferrin receptor or a transferrin-binding portion thereof, or a moiety comprising a binding site for a polypeptide that enhance half-life in vivo. In some embodiments, the half-life extending moiety is a moiety comprising a binding site for a polypeptide that enhances half-life in vivo selected from the group consisting of an affibody, a SpA domain, an LDL receptor class A domain, an EGF domain, and an avimer.

In other embodiments, the half-life extending moiety is a polyethylene glycol moiety. In one embodiment, the antagonist comprises (optionally consists of) a single variable domain of the invention linked to a polyethylene glycol moiety (optionally, wherein the moiety has a size of about 20 to about 50 kDa, optionally about 40 kDa linear or branched PEG). Reference is made to WO04081026 for more detail on PEGylation of dAbs and binding moieties. In one embodiment, the antagonist consists of a dAb monomer linked to a PEG, wherein the dAb monomer is a single variable domain according to the invention. This antagonist can be provided for treatment of inflammatory disease, a lung condition (e.g., asthma, influenza or COPD) or cancer or optionally is for intravenous administration.

In other embodiments, the half-life extending moiety is an antibody or antibody fragment (e.g, an immunoglobulin single variable domain) comprising a binding site for serum albumin or neonatal Fc receptor.

The invention also relates to a composition (e.g, pharmaceutical composition) comprising a ligand of the invention (eg., antagonist, or single variable domain) and a physiologically acceptable carrier. In some embodiments, the composition comprises a vehicle for intravenous, intramuscular, intraperitoneal, intraarterial, intrathecal, intraarticular, subcutaneous administration, pulmonary, intranasal, vaginal, or rectal administration.

The invention also relates to a drug delivery device comprising the composition (e.g, pharmaceutical composition) of the invention. In some embodiments, the drug delivery device comprises a plurality of therapeutically effective doses of ligand. In other embodiments, the drug delivery device is selected from the group consisting of parenteral delivery device, intravenous delivery device, intramuscular delivery device, intraperitoneal delivery device, transdermal delivery device, pulmonary delivery device, intraarterial delivery device, intrathecal delivery device, intraarticular delivery device, subcutaneous delivery device, intranasal delivery device, vaginal delivery device, rectal delivery device, syringe, a transdermal delivery device, a capsule, a tablet, a nebulizer, an inhaler, an atomizer, an aerosolizer, a mister, a dry powder inhaler, a metered dose inhaler, a metered dose sprayer, a metered dose mister, a metered dose atomizer, and a catheter.

The ligand (eg, single variable domain, antagonist or multispecific ligand) of the invention can be formatted as described herein. For example, the ligand of the invention can be formatted to tailor in vivo serum half-life. If desired, the ligand can further comprise a toxin or a toxin moiety as described herein. In some embodiments, the ligand comprises a surface active toxin, such as a free radical generator (e.g., selenium containing toxin) or a radionuclide. In other embodiments, the toxin or toxin moiety is a polypeptide domain (e.g, a dAb) having a binding site with binding specificity for an intracellular target. In particular embodiments, the ligand is an IgG-like format that has binding specificity for TNFR1 (e.g. human TNFR1).

In an aspect, the invention provides a fusion protein comprising the single variable domain of the invention. The variable domain can be fused, for example, to a peptide or polypeptide or protein. In one embodiment, the variable domain is fused to an antibody or antibody fragment, eg a monoclonal antibody. Generally, fusion can be achieved by expressing the fusion product from a single nucleic acid sequence or by expressing a polypeptide comprising the single variable domain and then assembling this polypeptide into a larger protein or antibody format using techniques that are conventional.

In one embodiment, the immunoglobulin single variable domain, antagonist or the fusion protein comprises an antibody constant domain. In one embodiment, the immunoglobulin single variable domain, antagonist or the fusion protein comprises an antibody Fc, optionally wherein the N-terminus of the Fc is linked (optionally directly linked) to the C-terminus of the variable domain. In one embodiment, the immunoglobulin single variable domain, antagonist or the fusion protein comprises a half-life extending moiety. The half-life extending moiety can be a polyethylene glycol moiety, serum albumin or a fragment thereof, transferrin receptor or a transferrin-binding portion thereof, or an antibody or antibody fragment comprising a binding site for a polypeptide that enhances half-life in vivo. The half-life extending moiety can be an antibody or antibody fragment comprising a binding site for serum albumin or neonatal Fc receptor. The half-life extending moiety can be a dAb, antibody or antibody fragment. In one embodiment, the immunoglobulin single variable domain or the antagonist or the fusion protein is provided such that the variable domain (or the variable domain comprised by the antagonist or fusion protein) further comprises a polyalkylene glycol moiety. The polyalkylene glycol moiety can be a polyethylene glycol moiety. Further discussion is provided below.

Reference is made to WO2006038027, which discloses anti-TNFR1 immunoglobulin single variable domains. The disclosure of this document is incorporated herein in its entirety, in particular to provide for uses, formats, methods of selection, methods of production, methods of formulation and assays for anti-TNFR1 single variable domains, ligands, antagonists and the like, so that these disclosures can be applied specifically and explicitly in the context of the present invention, including to provide explicit description for importation into claims of the present disclosure.

The anti-TNFR1 of the invention is an immunoglobulin single variable domain that optionally is a human variable domain or a variable domain that comprises or are derived from human framework regions (e.g., DP47 or DPK9 framework regions). In certain embodiments, the variable domain is based on a universal framework, as described herein.

In certain embodiments, a polypeptide domain (e.g., immunoglobulin single variable domain) that has a binding site with binding specificity for TNFR1 resists aggregation, unfolds reversibly (see WO04101790, the teachings of which are incorporated herein by reference).

Nucleic Acid Molecules, Vectors and Host Cells

The invention also provides isolated and/or recombinant nucleic acid molecules encoding ligands (single variable domains, fusion proteins, polypeptides, dual-specific ligands and multispecific ligands) as described herein.

In one aspect, the invention provides an isolated or recombinant nucleic acid encoding a polypeptide comprising an immunoglobulin single variable domain according to the invention. In one embodiment, the nucleic acid comprises the nucleotide sequence of DOM1h-574-188, DOM1h-574-189, DOM1h-574-190, DOM1h-574-191, DOM1h-574-192, DOM1h-574-193, DOM1h-574-194, DOM1h-574-195, DOM1h-574-196, DOM1h-574-201, DOM1h-574-202, DOM1h-574-203, DOM1h-574-204, DOM1h-574-205, DOM1h-574-206, DOM1h-574-207, DOM1h-574-208, DOM1h-574-209, DOM1h-574-211, DOM1h-574-212, DOM1h-574-213 or DOM1h-574-214. In one aspect, the invention provides an isolated or recombinant nucleic acid, wherein the nucleic acid comprises a nucleotide sequence that is at least 80, 85, 90, 95, 98 or 99% identical to the nucleotide sequence of DOM1h-574-188, DOM1h-574-189, DOM1h-574-190, DOM1h-574-191, DOM1h-574-192, DOM1h-574-193, DOM1h-574-194, DOM1h-574-195, DOM1h-574-196, DOM1h-574-201, DOM1h-574-202, DOM1h-574-203, DOM1h-574-204, DOM1h-574-205, DOM1h-574-206, DOM1h-574-207, DOM1h-574-208, DOM1h-574-209, DOM1h-574-211, DOM1h-574-212, DOM1h-574-213 or DOM1h-574-214 and wherein the nucleic acid encodes a polypeptide comprising an immunoglobulin single variable domain that specifically binds to TNFR1. In one aspect, the invention provides an isolated or recombinant nucleic acid, wherein the nucleic acid comprises a nucleotide sequence that is at least 80, 85, 90, 95, 98 or 99% identical to the nucleotide sequence of DOM1h-574-188, DOM1h-574-189, DOM1h-574-190, DOM1h-574-191, DOM1h-574-192, DOM1h-574-193, DOM1h-574-194, DOM1h-574-195, DOM1h-574-196, DOM1h-574-201, DOM1h-574-202, DOM1h-574-203, DOM1h-574-204, DOM1h-574-205, DOM1h-574-206, DOM1h-574-207, DOM1h-574-208, DOM1h-574-209, DOM1h-574-211, DOM1h-574-212, DOM1h-574-213 or DOM1h-574-214 and wherein the nucleic acid encodes a polypeptide comprising an immunoglobulin single variable domain that specifically binds to TNFR1. In one aspect, the invention provides an isolated or recombinant nucleic acid, wherein the nucleic acid comprises a nucleotide sequence that is at least 80, 85, 90, 95, 98 or 99% identical to the nucleotide sequence of DOM1h-574-188, DOM1h-574-189, DOM1h-574-190, DOM1h-574-191, DOM1h-574-192, DOM1h-574-193, DOM1h-574-194, DOM1h-574-195, DOM1h-574-196, DOM1h-574-201, DOM1h-574-202, DOM1h-574-203, DOM1h-574-204, DOM1h-574-205, DOM1h-574-206, DOM1h-574-207, DOM1h-574-208, DOM1h-574-209, DOM1h-574-211, DOM1h-574-212, DOM1h-574-213 or DOM1h-574-214 and wherein the nucleic acid encodes a polypeptide comprising an immunoglobulin single variable domain that specifically binds to TNFR1. In one aspect, the invention provides an isolated or recombinant nucleic acid, wherein the nucleic acid comprises a nucleotide sequence that is at least 80, 85, 90, 95, 98 or 99% identical to the nucleotide sequence of DOM1h-574-188, DOM1h-574-189, DOM1h-574-190, DOM1h-574-191, DOM1h-574-192, DOM1h-574-193, DOM1h-574-194, DOM1h-574-195, DOM1h-574-196, DOM1h-574-201, DOM1h-574-202, DOM1h-574-203, DOM1h-574-204, DOM1h-574-205, DOM1h-574-206, DOM1h-574-207, DOM1h-574-208, DOM1h-574-209, DOM1h-574-211, DOM1h-574-212, DOM1h-574-213 or DOM1h-574-214 and wherein the nucleic acid encodes a polypeptide comprising an immunoglobulin single variable domain that specifically binds to TNFR1.

In one aspect, the invention provides a vector comprising a nucleic acid of the invention. In one aspect, the invention provides a host cell comprising a nucleic acid of the invention or the vector. There is provided a method of producing polypeptide comprising an immunoglobulin single variable domain, the method comprising maintaining the host cell under conditions suitable for expression of the nucleic acid or vector, whereby a polypeptide comprising an immunoglobulin single variable domain is produced. Optionally, the method further comprises the step of isolating the polypeptide and optionally producing a variant, eg a mutated variant, having an improved affinity (KD); $ND_{50}$ for TNFR1 neutralization in a standard MRC5, L929 or Cynomologus KI assay than the isolated polypeptide.

Nucleic acids referred to herein as "isolated" are nucleic acids which have been separated away from the nucleic acids of the genomic DNA or cellular RNA of their source of origin (e.g., as it exists in cells or in a mixture of nucleic acids such as a library), and include nucleic acids obtained by methods described herein or other suitable methods, including essentially pure nucleic acids, nucleic acids produced by chemical synthesis, by combinations of biological and chemical methods, and recombinant nucleic acids which are isolated (see e.g., Daugherty, B. L. et al., *Nucleic Acids Res.,* 19(9): 2471-2476 (1991); Lewis, A. P. and J. S. Crowe, *Gene,* 101: 297-302 (1991)).

Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes.

In certain embodiments, the isolated and/or recombinant nucleic acid comprises a nucleotide sequence encoding a ligand, as described herein, wherein the ligand comprises an amino acid sequence that has at least about 80%, at least about 85%, at least about 90%, at least about 91%, at least about 92%, at least about 93%, at least about 94%, at least about 95%, at least about 96%, at least about 97%, at least about 98%, or at least about 99% amino acid sequence identity with the amino acid sequence of a dAb that binds TNFR1 disclosed herein, eg, DOM1h-574-188, DOM1h-574-189, DOM1h-574-190, DOM1h-574-191, DOM1h-574-192, DOM1h-574-193, DOM1h-574-194, DOM1h-574-195, DOM1h-574-196, DOM1h-574-201, DOM1h-574-202, DOM1h-574-203, DOM1h-574-204, DOM1h-574-205, DOM1h-574-206, DOM1h-574-207, DOM1h-574-208, DOM1h-574-209, DOM1h-574-211, DOM1h-574-212, DOM1h-574-213 or DOM1h-574-214. Nucleotide sequence identity can be determined over the whole length of the nucleotide sequence that encodes the selected anti-TNFR1 dAb.

The invention also provides a vector comprising a recombinant nucleic acid molecule of the invention. In certain embodiments, the vector is an expression vector comprising one or more expression control elements or sequences that are operably linked to the recombinant nucleic acid of the invention The invention also provides a recombinant host cell comprising a recombinant nucleic acid molecule or vector of the invention. Suitable vectors (e.g, plasmids, phagmids), expression control elements, host cells and methods for producing recombinant host cells of the invention are well-known in the art, and examples are further described herein.

Suitable expression vectors can contain a number of components, for example, an origin of replication, a selectable marker gene, one or more expression control elements, such as a transcription control element (e.g, promoter, enhancer, terminator) and/or one or more translation signals, a signal sequence or leader sequence, and the like. Expression control elements and a signal sequence, if present, can be provided by the vector or other source. For example, the transcriptional and/or translational control sequences of a cloned nucleic acid encoding an antibody chain can be used to direct expression.

A promoter can be provided for expression in a desired host cell. Promoters can be constitutive or inducible. For example, a promoter can be operably linked to a nucleic acid encoding an antibody, antibody chain or portion thereof, such that it directs transcription of the nucleic acid. A variety of suitable promoters for prokaryotic (e.g, lac, tac, T3, T7 promoters for *E. coli*) and eukaryotic (e.g, Simian Virus 40 early or late promoter, Rous sarcoma virus long terminal repeat promoter, cytomegalovirus promoter, adenovirus late promoter) hosts are available.

In addition, expression vectors typically comprise a selectable marker for selection of host cells carrying the vector, and, in the case of a replicable expression vector, an origin of replication. Genes encoding products which confer antibiotic or drug resistance are common selectable markers and may be used in prokaryotic (e.g, lactamase gene (ampicillin resistance), Tet gene for tetracycline resistance) and eukaryotic cells (e.g, neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g, LEU2, URA3, HIS3) are often used as selectable markers in yeast. Use of viral (e.g, baculovirus) or phage vectors, and vectors which are capable of integrating into the genome of the host cell, such as retroviral vectors, are also contemplated. Suitable expression vectors for expression in mammalian cells and prokaryotic cells (*E. coli*), insect cells (*Drosophila* Schnieder S2 cells, Sf9) and yeast (*P. methanolica, P. pastoris, S. cerevisiae*) are well-known in the art.

Suitable host cells can be prokaryotic, including bacterial cells such as *E. coli, B. subtilis* and/or other suitable bacteria; eukaryotic cells, such as fungal or yeast cells (e.g., *Pichia pastoris, Aspergillus* sp., *Saccharomyces cerevisiae, Schizosaccharomyces pombe, Neurospora crassa*), or other lower eukaryotic cells, and cells of higher eukaryotes such as those from insects (e.g., *Drosophila* Schnieder S2 cells, Sf9 insect cells (WO 94/26087 (O'Connor)), mammals (e.g., COS cells, such as COS-1 (ATCC Accession No. CRL-1650) and COS-7 (ATCC Accession No. CRL-1651), CHO (e.g., ATCC Accession No. CRL-9096, CHO DG44 (Urlaub, G. and Chasin, L A., *Proc. Natl. Acac. Sci. USA,* 77(7):4216-4220 (1980))), 293 (ATCC Accession No. CRL-1573), HeLa (ATCC Accession No. CCL-2), CV1 (ATCC Accession No. CCL-70), WOP (Dailey, L., et al., *J. Virol.,* 54:739-749 (1985), 3T3, 293T (Pear, W. S., et al., *Proc. Natl. Acad. Sci. U.S.A.,* 90:8392-8396 (1993)) NS0 cells, SP2/0, HuT 78 cells and the like, or plants (e.g., tobacco). (See, for example, Ausubel, F. M. et al., eds. *Current Protocols in Molecular Biology,* Greene Publishing Associates and John Wiley & Sons Inc. (1993).) In some embodiments, the host cell is an isolated host cell and is not part of a multicellular organism (e.g., plant or animal). In certain embodiments, the host cell is a non-human host cell.

The invention also provides a method for producing a ligand (e.g, dual-specific ligand, multispecific ligand) of the invention, comprising maintaining a recombinant host cell comprising a recombinant nucleic acid of the invention under conditions suitable for expression of the recombinant nucleic acid, whereby the recombinant nucleic acid is expressed and a ligand is produced. In some embodiments, the method further comprises isolating the ligand.

Reference is made to WO2006038027, for details of disclosure that is applicable to embodiments of the present invention. For example, relevant disclosure relates to the preparation of immunoglobulin single variable domain-based ligands, library vector systems, library construction, combining single variable domains, characterisation of ligands, structure of ligands, skeletons, protein scaffolds, diversification of the canonical sequence, assays and therapeutic and diagnostic compositions and uses, as well as definitions of "operably linked", "naive", "prevention", "suppression", "treatment" and "therapeutically-effective dose".

Formats

Increased half-life is useful in in vivo applications of immunoglobulins, especially antibodies and most especially antibody fragments of small size. Such fragments (Fvs, disulphide bonded Fvs, Fabs, scFvs, dAbs) suffer from rapid clearance from the body; thus, whilst they are able to reach most parts of the body rapidly, and are quick to produce and easier to handle, their in vivo applications have been limited by their only brief persistence in vivo. One embodiment of the invention solves this problem by providing increased half-life of the ligands in vivo and consequently longer persistence times in the body of the functional activity of the ligand. Methods for pharmacokinetic analysis and determination of ligand half-life will be familiar to those skilled in the art. Details may be found in Kenneth, A et al: Chemical Stability of Pharmaceuticals: A Handbook for Pharmacists and in Peters et al, Pharmacokinetic analysis: A Practical Approach (1996). Reference is also made to "Pharmacokinetics", M Gibaldi & D Perron, published by Marcel Dekker, $2^{nd}$ Rev. ex edition (1982), which describes pharmacokinetic parameters such as t alpha and t beta half lives and area under the curve (AUC). Half-life and AUC definitions are provided above.

In one embodiment, the present invention provides a ligand (eg, polypeptide, variable domain, antagonist, multispecific ligand) or a composition comprising a ligand according to the invention having a tα half-life in the range of 15 minutes or more. In one embodiment, the lower end of the range is 30 minutes, 45 minutes, 1 hour, 2 hours, 3 hours, 4 hours, 5 hours, 6 hours, 7 hours, 10 hours, 11 hours or 12 hours. In addition, or alternatively, a ligand or composition according to the invention will have a tα half life in the range of up to and including 12 hours. In one embodiment, the upper end of the range is 11, 10, 9, 8, 7, 6 or 5 hours. An example of a suitable range is 1 to 6 hours, 2 to 5 hours or 3 to 4 hours.

In one embodiment, the present invention provides a ligand (eg, polypeptide, variable domain, antagonist, multispecific ligand) or a composition comprising a ligand according to the invention having a tβ half-life in the range of about 2.5 hours or more. In one embodiment, the lower end of the range is about 3 hours, about 4 hours, about 5 hours, about 6 hours, about 7 hours, about 10 hours, about 11 hours, or about 12 hours. In addition, or alternatively, a ligand or composition according to the invention has a tβ half-life in the range of up to and including 21 days. In one embodiment, the upper end of the range is about 12 hours, about 24 hours, about 2 days, about 3 days, about 5 days, about 10 days, about 15 days or about 20 days. In one embodiment a ligand or composition according to the invention will have a tβ half life in the range about 12 to about 60 hours. In a further embodiment, it will be in the range about 12 to about 48 hours. In a further embodiment still, it will be in the range about 12 to about 26 hours.

In addition, or alternatively to the above criteria, the present invention provides a ligand or a composition comprising a ligand according to the invention having an AUC value (area under the curve) in the range of about 1 mg·min/ml or more. In one embodiment, the lower end of the range is about 5, about 10, about 15, about 20, about 30, about 100, about 200 or about 300 mg·min/ml. In addition, or alternatively, a ligand or composition according to the invention has an AUC in the range of up to about 600 mg·min/ml. In one embodiment, the upper end of the range is about 500, about 400, about 300, about 200, about 150, about 100, about 75 or about 50 mg·min/ml. In one embodiment a ligand according to the invention will have a AUC in the range selected from the group consisting of the following: about 15 to about 150 mg·min/ml, about 15 to about 100 mg·min/ml, about 15 to about 75 mg·min/ml, and about 15 to about 50 mg·min/ml.

Polypeptides and dAbs of the invention and antagonists comprising these can be formatted to have a larger hydrodynamic size, for example, by attachment of a PEG group, serum albumin, transferrin, transferrin receptor or at least the transferrin-binding portion thereof, an antibody Fc region, or by conjugation to an antibody domain. For example, polypeptides dAbs and antagonists formatted as a larger antigen-binding fragment of an antibody or as an antibody (e.g, formatted as a Fab, Fab', F(ab)$_2$, F(ab')$_2$, IgG, scFv).

Hydrodynamic size of the ligands (e.g, dAb monomers and multimers) of the invention may be determined using methods which are well known in the art. For example, gel filtration chromatography may be used to determine the hydrodynamic size of a ligand. Suitable gel filtration matrices for determining the hydrodynamic sizes of ligands, such as cross-linked agarose matrices, are well known and readily available.

The size of a ligand format (e.g, the size of a PEG moiety attached to a dAb monomer), can be varied depending on the desired application. For example, where ligand is intended to leave the circulation and enter into peripheral tissues, it is desirable to keep the hydrodynamic size of the ligand low to facilitate extravazation from the blood stream. Alternatively, where it is desired to have the ligand remain in the systemic circulation for a longer period of time the size of the ligand can be increased, for example by formatting as an Ig like protein.

Half-Life Extension by Targeting an Antigen or Epitope that Increases Half-Live In Vivo The hydrodynamic size of a ligand and its serum half-life can also be increased by conjugating or associating an TNFR1 binding polypeptide, dAb or antagonist of the invention to a binding domain (e.g, antibody or antibody fragment) that binds an antigen or epitope that increases half-live in vivo, as described herein. For example, the TNFR1 binding agent (e.g, polypeptide) can be conjugated or linked to an anti-serum albumin or anti-neonatal Fc receptor antibody or antibody fragment, eg an anti-SA or anti-neonatal Fc receptor dAb, Fab, Fab' or scFv, or to an anti-SA affibody or anti-neonatal Fc receptor Affibody or an anti-SA avimer, or an anti-SA binding domain which comprises a scaffold selected from, but not limited to, the group consisting of CTLA-4, lipocallin, SpA, an affibody, an avimer, GroE1 and fibronectin (see WO2008096158 for disclosure of these binding domains, which domains and their sequences are incorporated herein by reference and form part of the disclosure of the present text). Conjugating refers to a composition comprising polypeptide, dAb or antagonist of the invention that is bonded (covalently or noncovalently) to a binding domain that binds serum albumin.

Suitable polypeptides that enhance serum half-life in vivo include, for example, transferrin receptor specific ligand-neuropharmaceutical agent fusion proteins (see U.S. Pat. No. 5,977,307, the teachings of which are incorporated herein by reference), brain capillary endothelial cell receptor, transferrin, transferrin receptor (e.g, soluble transferrin receptor), insulin, insulin-like growth factor 1 (IGF 1) receptor, insulin-like growth factor 2 (IGF 2) receptor, insulin receptor, blood coagulation factor X, α1-antitrypsin and HNF 1α. Suitable polypeptides that enhance serum half-life also include alpha-1 glycoprotein (orosomucoid; AAG), alpha-1 antichymotrypsin (ACT), alpha-1 microglobulin (protein HC; AIM), antithrombin III (AT III), apolipoprotein A-1 (Apo A-1), apolipoprotein B (Apo B), ceruloplasmin (Cp), complement component C3 (C3), complement component C4 (C4), C1 esterase inhibitor (C1 INH), C-reactive protein (CRP), ferritin (FER), hemopexin (HPX), lipoprotein(a) (Lp(a)), mannose-binding protein (MBP), myoglobin (Myo), prealbumin (transthyretin; PAL), retinol-binding protein (RBP), and rheumatoid factor (RF).

Suitable proteins from the extracellular matrix include, for example, collagens, laminins, integrins and fibronectin. Collagens are the major proteins of the extracellular matrix. About 15 types of collagen molecules are currently known, found in different parts of the body, e.g, type I collagen (accounting for 90% of body collagen) found in bone, skin, tendon, ligaments, cornea, internal organs or type II collagen found in cartilage, vertebral disc, notochord, and vitreous humor of the eye.

Suitable proteins from the blood include, for example, plasma proteins (e.g, fibrin, α-2 macroglobulin, serum albumin, fibrinogen (e.g, fibrinogen A, fibrinogen B), serum amyloid protein A, haptoglobin, profilin, ubiquitin, uteroglobulin and β-2-microglobulin), enzymes and enzyme inhibitors (e.g, plasminogen, lysozyme, cystatin C, alpha-1-antitrypsin and pancreatic trypsin inhibitor), proteins of the immune system, such as immunoglobulin proteins (e.g, IgA, IgD, IgE, IgG, IgM, immunoglobulin light chains (kappa/lambda)), transport proteins (e.g, retinol binding protein, α-1 microglobulin), defensins (e.g, beta-defensin 1, neutrophil defensin 1, neutrophil defensin 2 and neutrophil defensin 3) and the like.

Suitable proteins found at the blood brain barrier or in neural tissue include, for example, melanocortin receptor, myelin, ascorbate transporter and the like.

Suitable polypeptides that enhance serum half-life in vivo also include proteins localized to the kidney (e.g. polycystin, type IV collagen, organic anion transporter KI, Heymann's antigen), proteins localized to the liver (e.g, alcohol dehydrogenase, G250), proteins localized to the lung (e.g, secretory component, which binds IgA), proteins localized to the heart (e.g, HSP 27, which is associated with dilated cardiomyopathy), proteins localized to the skin (e.g, keratin), bone specific proteins such as morphogenic proteins (BMPs), which are a subset of the transforming growth factor β superfamily of proteins that demonstrate osteogenic activity (e.g, BMP-2, BMP-4, BMP-5, BMP-6, BMP-7, BMP-8), tumor specific proteins (e.g, trophoblast antigen, herceptin receptor, oestrogen receptor, cathepsins (e.g, cathepsin B, which can be found in liver and spleen)).

Suitable disease-specific proteins include, for example, antigens expressed only on activated T-cells, including LAG-3 (lymphocyte activation gene), osteoprotegerin ligand (OPGL; see Nature 402, 304-309 (1999)), OX40 (a member of the TNF receptor family, expressed on activated T cells and specifically up-regulated in human T cell leukemia virus type-I (HTLV-I)-producing cells; see Immunol. 165 (1):263-70 (2000)). Suitable disease-specific proteins also include, for example, metalloproteases (associated with arthritis/cancers) including CG6512 Drosophila, human paraplegin, human FtsH, human AFG3L2, murine ftsH; and angiogenic growth factors, including acidic fibroblast growth factor (FGF-1), basic fibroblast growth factor (FGF-2), vascular endothelial growth factor/vascular permeability factor (VEGF/VPF), transforming growth factor-α (TGF α), tumor necrosis factor-alpha (TNF-α), angiogenin, interleukin-3 (IL-3), interleukin-8 (IL-8), platelet-derived endothelial growth factor (PD-ECGF), placental growth factor (PlGF), midkine platelet-derived growth factor-BB (PDGF), and fractalkine.

Suitable polypeptides that enhance serum half-life in vivo also include stress proteins such as heat shock proteins (HSPs). HSPs are normally found intracellularly. When they are found extracellularly, it is an indicator that a cell has died and spilled out its contents. This unprogrammed cell death (necrosis) occurs when as a result of trauma, disease or injury, extracellular HSPs trigger a response from the immune system. Binding to extracellular HSP can result in localizing the compositions of the invention to a disease site.

Suitable proteins involved in Fc transport include, for example, Brambell receptor (also known as FcRB). This Fc receptor has two functions, both of which are potentially useful for delivery. The functions are (1) transport of IgG from mother to child across the placenta (2) protection of IgG from degradation thereby prolonging its serum half-life. It is thought that the receptor recycles IgG from endosomes. (See, Holliger et al, Nat Biotechnol 15(7):632-6 (1997).)

dAbs that Bind Serum Albumin

The invention in one embodiment provides a ligand, polypeptide or antagonist (e.g., dual specific ligand comprising an anti-TNFR1 dAb (a first dAb)) that binds to TNFR1 and a second dAb that binds serum albumin (SA), the second dAb binding SA with a KD as determined by surface plasmon resonance of about 1 nM to about 1, about 2, about 3, about 4, about 5, about 10, about 20, about 30, about 40, about 50, about 60, about 70, about 100, about 200, about 300, about 400 or about 500 µM (i.e., $\times 10^{-9}$ to $5 \times 10^{-4}$M), or about 100 nM to about 10 µM, or about 1 to about 5 µM or about 3 to about 70 nM or about 10 nM to about 1, about 2, about 3, about 4 or about 5 µM. For example about 30 to about 70 nM as determined by surface plasmon resonance. In one embodiment, the first dAb (or a dAb monomer) binds SA (e.g., HSA) with a KD as determined by surface plasmon resonance of approximately about 1, about 50, about 70, about 100, about 150, about 200, about 300 nM or about 1, about 2 or about 3 µM. In one embodiment, for a dual specific ligand comprising a first anti-SA dAb and a second dAb to TNFR1, the affinity (e.g., KD and/or $K_{off}$ as measured by surface plasmon resonance, e.g., using BiaCore) of the second dAb for its target is from about 1 to about 100000 times (e.g., about 100 to about 100000, or about 1000 to about 100000, or about 10000 to about 100000 times) the affinity of the first dAb for SA. In one embodiment, the serum albumin is human serum albumin (HSA). For example, the first dAb binds SA with an affinity of approximately about 10 µM, while the second dAb binds its target with an affinity of about 100 pM. In one embodiment, the serum albumin is human serum albumin (HSA). In one embodiment, the first dAb binds SA (e.g., HSA) with a KD of approximately about 50, for example about 70, about 100, about 150 or about 200 nM. Details of dual specific ligands are found in WO03002609, WO04003019, WO2008096158 and WO04058821.

The ligands of the invention can in one embodiment comprise a dAb that binds serum albumin (SA) with a KD as determined by surface plasmon resonance of about 1 nM to about 1, about 2, about 3, about 4, about 5, about 10, about 20, about 30, about 40, about 50, about 60, about 70, about 100, about 200, about 300, about 400 or about 500 µM (i.e., × about $10^{-9}$ to about $5 \times 10^{-4}$ M), or about 100 nM to about 10 µM, or about 1 to about 5 µM or about 3 to about 70 nM or about 10 nM to about 1, about 2, about 3, about 4 or about 5 µM. For example about 30 to about 70 nM as determined by surface plasmon resonance. In one embodiment, the first dAb (or a dAb monomer) binds SA (e.g., HSA) with a KD as determined by surface plasmon resonance of approximately about 1, about 50, about 70, about 100, about 150, about 200, about 300 nM or about 1, about 2 or about 3 µM. In one embodiment, the first and second dAbs are linked by a linker, for example a linker of from 1 to 4 amino acids or from 1 to 3 amino acids, or greater than 3 amino acids or greater than 4, 5, 6, 7, 8, 9, 10, 15 or 20 amino acids. In one embodiment, a longer linker (greater than 3 amino acids) is used to enhance potency (KD of one or both dAbs in the antagonist).

In particular embodiments of the ligands and antagonists, the dAb binds human serum albumin and competes for binding to albumin with a dAb selected from the group consisting of DOM7h-11, DOM7h-11-3, DOM7h-11-12, DOM7h-11-15, DOM7h-14, DOM7h-14-10, DOM7h-14-18 and DOM7m-16.

In particular embodiments of the ligands and antagonists, the dAb binds human serum albumin and competes for binding to albumin with a dAb selected from the group consisting of MSA-16, MSA-26 (See WO04003019 for disclosure of these sequences, which sequences and their nucleic acid counterpart are incorporated herein by reference and form part of the disclosure of the present text), DOM7m-16 (SEQ ID NO: 473), DOM7m-12 (SEQ ID NO: 474), DOM7m-26 (SEQ ID NO: 475), DOM7r-1 (SEQ ID NO: 476), DOM7r-3 (SEQ ID NO: 477), DOM7r-4 (SEQ ID NO: 478), DOM7r-5 (SEQ ID NO: 479), DOM7r-7 (SEQ ID NO: 480), DOM7r-8 (SEQ ID NO: 481), DOM7h-2 (SEQ ID NO: 482), DOM7h-3 (SEQ ID NO: 483), DOM7h-4 (SEQ ID NO: 484), DOM7h-6 (SEQ ID NO: 485), DOM7h-1 (SEQ ID NO: 486), DOM7h-7 (SEQ ID NO: 487), DOM7h-22 (SEQ ID NO: 489), DOM7h-23 (SEQ ID NO: 490), DOM7h-24 (SEQ ID NO: 491), DOM7h-25 (SEQ ID NO: 492), DOM7h-26 (SEQ ID NO: 493), DOM7h-21 (SEQ ID NO: 494), DOM7h-27 (SEQ ID NO: 495), DOM7h-8 (SEQ ID NO: 496), DOM7r-13 (SEQ ID NO: 497), DOM7r-14 (SEQ ID NO: 498), DOM7r-15 (SEQ ID NO: 499), DOM7r-16 (SEQ ID NO: 500), DOM7r-17 (SEQ ID NO: 501), DOM7r-18 (SEQ ID NO: 502), DOM7r-19 (SEQ ID NO: 503), DOM7r-20 (SEQ ID NO: 504), DOM7r-21 (SEQ ID NO: 505), DOM7r-22 (SEQ ID NO: 506), DOM7r-23 (SEQ ID NO: 507), DOM7r-24 (SEQ ID NO: 508), DOM7r-25 (SEQ ID NO: 509), DOM7r-26 (SEQ ID NO: 510), DOM7r-27 (SEQ ID NO: 511), DOM7r-28 (SEQ ID NO: 512), DOM7r-29 (SEQ ID NO: 513), DOM7r-30 (SEQ ID NO: 514), DOM7r-31 (SEQ ID NO: 515), DOM7r-32 (SEQ ID NO: 516), DOM7r-33 (SEQ ID NO: 517) (See WO2007080392 for disclosure of these sequences, which sequences and their nucleic acid counterpart are incorporated herein by reference and form part of the disclosure of the present text; the SEQ ID No's in this paragraph are those that appear in WO2007080392), dAb8 (dAb10), dAb 10, dAb36, dAb7r20 (DOM7r20), dAb7r21 (DOM7r21), dAb7r22 (DOM7r22), dAb7r23 (DOM7r23), dAb7r24 (DOM7r24), dAb7r25 (DOM7r25), dAb7r26 (DOM7r26), dAb7r27 (DOM7r27), dAb7r28 (DOM7r28), dAb7r29 (DOM7r29), dAb7r29 (DOM7r29), dAb7r31 (DOM7r31), dAb7r32 (DOM7r32), dAb7r33 (DOM7r33), dAb7r33 (DOM7r33), dAb7h22 (DOM7h22), dAb7h23 (DOM7h23), dAb7h24 (DOM7h24), dAb7h25 (DOM7h25), dAb7h26 (DOM7h26), dAb7h27 (DOM7h27), dAb7h30 (DOM7h30), dAb7h31 (DOM7h31), dAb2 (dAbs 4, 7, 41), dAb4, dAb7, dAb11, dAb12 (dAb7 m12), dAb13 (dAb 15), dAb15, dAb16 (dAb21, dAb7m16), dAb17, dAb18, dAb19, dAb21, dAb22, dAb23, dAb24, dAb25 (dAb26, dAb7m26), dAb27, dAb30 (dAb35), dAb31, dAb33, dAb34, dAb35, dAb38 (dAb54), dAb41, dAb46 (dAbs 47, 52 and 56), dAb47, dAb52, dAb53, dAb54, dAb55, dAb56, dAb7m12, dAb7m16, dAb7m26, dAb7r1 (DOM7r1), dAb7r3 (DOM7r3), dAb7r4 (DOM7r4), dAb7r5 (DOM7r5), dAb7r7 (DOM7r7), dAb7r8 (DOM7r8), dAb7r13 (DOM7r13), dAb7r14 (DOM7r14), dAb7r15 (DOM7r15), dAb7r16 (DOM7r16), dAb7r17 (DOM7r17), dAb7r18 (DOM7r18), dAb7r19 (DOM7r19), dAb7h1 (DOM7h1), dAb7h2 (DOM7h2), dAb7h6 (DOM7h6), dAb7h7 (DOM7h7), dAb7h8 (DOM7h8), dAb7h9 (DOM7h9), dAb7h10 (DOM7h10), dAb7h11 (DOM7h11), dAb7h12 (DOM7h12), dAb7h13 (DOM7h13), dAb7h14 (DOM7h14), dAb7p1 (DOM7p1), and dAb7p2 (DOM7p2) (see WO2008096158 for disclosure of these sequences, which sequences and their nucleic acid counterpart are incorporated herein by reference and form part of the disclosure of the present text). Alternative names are shown in brackets after the dAb, e.g, dAb8 has an alternative name which is dAb10 i.e. dAb8 (dAb10).

In certain embodiments, the dAb binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with the amino acid sequence of a dAb selected from the group consisting of DOM7h-11, DOM7h-11-3, DOM7h-11-12, DOM7h-11-15, DOM7h-14, DOM7h-14-10, DOM7h-14-18 and DOM7m-16.

In certain embodiments, the dAb binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with the amino acid sequence of a dAb selected from the group consisting of

MSA-16, MSA-26,

DOM7m-16 (SEQ ID NO: 473), DOM7m-12 (SEQ ID NO: 474), DOM7m-26 (SEQ ID NO: 475), DOM7r-1 (SEQ ID NO: 476), DOM7r-3 (SEQ ID NO: 477), DOM7r-4 (SEQ ID NO: 478), DOM7r-5 (SEQ ID NO: 479), DOM7r-7 (SEQ ID NO: 480), DOM7r-8 (SEQ ID NO: 481), DOM7h-2 (SEQ

ID NO: 482), DOM7h-3 (SEQ ID NO: 483), DOM7h-4 (SEQ ID NO: 484), DOM7h-6 (SEQ ID NO: 485), DOM7h-1 (SEQ ID NO: 486), DOM7h-7 (SEQ ID NO: 487), DOM7h-22 (SEQ ID NO: 489), DOM7h-23 (SEQ ID NO: 490), DOM7h-24 (SEQ ID NO: 491), DOM7h-25 (SEQ ID NO: 492), DOM7h-26 (SEQ ID NO: 493), DOM7h-21 (SEQ ID NO: 494), DOM7h-27 (SEQ ID NO: 495), DOM7h-8 (SEQ ID NO: 496), DOM7r-13 (SEQ ID NO: 497), DOM7r-14 (SEQ ID NO: 498), DOM7r-15 (SEQ ID NO: 499), DOM7r-16 (SEQ ID NO: 500), DOM7r-17 (SEQ ID NO: 501), DOM7r-18 (SEQ ID NO: 502), DOM7r-19 (SEQ ID NO: 503), DOM7r-20 (SEQ ID NO: 504), DOM7r-21 (SEQ ID NO: 505), DOM7r-22 (SEQ ID NO: 506), DOM7r-23 (SEQ ID NO: 507), DOM7r-24 (SEQ ID NO: 508), DOM7r-25 (SEQ ID NO: 509), DOM7r-26 (SEQ ID NO: 510), DOM7r-27 (SEQ ID NO: 511), DOM7r-28 (SEQ ID NO: 512), DOM7r-29 (SEQ ID NO: 513), DOM7r-30 (SEQ ID NO: 514), DOM7r-31 (SEQ ID NO: 515), DOM7r-32 (SEQ ID NO: 516), DOM7r-33 (SEQ ID NO: 517) (the SEQ ID No's in this paragraph are those that appear in WO2007080392), dAb8, dAb 10, dAb36, dAb7r20, dAb7r21, dAb7r22, dAb7r23, dAb7r24, dAb7r25, dAb7r26, dAb7r27, dAb7r28, dAb7r29, dAb7r30, dAb7r31, dAb7r32, dAb7r33, dAb7h21, dAb7h22, dAb7h23, dAb7h24, Ab7h25, Ab7h26, dAb7h27, dAb7h30, dAb7h31, dAb2, dAb4, dAb7, dAb11, dAb12, dAb13, dAb15, dAb16, dAb17, dAb18, dAb19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, dAb7m12, dAb7m16, dAb7m26, dAb7r1, dAb7r3, dAb7r4, dAb7r5, dAb7r7, dAb7r8, dAb7r13, dAb7r14, dAb7r15, dAb7r16, dAb7r17, dAb7r18, dAb7r19, dAb7h1, dAb7h2, dAb7h6, dAb7h7, dAb7h8, dAb7h9, dAb7h10, dAb7h11, dAb7h12, dAb7h13, dAb7h14, dAb7p1, and dAb7p2.

For example, the dAb that binds human serum albumin can comprise an amino acid sequence that has at least about 90%, or at least about 95%, or at least about 96%, or at least about 97%, or at least about 98%, or at least about 99% amino acid sequence identity with DOM7h-11-3 or DOM7h-14-10.

For example, the dAb that binds human serum albumin can comprise an amino acid sequence that has at least about 90%, or at least about 95%, or at least about 96%, or at least about 97%, or at least about 98%, or at least about 99% amino acid sequence identity with DOM7h-2 (SEQ ID NO:482), DOM7h-3 (SEQ ID NO:483), DOM7h-4 (SEQ ID NO:484), DOM7h-6 (SEQ ID NO:485), DOM7h-1 (SEQ ID NO:486), DOM7h-7 (SEQ ID NO:487), DOM7h-8 (SEQ ID NO:496), DOM7r-13 (SEQ ID NO:497), DOM7r-14 (SEQ ID NO:498), DOM7h-22 (SEQ ID NO:489), DOM7h-23 (SEQ ID NO:490), DOM7h-24 (SEQ ID NO:491), DOM7h-25 (SEQ ID NO:492), DOM7h-26 (SEQ ID NO:493), DOM7h-21 (SEQ ID NO:494) or DOM7h-27 (SEQ ID NO:495) (the SEQ ID No's in this paragraph are those that appear in WO2007080392), or dAb8, dAb 10, dAb36, dAb7h21, dAb7h22, dAb7h23, Ab7h24, Ab7h25, Ab7h26, dAb7h27, dAb7h30, dAb7h31, dAb2, dAb4, dAb7, dAb11, dAb12, dAb13, dAb15, dAb16, dAb17, dAb18, dAb19, dAb21, dAb22, dAb23, dAb24, dAb25, dAb26, dAb27, dAb30, dAb31, dAb33, dAb34, dAb35, dAb38, dAb41, dAb46, dAb47, dAb52, dAb53, dAb54, dAb55, dAb56, dAb7h1, dAb7h2, dAb7h6, dAb7h7, dAb7h8, dAb7h9, dAb7h10, dAb7h11, dAb7h12, dAb7h13 or dAb7h14.

In certain embodiments, the dAb binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with the amino acid sequence of a dAb selected from the group consisting of DOM7h-2 (SEQ ID NO:482), DOM7h-6 (SEQ ID NO:485), DOM7h-1 (SEQ ID NO:486), DOM7h-7 (SEQ ID NO:487), DOM7h-8 (SEQ ID NO:496), DOM7h-22 (SEQ ID NO:489), DOM7h-23 (SEQ ID NO:490), DOM7h-24 (SEQ ID NO:491), DOM7h-25 (SEQ ID NO:492), DOM7h-26 (SEQ ID NO:493), DOM7h-21 (SEQ ID NO:494), DOM7h-27 (SEQ ID NO:495) (the SEQ ID No's in this paragraph are those that appear in WO2007080392), dAb7h21, dAb7h22, dAb7h23, Ab7h24, Ab7h25, Ab7h26, dAb7h27, dAb7h30, dAb7h31, dAb2, dAb4, dAb7, dAb38, dAb41, dAb7h1, dAb7h2, dAb7h6, dAb7h7, dAb7h8, dAb7h9, dAb7h10, dAb7h11, dAb7h12, dAb7h13 and dAb7h14.

In more particular embodiments, the dAb is a $V_K$ dAb that binds human serum albumin and has an amino acid sequence selected from the group consisting of DOM7h-2 (SEQ ID NO:482), DOM7h-6 (SEQ ID NO:485), DOM7h-1 (SEQ ID NO:486), DOM7h-7 (SEQ ID NO:487), DOM7h-8 (SEQ ID NO:496) (the SEQ ID No's in this paragraph are those that appear in WO2007080392), dAb2, dAb4, dAb7, dAb38, dAb41, dAb54, dAb7h1, dAb7h2, dAb7h6, dAb7h7, dAb7h8, dAb7h9, dAb7h10, dAb7h11, dAb7h12, dAb7h13 and dAb7h14.

In more particular embodiments, the dAb is a $V_H$ dAb that binds human serum albumin and has an amino acid sequence selected from dAb7h30 and dAb7h31.

In more particular embodiments, the dAb is dAb7h11 or dAb7h14. In an example, the dAb is DOM7h-11-3. In another example, the dAb is DOM7h-14-10.

In other embodiments, the dAb, ligand or antagonist binds human serum albumin and comprises one, two or three of the CDRs of any of the foregoing amino acid sequences, eg one, two or three of the CDRs of DOM7h-11-3, DOM7h-14-10, dAb7h11 or dAb7h14.

Suitable Camelid $V_{HH}$ that bind serum albumin include those disclosed in WO 2004/041862 (Ablynx N.V.) and in WO2007080392 (which $V_{HH}$ sequences and their nucleic acid counterpart are incorporated herein by reference and form part of the disclosure of the present text), such as Sequence A (SEQ ID NO:518), Sequence B (SEQ ID NO:519), Sequence C (SEQ ID NO:520), Sequence D (SEQ ID NO:521), Sequence E (SEQ ID NO:522), Sequence F (SEQ ID NO:523), Sequence G (SEQ ID NO:524), Sequence H (SEQ ID NO:525), Sequence I (SEQ ID NO:526), Sequence J (SEQ ID NO:527), Sequence K (SEQ ID NO:528), Sequence L (SEQ ID NO:529), Sequence M (SEQ ID NO:530), Sequence N (SEQ ID NO:531), Sequence 0 (SEQ ID NO:532), Sequence P (SEQ ID NO:533), Sequence Q (SEQ ID NO:534), these sequence numbers corresponding to those cited in WO2007080392 or WO 2004/041862 (Ablynx N.V.). In certain embodiments, the Camelid $V_{HH}$ binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with ALB1 disclosed in WO2007080392 or any one of SEQ ID NOS:518-534, these sequence numbers corresponding to those cited in WO2007080392 or WO 2004/041862.

In some embodiments, the ligand or antagonist comprises an anti-serum albumin dAb that competes with any anti-serum albumin dAb disclosed herein for binding to serum albumin (e.g, human serum albumin).

In an alternative embodiment, the antagonist or ligand comprises a binding moiety specific for SA (e.g., human SA), wherein the moiety comprises non-immunoglobulin sequences as described in WO2008096158, the disclosure of these binding moieties, their methods of production and selection (e.g., from diverse libraries) and their sequences are incorporated herein by reference as part of the disclosure of the present text)

Conjugation to a Half-Life Extending Moiety (e.g., Albumin)

In one embodiment, a (one or more) half-life extending moiety (e.g., albumin, transferrin and fragments and analogues thereof) is conjugated or associated with the TNFR1-binding polypeptide, dAb or antagonist of the invention. Examples of suitable albumin, albumin fragments or albumin variants for use in a TNFR1-binding format are described in WO 2005077042, which disclosure is incorporated herein by reference and forms part of the disclosure of the present text. In particular, the following albumin, albumin fragments or albumin variants can be used in the present invention:

SEQ ID NO:1 (as disclosed in WO 2005077042, this sequence being explicitly incorporated into the present disclosure by reference);

Albumin fragment or variant comprising or consisting of amino acids 1-387 of SEQ ID NO:1 in WO 2005077042;

Albumin, or fragment or variant thereof, comprising an amino acid sequence selected from the group consisting of: (a) amino acids 54 to 61 of SEQ ID NO:1 in WO 2005077042; (b) amino acids 76 to 89 of SEQ ID NO:1 in WO 2005077042; (c) amino acids 92 to 100 of SEQ ID NO:1 in WO 2005077042; (d) amino acids 170 to 176 of SEQ ID NO:1 in WO 2005077042; (e) amino acids 247 to 252 of SEQ ID NO:1 in WO 2005077042; (f) amino acids 266 to 277 of SEQ ID NO:1 in WO 2005077042; (g) amino acids 280 to 288 of SEQ ID NO:1 in WO 2005077042; (h) amino acids 362 to 368 of SEQ ID NO:1 in WO 2005077042; (i) amino acids 439 to 447 of SEQ ID NO:1 in WO 2005077042 (j) amino acids 462 to 475 of SEQ ID NO:1 in WO 2005077042; (k) amino acids 478 to 486 of SEQ ID NO:1 in WO 2005077042; and (l) amino acids 560 to 566 of SEQ ID NO:1 in WO 2005077042.

Further examples of suitable albumin, fragments and analogs for use in a TNFR1-binding format are described in WO 03076567, which disclosure is incorporated herein by reference and which forms part of the disclosure of the present text. In particular, the following albumin, fragments or variants can be used in the present invention:

Human serum albumin as described in WO 03076567, e.g., in FIG. 3 (this sequence information being explicitly incorporated into the present disclosure by reference);

Human serum albumin (HA) consisting of a single non-glycosylated polypeptide chain of 585 amino acids with a formula molecular weight of 66,500 (See, Meloun, et al., *FEBS Letters* 58:136 (1975); Behrens, et al., *Fed. Proc.* 34:591 (1975); Lawn, et al., *Nucleic Acids Research* 9:6102-6114 (1981); Minghetti, et al., *J. Biol. Chem.* 261:6747 (1986));

A polymorphic variant or analog or fragment of albumin as described in Weitkamp, et al., *Ann. Hum. Genet.* 37:219 (1973);

An albumin fragment or variant as described in EP 322094, e.g., HA(1-373, HA(1-388), HA(1-389), HA(1-369), and HA(1-419) and fragments between 1-369 and 1-419;

An albumin fragment or variant as described in EP 399666, e.g., HA(1-177) and HA(1-200) and fragments between HA(1-X), where X is any number from 178 to 199.

Where a (one or more) half-life extending moiety (e.g., albumin, transferrin and fragments and analogues thereof) is used to format the TNFR1-binding polypeptides, dAbs and antagonists of the invention, it can be conjugated using any suitable method, such as, by direct fusion to the TNFR1-binding moiety (e.g., anti-TNFR1 dAb), for example by using a single nucleotide construct that encodes a fusion protein, wherein the fusion protein is encoded as a single polypeptide chain with the half-life extending moiety located N- or C-terminally to the TNFR1 binding moiety. Alternatively, conjugation can be achieved by using a peptide linker between moieties, e.g., a peptide linker as described in WO 03076567 or WO 2004003019 (these linker disclosures being incorporated by reference in the present disclosure to provide examples for use in the present invention). Typically, a polypeptide that enhances serum half-life in vivo is a polypeptide which occurs naturally in vivo and which resists degradation or removal by endogenous mechanisms which remove unwanted material from the organism (e.g, human). For example, a polypeptide that enhances serum half-life in vivo can be selected from proteins from the extracellular matrix, proteins found in blood, proteins found at the blood brain barrier or in neural tissue, proteins localized to the kidney, liver, lung, heart, skin or bone, stress proteins, disease-specific proteins, or proteins involved in Fc transport.

In embodiments of the invention described throughout this disclosure, instead of the use of an anti-TNFR1 single variable domain ("dAb") in an antagonist or ligand of the invention, it is contemplated that the skilled addressee can use a polypeptide or domain that comprises one or more or all 3 of the CDRs of a dAb of the invention that binds TNFR1 (e.g, CDRs grafted onto a suitable protein scaffold or skeleton, eg an affibody, an SpA scaffold, an LDL receptor class A domain or an EGF domain) The disclosure as a whole is to be construed accordingly to provide disclosure of antagonists using such domains in place of a dAb. In this respect, see WO2008096158 for details of how to produce diverse libraries of based on protein scaffolds and selection and characterization of domains from such libraries, the disclosure of which is incorporated by reference).

In one embodiment, therefore, an antagonist of the invention comprises an immunoglobulin single variable domain or domain antibody (dAb) that has binding specificity for TNFR1 or the complementarity determining regions of such a dAb in a suitable format. The antagonist can be a polypeptide that consists of such a dAb, or consists essentially of such a dAb. The antagonist can be a polypeptide that comprises a dAb (or the CDRs of a dAb) in a suitable format, such as an antibody format (e.g, IgG-like format, scFv, Fab, Fab', F(ab')$_2$), or a dual specific ligand that comprises a dAb that binds TNFR1 and a second dAb that binds another target protein, antigen or epitope (e.g, serum albumin).

Polypeptides, dAbs and antagonists according to the invention can be formatted as a variety of suitable antibody formats that are known in the art, such as, IgG-like formats, chimeric antibodies, humanized antibodies, human antibodies, single chain antibodies, bispecific antibodies, antibody heavy chains, antibody light chains, homodimers and heterodimers of antibody heavy chains and/or light chains, antigen-binding fragments of any of the foregoing (e.g, a Fv fragment (e.g, single chain Fv (scFv), a disulfide bonded Fv), a Fab fragment, a Fab' fragment, a F(ab')$_2$ fragment), a single variable domain (e.g, $V_H$, $V_L$), a dAb, and modified versions of any of the foregoing (e.g, modified by the covalent attachment of polyalkylene glycol (e.g, polyethylene glycol, polypropylene glycol, polybutylene glycol) or other suitable polymer).

In some embodiments, the invention provides a ligand (e.g., an anti-TNFR1 antagonist) that is an IgG-like format. Such formats have the conventional four chain structure of an IgG molecule (2 heavy chains and two light chains), in which one or more of the variable regions ($V_H$ and or $V_L$) have been replaced with a dAb of the invention. In one embodiment, each of the variable regions (2 $V_H$ regions and 2 $V_L$ regions) is replaced with a dAb or single variable domain, at least one of which is an anti-TNFR1 dAb according to the invention. The dAb(s) or single variable domain(s) that are included in an IgG-like format can have the same specificity or different specificities. In some embodiments, the IgG-like format is tetravalent and can have one (anti-TNFR1 only), two (e.g., anti-TNFR1 and anti-SA), three or four specificities. For example, the IgG-like format can be monospecific and comprises 4 dAbs that have the same specificity; bispecific and comprises 3 dAbs that have the same specificity and another dAb that has a different specificity; bispecific and comprise two dAbs that have the same specificity and two dAbs that have a common but different specificity; trispecific and comprises first and second dAbs that have the same specificity, a third dAb with a different specificity and a fourth dAb with a different specificity from the first, second and third dAbs; or tetraspecific and comprise four dAbs that each have a different specificity. Antigen-binding fragments of IgG-like formats (e.g, Fab, F(ab')$_2$, Fab', Fv, scF$_v$) can be prepared. In one embodiment, the IgG-like formats or antigen-binding fragments may be monovalent for TNFR1. If complement activation and/or antibody dependent cellular cytotoxicity (ADCC) function is desired, the ligand can be an IgG1-like format. If desired, the IgG-like format can comprise a mutated constant region (variant IgG heavy chain constant region) to minimize binding to Fc receptors and/or ability to fix complement. (see e.g., Winter et al, GB 2,209,757 B; Morrison et al., WO 89/07142; Morgan et al., WO 94/29351, Dec. 22, 1994).

The ligands of the invention (e.g., polypeptides, dAbs and antagonists) can be formatted as a fusion protein that contains a first immunoglobulin single variable domain that is fused directly to a second immunoglobulin single variable domain. If desired such a format can further comprise a half-life extending moiety. For example, the ligand can comprise a first immunoglobulin single variable domain that is fused directly to a second immunoglobulin single variable domain that is fused directly to an immunoglobulin single variable domain that binds serum albumin.

Generally the orientation of the polypeptide domains that have a binding site with binding specificity for a target, and whether the ligand comprises a linker, is a matter of design choice. However, some orientations, with or without linkers, may provide better binding characteristics than other orientations. All orientations (e.g, dAb1-linker-dAb2; dAb2-linker-dAb1) are encompassed by the invention are ligands that contain an orientation that provides desired binding characteristics can be easily identified by screening.

Polypeptides and dAbs according to the invention, including dAb monomers, dimers and trimers, can be linked to an antibody Fc region, comprising one or both of $C_H2$ and $C_H3$ domains, and optionally a hinge region. For example, vectors encoding ligands linked as a single nucleotide sequence to an Fc region may be used to prepare such polypeptides.

The invention moreover provides dimers, trimers and polymers of the aforementioned dAb monomers.

EXAMPLES

The biophysical properties of antibody fragments play a key role in determining if an antibody fragment is developable as a therapeutic or not. One of these biophysical properties is the stability of the antibody fragment to precipitation when stored. Accelerated stability testing is a technique used to evaluate stability more rapidly by incubating the protein at elevated temperatures for prolonged periods of time and then determining the level of precipitation. Therefore, we characterised seven anti-TNFR1 dAbs for their accelerated stability. Due to the very different properties (especially different Tm) of the individual dAbs to be studied, the accelerated stability studies of these dAbs were all carried out at 40° C.

The protocol used to test for accelerated stability is the following: all proteins were buffer exchanged into PBS and adjusted to a concentration of 1 mg/ml. Four aliquots (corresponding to 4 time points; 0 h, 2 h, 23 h and 47 h) of 250 µl were prepared in 0.5 ml eppendorfs. The first samples (47 h time point) were placed into an oven set at 40° C.; 24 hours later the second 250 µl aliquots (23 h time point) were placed in the oven; a further 20 hours later the third 250 µl aliquots (2 h time point) were placed in the oven; the 0 h aliquots were kept at 4° C. during this study. All aliquots were kept at 4° C. until they were placed in the 40° C. oven. After a total of 47 h all aliquots were removed from the oven and centrifuged at 16,100×g for 10 mins. The A280 of each sample was measured, using a 96-well UV plate reader, to monitor the amount of protein which was still in solution. This data was used to calculate the protein concentration for each protein at each time point and this was in turn plotted against time to monitor the loss of protein over time.

Example 1

Testing Anti-TNFR1 dAbs for Accelerated Stability

For the anti-TNFR1 dAbs, six related anti-TNFR1 dAbs were evaluated, i.e. DOM1h-574-72, DOM1h-574-109, DOM1h-574-133, DOM1h-574-138, DOM1h-574-156 and DOM1h-574-180, as well as the unrelated anti-TNFR1 dAb DOM1h-131-206. Genetic constructs of all these dAbs cloned SalI/NotI in pDOM13 (a pBR322-derived expression vector) were transformed to *E. coli* HB2151 followed by protein expression in the supernatant. The dAbs were purified from the supernatant in a single-step purification on Protein-A Streamline (GE Healthcare cat no. 17-1281-03), followed by elution with 100 mM Glycine pH2.0 and neutralisation with 200 mM Tris pH8. After concentration, the dAbs were buffer exchanged to PBS by dialysis and tested for accelerated stability at 1 mg/ml. The results of the accelerated stability are shown in Table 1, which quotes the amount dAb in solution at each time point as a percentage of the amount of dAb present at t=0 h.

TABLE 1

Accelerated stability for anti-TNFR1 dAbs when incubated at 1 mg/ml in PBS at 40° C. Values represent the amount of dAb in solution at each time point as a percentage of the amount of dAb present at t = 0 h.

| Clone | % in Solution | | | |
|---|---|---|---|---|
| | 0.0 h | 2.3 h | 23.0 h | 47.0 h |
| DOM1h-574-72 | 100% | 91% | 18% | 9% |
| DOM1h-574-109 | 100% | 86% | 18% | 8% |
| DOM1h-574-133 | 100% | 101% | 91% | 80% |
| DOM1h-574-138 | 100% | 100% | 39% | 18% |
| DOM1h-574-156 | 100% | 84% | 17% | 9% |
| DOM1h-574-180 | 100% | 73% | 12% | 8% |
| DOM1h-131-206 | 100% | 102% | 101% | 100% |

The anti-TNFR1 dAbs of the DOM1h-574 lineage, with the exception of DOM1h-574-133, tend to precipitate within the first 47 h, resulting in a substantially reduced amount of protein in solution at this time point. In contrast, the anti-TNFR1 dAb DOM1h-131-206 does stay in solution for this period of time. Therefore, stabilisation of the dAb to make it more resistant to precipitation in the accelerated stability study is beneficial.

Example 2

Selections and Screening of Anti-TNFR1 dAb Lineage DOM1H-574 for Improved Biophysical Properties To identify new dAbs with improved resistance to precipitation after incubation at elevated temperatures, error-prone PCR libraries were constructed based on five anti-TNFR1 dAbs: DOM1h-574-156, DOM1h-574-109, DOM1h-574-138, DOM1h-574-162 and DOM1h-574-180. The error-prone libraries were made using these clones in the pDOM13 vector as template and then subjected to two rounds of error-prone PCR using GeneMorph II (Stratagene, cat no. 200550). In the first round 50 ng of vector was amplified for 30 cycles in 50 μl volume using the oligonucleotides AS9 and AS339 and the following amplification profile: 2 min 95° C. and then 30 cycles of: 15 sec 95° C., 30 sec 50° C., 1 min 72° C.; and at the end 10 min 72° C.

In the second round, 0.4 μl of the first error-prone PCR reaction product was used as template in the second round of mutagenesis with GeneMorph II (Strategene) 200 μl volume using nested primers AS639 and AS65 and amplification profile: 2 min 95° C. and then 35 cycles of: 15 sec 95° C., 30 sec 50° C., 1 min 72° C.; and at the end 10 min 72° C.

PCR products were purified on 2% E-Gels using Qiagen Gel Extraction kit and cut with Sal I and Not I restriction endonucleases (NEB). The digestion reaction products were run on 2% E-Gels and the dAb-encoding DNA inserts were purified from the E-gels using Qiagen Gel Extraction kit. Purified inserts were ligated into pDOM33 phage display vector using T4 DNA ligase kit (NEB):

40 μl of 30 nM 0.7 μg/μl Sal I/Not I-cut pDOM33 vector
30 μl of 300 nM insert
400 μl of H$_2$O
50 μl of 10× Buffer
15 μl of 400 U/μl T4 DNA ligase The reactions were incubated at 16° C. for 18 hours. The reaction products were phenol-chloroform extracted, ethanol precipitated and dissolved in 50 μl of H$_2$O, added to 400 μl of electrocompetent TB1 *E. coli* cells and electroporated using Bio-Rad Gene Pulser II in 100 μl volume, before plating on tetracycline-2×TY agarose plates. On average, about 2.4×10$^8$ individual transformants were obtained for each of the five libraries. On average, there were about three amino acid mutations per gene.

Prior to starting selections for improved biophysical properties, the five, error-prone, phage libraries were pre-selected on soluble human TNFR1 (R&D Systems), which had been biotinylated using EZ-Link Sulfo-NHS-LC-Biotin (Pierce Protein Research Products, Rockford Ill., cat no. 21327), to enrich for functional phage with TNFR1 binding properties. The pre-selection was done using the following protocol:

1. Block 1 ml of M280 Streptavidin Dynabeads (Invitrogen) with 2% Marvel in PBS for 1 hour at room temperature.
2. Block about 10$^{11}$ transforming units (Tu) phage for each of the libraries in 0.5 ml PBS with 2% Marvel for one hour at room temperature.
3. Add 0.53 μl of 47 μM biotinylated human soluble TNFR1 to 0.5 ml of blocked phage. Incubate for 1 hour at room temperature.
4. Add 200 μl of blocked Dynabeads to phage solution. Incubate for 10 minutes at room temperature.
5. Wash five times with PBST (PBS with 0.1% Tween 20)
6. Elute bound phage with 500 μl of 0.1M Glycine pH=2.
7. Neutralized eluted phage with 100 μl of 1 M Tris pH8.

About 2% of input Tu phage was recovered at the end of the pre-selection round for each library. After pre-selection, the libraries for DOM1h-574-109, DOM1h-574-138, DOM1h-574-162 and DOM1h-574-180 lead clones were pooled, forming library A. Library B for DOM1h-574-156 was kept separately.

At this stage four phage-display selection strategies were adopted to enrich for DOM1h-574 variants with improved biophysical properties from these error-prone PCR libraries:
1) Kinetic stability at elevated temperatures (65 degrees centigrade)
2) Reversibility of thermal denaturation (80 degrees centigrade)
3) Resistance to protease digestion
4) Reversibility of low pH-induced denaturation.

Phage Display Library Selection Round 1.

In the first round of phage-display selection, Libraries A and B were diluted to 5×10$^{11}$ Tu/ml in PBS and 100 μl aliquots were then subjected to thermal, protease or low pH pre-treatment. For the thermal selections (samples 1 to 4, Table 2), temperatures of 50° C. to 80° C. were used and periods of incubation were either 2 h or 10 min, as indicated in Table 2 Trypsin (Promega, V511) selection (samples 5 to 7) were done at 10 to 100 μg/ml of trypsin for 2 h at 37° C. in PBS and control incubations were done at room temperature for 2 h in PBS (samples 8 and 9). Following incubation, 50 μl of 2× Complete protease inhibitors (Roche 04 693 116 001) was added to each of samples 5-9. For the acid selections, samples 10 to 13, phage were diluted 10-fold from the phage stock into 420 μl of HNC buffer (5 mM HEPES, 5 mM NaCl, 100 mM citrate, pH=3.2). At the end of the incubation (length of acid incubation for each sample is indicated in Table 2), the samples were neutralized with 80 μl of Tris buffer.

After incubation in these stress conditions, the phage libraries were selected for functionally active dAbs through incubation with biotinylated human soluble TNFR1, as described above in the pre-selection step. The only change to the protocol used was that ten washing steps were performed using a Kingfisher. For all selections with both Libraries A and B the number of phage recovered was determined and is shown in Table 2. Subsequently phage were amplified for a next round of selection.

TABLE 2

Round 1 selections for improved properties. Indicated are the selection conditions used and the Tu phage recovered from each of the two libraries after selection. Input for all selections was 5 × 10$^{10}$ Tu phage.

| | Selection conditions | Library A | Library B |
|---|---|---|---|
| 1 | Incubation at 50° C. for two hours | 4 × 10$^7$ | 1 × 10$^8$ |
| 2 | Incubation at 55° C. for two hours | 3 × 10$^7$ | 7 × 10$^7$ |
| 3 | Incubation at 60° C. for two hours | 1 × 10$^7$ | 2 × 10$^7$ |
| 4 | Incubation at 80° C. for ten minutes | 5 × 10$^6$ | 1 × 10$^7$ |
| 5 | Trypsin 10 μg/ml 37° C. for 2 hours in PBS | 1 × 10$^5$ | 1 × 10$^6$ |
| 6 | Trypsin 30 μg/ml 37° C. for 2 hours in PBS | 3 × 10$^5$ | 3 × 10$^8$ |

TABLE 2-continued

Round 1 selections for improved properties. Indicated are the selection conditions used and the Tu phage recovered from each of the two libraries after selection. Input for all selections was $5 \times 10^{10}$ Tu phage.

| | Selection conditions | Library A | Library B |
|---|---|---|---|
| 7 | Trypsin 100 μg/ml 37° C. for 2 hours in PBS | $1 \times 10^6$ | $1 \times 10^8$ |
| 8 | Room temperature for 2 hours in PBS | $1 \times 10^8$ | $1 \times 10^8$ |
| 9 | Room temperature for 2 hours in PBS | $1 \times 10^8$ | $1 \times 10^8$ |
| 10 | pH 3.2 at 37° C. for 30 minutes | $4 \times 10^7$ | $1 \times 10^7$ |
| 11 | pH 3.2 at 37° C. for 1 hour | $5 \times 10^7$ | $8 \times 10^6$ |
| 12 | pH 3.2 at 37° C. for 2 hours | $5 \times 10^6$ | $1 \times 10^6$ |
| 13 | pH 3.2 on ice for 1 min | $1 \times 10^8$ | $7 \times 10^7$ |

Based on recovery levels, the outputs from selections 3, 4, 5 and 12 for both libraries (and selection 6 from library A) were taken forward to a second round of selection. The phage outputs were amplified by a round of infection of *E. coli* and subsequently purified and concentrated to $2 \times 10^{14}$ Tu/ml.

Phage Display Library Selection Round 2.

Outputs from the first round of selections from libraries A and B were diluted to $5 \times 10^{11}$ Tu/ml in PBS and 100 μl aliquots of each were used for the second round of selection. Although the same protocol was used, the selection conditions were modified as summarised in Table 3

TABLE 3

Round 2 selection inputs, conditions and recovery. Input refers to selection condition reference used in round 1. For library A, the selection outputs for conditions 5 and 6 in round 1 were pooled and the pool used where indicated with a "*". Selection conditions included negative controls for background binding in the absence of ligand. Input for all selections was $5 \times 10^{10}$ Tu phage.

| | Input from Round 1 selection | Selection conditions | Recovered Tu from Library A | Recovered Tu from Library B |
|---|---|---|---|---|
| 1 | 3 | Incubation at 65° C. for two hours | $3 \times 10^8$ | $1 \times 10^8$ |
| 2 | 3 | Room temperature, Recovery with ligand | $1.5 \times 10^{10}$ | $3.5 \times 10^{10}$ |
| 3 | 3 | Room temperature, Recovery without ligand | 0 | 0 |
| 4 | 4 | Incubation at 80° C. for ten minutes | $1.5 \times 10^{10}$ | $3.5 \times 10^9$ |
| 5 | 4 | Room temperature, Recovery with ligand | $1.5 \times 10^{10}$ | $2.5 \times 10^{10}$ |
| 6 | 4 | Room temperature, Recovery without ligand | 0 | 0 |
| 7 | 5 | Trypsin 10 μg/ml 37° C. for 2 hours in PBS | * $3 \times 10^9$ | $3 \times 10^9$ |
| 8 | 5 | Trypsin 30 μg/ml 37° C. for 2 hours in PBS | * $1.5 \times 10^9$ | $2 \times 10^9$ |
| 9 | 5 | Trypsin 100 μg/ml 37° C., 2 hours in PBS | * $1.5 \times 10^9$ | $2 \times 10^9$ |
| 10 | 5 | Room temperature, Recovery with ligand | * $4 \times 10^{10}$ | $5 \times 10^{10}$ |
| 11 | 5 | Room temperature, Recovery without ligand | * 0 | 0 |
| 12 | 12 | pH 3.2 at 37° C. for 4 hours | $1.5 \times 10^9$ | $1 \times 10^9$ |
| 13 | 12 | pH 3.2 at 37° C. for overnight | $1 \times 10^7$ | $5 \times 10^6$ |
| 14 | 12 | Room temperature, Recovery with ligand | $5 \times 10^{10}$ | $2.5 \times 10^{10}$ |
| 15 | 12 | Room temperature, Recovery without ligand | $5 \times 10^4$ | 0 |

Phage outputs were purified and concentrated to $1 \times 10^{13}$ Tu/ml. Outputs from selections 1, 4, 9 and 12 for both libraries were taken forward to the next round of selection. The phage outputs were amplified by a round of infection of *E. coli* and subsequently purified and concentrated to $2 \times 10^{14}$ Tu/ml.

Phage Display Library Selection Round 3.

Outputs from the second round of selections from libraries A and B were diluted to $5 \times 10^{11}$ Tu/ml in PBS and 100 μl aliquots of each were used for the third round of selection. Although the same protocol was used, the selection conditions were modified as summarised in Table 4

TABLE 4

Round 3 selection inputs, conditions and recovery. Input refers to selection condition reference used in round 2. Selection conditions included negative controls for background binding in the absence of ligand. Input for all selections was $5 \times 10^{10}$ Tu phage, the recoveries were in a volume of 0.5 ml and results are expressed in Tu/ml.

| | Input from Round 2 selection | Selection conditions | Recovered Tu from Library A | Recovered Tu from Library B |
|---|---|---|---|---|
| 1 | 1 | Incubation at 60° C. for six hours | 0 | 100 |
| 2 | 1 | Incubation at 60° C. for 18 hours | 30 | 100 |
| 3 | 1 | Room temperature, Recovery with ligand | $1 \times 10^{11}$ | $5 \times 10^{10}$ |
| 4 | 1 | Room temperature, Recovery without ligand | 0 | 0 |
| 5 | 4 | Incubation at 80° C. for twenty minutes | 8 | 20 |
| 6 | 4 | Room temperature, Recovery with ligand | $1 \times 10^{10}$ | $3 \times 10^{10}$ |
| 7 | 4 | Room temperature, Recovery without ligand | 0 | $4 \times 10^3$ |
| 8 | 9 | Trypsin 100 μg/ml 37° C. for 6 hours in PBS | $1 \times 10^9$ | $3 \times 10^8$ |
| 9 | 9 | Trypsin 100 μg/ml 37° C. for 18 hours in PBS | $2 \times 10^7$ | $3 \times 10^3$ |
| 10 | 9 | Room temperature, Recovery with ligand | $5 \times 10^{10}$ | $3 \times 10^{10}$ |
| 11 | 9 | Room temperature, Recovery without ligand | 0 | 1000 |
| 12 | 12 | pH 3.2 at 37° C. for 6 hours | $3 \times 10^9$ | $3 \times 10^9$ |
| 13 | 12 | pH 3.2 at 37° C. for 18 hours | 5000 | $3 \times 10^3$ |
| 14 | 12 | Room temperature, Recovery with ligand | $1 \times 10^{11}$ | $5 \times 10^{10}$ |
| 15 | 12 | Room temperature, Recovery without ligand | $2 \times 10^3$ | $1.0 \times 10^3$ |

Phage outputs from round 2 and round 3 were amplified and subsequently purified and concentrated to $1 \times 10^{13}$ Tu/ml. Bacterial cultures (100 ml), infected with the phage from the selection outputs, were grown and used for recovery of double-stranded phage DNA using Qiagen Midi DNA purification columns (Qiagen).

The dAb inserts from Round 2, selections 1 and 4 of libraries A and B, as well as Round 3 Library A selections 2, 5, 9, 12, 13 and Library B selections 1, 2, 5, 8, 9, 12 and 13 were PCR amplified from the respective phage preparation aliquots using Taq polymerase with primers CE2 and CE3. The amplification products were gel purified and cut with Sal I and Not I restriction enzymes before being cloned into pDOM13 vector for sequencing and expression.

Analysis of Selection Results:

Analysis of pools of DNA sequences of DOM1h-574 variants selected after round 3 from Library B using the above mentioned phage selections, revealed that different selection pressures had preferentially enriched different sets of mutations, as summarized in Table 5. Certain mutations observed are also present in the dAbs used as starting point for selections, i.e. 30V and 62 A are present in DOM1h-574-180, 30V is present in DOM1h-574-109 and 100 A is present in DOM1h-574-138.

TABLE 5

Summary indicating the positions and changes most frequently found for each selection condition. The number of '+' are indicative of the relative frequency of that amino-acid residue. Numbering according to Kabat.

|         | 30D | 30S | 30V | 37I | 62A | 94V | 100E | 100A |
|---------|-----|-----|-----|-----|-----|-----|------|------|
| 65° C.  | ++  | ++  | ++  |     | +   |     | ++   | ++   |
| 80° C.  |     | ++  |     |     |     |     | ++   |      |
| Trypsin |     |     |     | +++ |     | +++ |      | +++  |
| pH      |     | +++ |     |     |     |     | ++   | +    |

Example 3

Characterisation of Selected dAbs

Figure 1D:
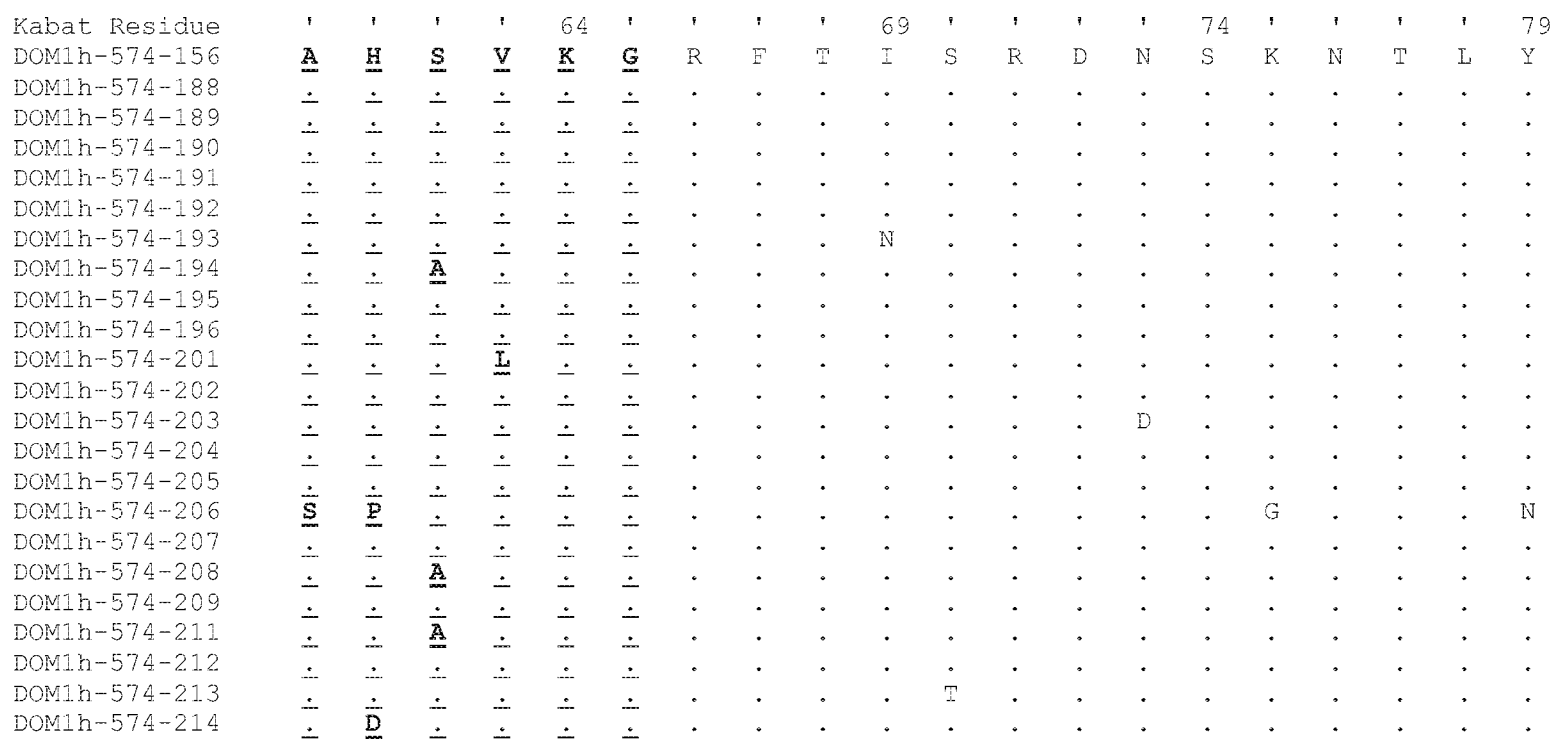
Figure 1E:
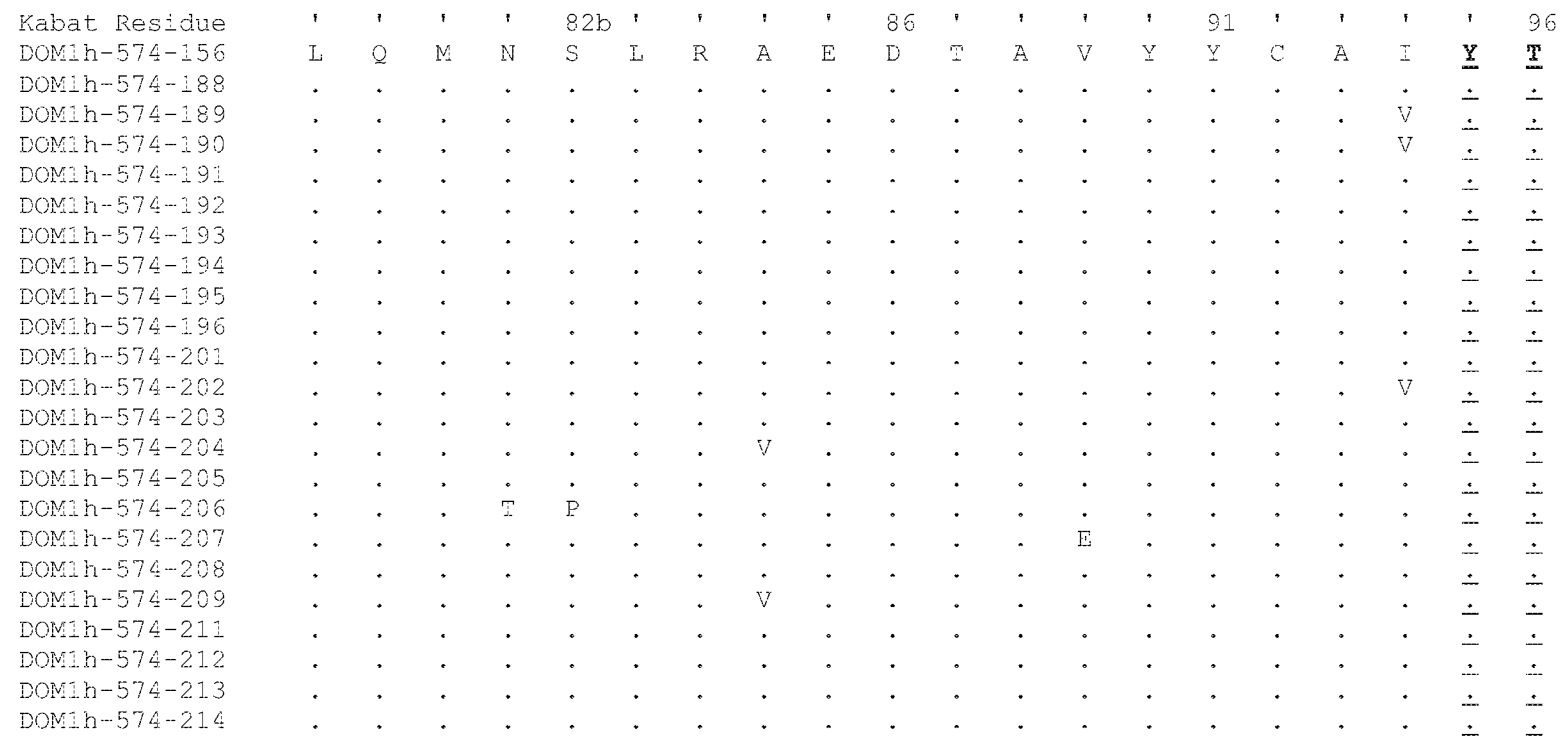

Using the information from the DNA sequence analysis, a subset of anti-TNFR1 dAbs were selected, summarised in Table 6, which combined different mutations as shown in FIG. 1. For further characterisation, these dAbs were expressed in *E. coli*, purified from the supernatant using batch binding to Protein-A Streamline and buffer exchanged to PBS. To facilitate the screening process, the accelerated stability testing was slightly modified from the earlier described method.

For the accelerated stability testing, the reactions were carried out in a PCR plate incubated in a thermal cycler for the desired period of time:

d) 100 μl of 1 mg/ml dAb in PBS is dispensed into the wells of a PCR plate.
e) The protein is incubated for 40 hours at either 40° C. or 50° C.
f) An aliquot of 50 μl is removed and the $OD_{320}$ is measured in a microplate reader (Molecular Devices) and returned to the reaction vessel after measurement. Higher readings indicate aggregate formation. Determination of $OD_{320}$ is used as this is best suited for determination of precipitation and aggregation, whereas $OD_{280}$ is best used for determination of protein concentration in solution.

The results of this screen are summarised in Table 6. This analysis highlights numerous dAbs with significant increases in accelerated stability compared to DOM1h-574-156 when measured at 40 degrees centigrade. Whereas the starting clone, DOM1h-574-156 gives an absorbance of 1.08 at 320 nm after 40 h at 40° C., indicating that a significant amount of protein has precipitated, many of the novel dAbs have low reads (<0.5), indicating that a large portion of the protein is still in solution. The most pronounced increases in accelerated stability at 40° C. for 40 h, are observed for DOM1h-574-188, DOM1h-574-191, DOM1h-574-192, DOM1h-574-196, DOM1h-574-201, DOM1h-574-204, DOM1h-574-205, DOM1h-574-206 and DOM1h-574-208.

TABLE 6

Novel dAbs tested for accelerated stability. For each dAb it is indicated from which library it originated as well as the selection conditions used to identify this dAb. Purified dAbs (1 mg/ml) were tested for accelerated stability through incubation at 40° C. or 50° C. for 40 h in a PCR plate. After incubation, the $OD_{320}$ was determined for each dAb, establishing the level of precipitation in each well. The lower the number the more stable the dAb.

| Clone | Library | Selection pressure | $OD_{320}$, 40 h 40° C. | $OD_{320}$, 48 h 50° C. |
|-------|---------|--------------------|-----------------------|-----------------------|
| PBS   |         |                    | 0.15                  | 0.15                  |
| DOM1h-574-156 |   | Parent clone       | 1.08                  | 2                     |
| DOM1h-574-188 | B | 65° C.             | 0.37                  |                       |
| DOM1h-574-189 | B | 80° C.             | 0.7                   |                       |
| DOM1h-574-190 | B | trypsin            | 0.94                  | 2                     |
| DOM1h-574-191 | B | pH 3.2, 6 h        | 0.37                  | 1.6                   |
| DOM1h-574-192 | B | pH 3.2, 18 h       | 0.4                   | 2                     |
| DOM1h-574-193 | B | 65° C., 18 h       | 2.0                   |                       |
| DOM1h-574-194 | B | 65° C., 18 h       | 1.3                   |                       |
| DOM1h-574-195 | B | 65° C.             | 0.87                  |                       |
| DOM1h-574-196 | B | pH 3.2             | 0.35                  |                       |
| DOM1h-574-201 | A | 80° C.             | 0.31                  | 1.9                   |
| DOM1h-574-202 | A | 80° C.             | 0.57                  |                       |
| DOM1h-574-203 | A | 80° C.             | 0.52                  | 2.25                  |
| DOM1h-574-204 | A | trypsin            | 0.25                  |                       |
| DOM1h-574-205 | A | pH 3.2, 6 h        | 0.24                  | 1.6                   |
| DOM1h-574-206 | A | pH 3.2, 6 h        | 0.28                  | 2.1                   |
| DOM1h-574-208 | A | 80° C.             | 0.38                  | 1.65                  |
| DOM1h-574-209 | A | trypsin            |                       | 1.98                  |
| DOM1h-574-211 | A | pH 3.2, 18 h       |                       | 2                     |
| DOM1h-574-212 | A | pH 3.2, 6 h        |                       | 2.1                   |
| DOM1h-574-213 | A | pH 3.2, 18 h       |                       | 1.5                   |
| DOM1h-574-214 | A | pH 3.2, 18 h       |                       | 0.4                   |

DOM1h-574-207 was tested in a Tris-gylycine buffer and it was more stable than DOM1h-574-156.

Example 4

Stable Anti-TNFR1 dAbs are Functionally Active

To confirm the increase in accelerated stability four novel dAbs were also characterised according to the more extensive protocol described in example 1. In this protocol, the dAbs are incubated up to 48 h at 40° C., centrifuged and the remaining dAb in solution quantified using $OD_{280}$. The dAbs tested were DOM1h-574-188, DOM1h-574-196, DOM1h-574-208 and DOM1h-574-214 and the results are summarised in Table 7. Clearly, these dAbs are significantly more stable compared to the starting dAb DOM1h-574-156 (historical data), as no loss of protein is observed during the first 48 h at 40° C. To verify that the increase in stability is not at the expense of functional anti-TNFR1 activity of the dAb, the binding affinity to TNFR1 of the dAbs was determined by BIAcore, using biotinylated TNFR1 captured on a BIAcore SA chip. Although the affinity for human TNFR1 of these novel dAbs is slightly lower than that described previously for the DOM1h-574-156 dAb (150 pM), it remains within 4-fold of the parent dAb. Therefore, these dAbs combine an increase in accelerated stability without compromising much on the affinity of the dAb for TNFR1.

TABLE 7

Accelerated stability and affinity for human sTNFR1 for novel anti-TNFR1 dAbs. Purified dAb was incubated at 1 mg/ml in PBS at 40° C. for the indicated amounts of time. After that time, the percentage of residual protein in solution was determined by OD280 determination. Affinity for sTNFR1 was determined by BIAcore using coated sTNFR1 and injecting the dAb as described.

| dAb | % in solution | | | | BIAcore |
| --- | --- | --- | --- | --- | --- |
|  | 0.0 h | 2 h | 24 h | 48 h | Kd (nM) |
| DOM1h-574-188 | 100 | 98 | 102 | 101 | 0.35 |
| DOM1h-574-196 | 100 | 102 | 98 | 100 | 0.47 |
| DOM1h-574-208 | 100 | 98 | 103 | 100 | 0.27 |
| DOM1h-574-214 | 100 | 99 | 100 | 99 | 0.58 |

Example 5

Construction of Genetic Fusions of Stable Anti-TNFR1 Dabs with AlbudAbs

To extend the serum half-life of the anti-TNFR1 dAbs, they were fused with the albumin-binding dAb DOM7h-11-3. The four stable anti-TNFR1 dAbs chosen were DOM1h-574-188, DOM1h-574-196, DOM1h-574-208 and DOM1h-574-214 and fusion with DOM7h-11-3 used Ala-Ser-Thr linker sequence. The construction of these fusion molecules was done in two steps. Firstly, the anti-TNFR1 dAbs were amplified by PCR using primers AS9 and OA154, the purified, reaction product was then digested with SalI/NheI, gel purified and ligated in a SalI/NheI digested pDOM13 vector containing the linker and DOM7h-11-3. After ligation, the DNA was transformed to XL10-Gold (Stratagene) cells and colonies were picked for sequence analysis. After sequence confirmation of this construct, the second step of construction was done by amplifying the anti-TNFR1/anti-Albumin cassette using the oligonucleotides JAL102 and AS65. The reaction products were digested with the restriction enzymes Nde I/Not I and run on an agarose gel and purified by gel extraction. The purified DNA fragment containing the fusion product was then cloned into Nde I/Not I-cut pET30a vector (Merck). Cloning in this vector was done to enable expression of the protein using IPTG induction in a fermentor and will result in the dAb being processed without any leading amino-acid residues. This is in contrast to the pDOM13 vector which will add Ser-Thr at the N-terminus of all dAbs expressed in this vector. The following anti-TNFR1 dAb/DOM7h-11-3 fusions were constructed in pET30a:

| Clone Name | Anti-TNFR1 dAb | linker | Anti-albumin dAb |
| --- | --- | --- | --- |
| DMS5535 | DOM1h-574-196 | Ala-Ser-Thr | DOM7h-11-3 |
| DMS5541 | DOM1h-574-208 | Ala-Ser-Thr | DOM7h-11-3 |
| DMS5542 | DOM1h-574-214 | Ala-Ser-Thr | DOM7h-11-3 |
| DMS5544 | DOM1h-574-188 | Ala-Ser-Thr | DOM7h-11-3 |

For expression the constructs were transformed to the *E. coli* strain BL21(DE3) with pECO-1pgl as described in Aon et al. 2008. All four constructs were then expressed in a fermentor using growth at 23° C. post induction and expression was induced with 0.01 mM IPTG. All fermentations were to high cell density in minimal medium at the 5 L scale.

Periplasmic extract was prepared in the following way. Frozen cell paste was defrosted and mixed with 0.5M GuHcl, 200 mM Tris pH8, 10 mM EDTA at 37° C. overnight before centrifuging for 1 hour at 4500 g and discarding the pellet. Purification from the periplasm was by batch binding to Protein-A followed by elution with 100 mM Glycine pH2 and neutralization with 200 mM Tris pH8. Eluted protein was buffer-exchanged to PBS and concentrated before functional characterization.

Example 6

Characterisation of Anti-TNFR1/Anti-Albumin Fusions

The purified protein for DMS5535, DMS5541, DMS5542 and DMS5544 was then characterised in a series of tests to demonstrate that these molecules are both stable and have good anti-TNFR1 activity.

Accelerated Stability Characterisation

To evaluate the biophysical properties of the molecules, the fusions proteins were tested for accelerated stability. As the molecules are expected to be significantly more stable, testing for accelerated stability was done at 1 mg/ml in PBS for 28 days at 40° C., instead of 2 days. The results are summarised in Table 8. From the results it can be concluded that all constructs are very stable with no loss of protein as determined by OD280 after 28 days. The slight increase of protein observed is most likely due to the error within this method of detection and is not significant.

TABLE 8

Summary of accelerated stability and functional characterisation of genetic anti-TNFR1/anti-albumin fusions. Accelerated stability was quantified as the percentage of fusion-protein in solution after 28 days at 40 degrees centigrade as determined by OD280. BIAcore ™ affinities (KD) were determined by injecting at least six different concentrations of anti-TNFR1/AlbudAb ™ (an AlbudAb is an anti-serum albumin dAb). This procedure was performed in two independent experiments and the values of these experiments were averaged, generating the quoted standard deviation (SD). Potency of anti-TNFR1/Albudab fusions was determined in the HUVEC cell assay. Mean EC50 values were calculated from a total of 7 experiments for the anti-TNFR1/Albudab fusions.

| Clone name | % in solution after 28 days at 40° C. | KD (pM) ± SD | Mean EC50 (nM) ± SE |
| --- | --- | --- | --- |
| DMS5535 | 104 | 277 ± 62 | 5.79 ± 0.69 |
| DMS5541 | 106 | 163 ± 74 | 3.58 ± 0.45 |
| DMS5542 | 103 | 202 ± 30 | 6.23 ± 1.05 |
| DMS5544 | 108 | 180 ± 24 | 4.83 ± 0.94 |

S.E = standard error of the mean.

Functional Characterisation of Anti-TNFR1/Anti-Albumin Protein

To ensure that the functional anti-TNFR1 activity of the molecule is not impaired, the four genetic fusions of anti-TNFR1/anti-albumin were tested in functional assays to determine both their affinity for TNFR1 and their potency in inhibiting TNFα induced signalling.

TNFR1 Affinity-BIAcore

The affinity of the anti-TNFR1/AlbudAb fusions for human TNFR1 was determined by BIAcore. Briefly, the anti-TNFR1 molecules were injected over a streptavidin BIAcore chip on which biotinylated, human TNFR1 had been immobilised. Association and dissociation were determined at different concentrations of injected anti-TNFR1. The results of this characterisation are summarised in Table 8, and indicate that the molecules are high affinity binders of human TNFR1 (KD<280 pM). The affinity for human TNFR1 as determined by BIAcore of the anti-TNFR1/AlbudAb fusion is slightly higher to that determined for the single anti-TNFR1 dAb used in each of the combination constructs.

Potency in HUVEC Cell Assay

A second functional assay to determine the anti-TNFR1 activity of the dAbs is the HUVEC assay. Briefly, in this assay HUVECs are pre-incubated for 1 h with the dAb followed by stimulation with 1 ng/ml of TNFα. This stimulation leads to an increase of VCAM expression on the cell, which can be determined. The level of inhibition of TNFα-induced VCAM expression provided by the dAb is determined by plotting dAb concentration against VCAM expression.

The results are summarised in Table 8 and demonstrate that the anti-TNFR1/AlbudAb fusions have single-digit nM potency in this HUVEC assay.

In conclusion, by performing phage display selections of mutant libraries under harsh selection conditions, we have been able to identify novel anti-TNFR1 dAbs. These dAbs combine high affinity for TNFR1, as determined by BIAcore, with increased accelerated stability. Furthermore, the binding properties are maintained when these dAbs are fused with another protein or peptide, as exemplified by the DOM7h-11-3 AlbudAb, and the stability is further increased. These dAbs represent a significant improvement and the novel properties of the dAbs ought to improve the developability of these dAbs as therapeutic agents.

BIAcore Protocol

The binding affinities for binding to recombinant human TNFR1 were assessed by BIAcore™ analysis. Analysis was carried out using Streptavidin coated (SA) chips (BIAcore, cat no. BR-1000-32). An SA chip was coated at low density using biotinylated hTNFR1. Examined molecules were injected over this surface at seven concentrations, i.e. 32, 16 (twice), 8, 4, 2, 1 and 0.5 nM, in random order using a flow rate of 50 µl/min. Between individual injections the surface was regenerated back to baseline using 10 mM glycine pH 2.0. Data were corrected for instrument artefacts using double referencing. Experiments were carried out on a BIAcore™ 3000 machine and data were analysed using the BIAevaluation software version 4.1, $k_{on}$ and $k_{off}$ were simultaneously fitted using 1:1 Langmuir binding model. For fitting purposes, the concentration range 1-32 nM was used for the monomers, while 0.5-16 nM was used for the AlbudAb fusion molecules. The binding data fitted well to the 1:1 model for all tested molecules. All $K_D$ values were calculated from $k_{on}$ and $k_{off}$ rates. BIAcore™ runs were carried out at 25° C.

HUVEC Cell Assay Protocol

Human umbilical vein endothelial cells (HUVECs) respond to TNF-α treatment by upregulating the expression of VCAM-1. Anti-TNFR1 dAbs inhibit the action of TNF-α, therefore a reduction in VCAM-1 expression can be seen by HUVE cells in the presence of anti-TNFR1 dAbs. To assess this inhibition, briefly, normal pooled HUVEC cells (Promocell # C-12203) are plated out in gelatine coated 96 well microtitre plates (VWR #734-0403) (4×10⁴ cells/well) in endothelial cell growth media (Promocell # C-22110). Cells are left to adhere overnight (37° C./5% $CO_2$) before a dose range of dAb or media only is added to the cells and plates are left at 37° C./5% $CO_2$ for an hour. A fixed concentration of TNF-α (1 ng/ml, Peprotech #300-01A) is then added to the cells which are incubated for a further 23 hours (37° C./5% $CO_2$). As a negative control, cells are incubated with media only, and for the positive control, cells are incubated with TNF-α only.

Following incubation, the cell culture supernatant is aspirated and the cells washed three times in ice cold PBS. Cells are lysed by the addition of 75 µl/well ice cold Tris-Glycerol lysis buffer (40 mM Tris, 274 mM NaCl, 2% Triton-X-100, 20% Glycerol, 50 mM NaF, 1 mM $Na_3VO_4$, 1× protease inhibitor tablet per 10 mls (Roche #11-836-170-001)) and incubated for 15 mins on ice. The cell lysates are then transferred to a VCAM-1 sandwich ELISA.

For the VCAM-1 sandwich ELISA, F96 Maxisorp immunoplates (Nunc #439454) are coated overnight at 4° C. with anti-VCAM-1 mAb (R&D systems # MAB809, 2 ug/ml), 100 ul/well in PBS. The next day, plates are washed and blocked with 1% BSA/PBS (200 ul/well) for 1 hour before the addition of the HUVE cell lysates (50 ul/well). Plates are incubated with the lysates for 2 hours and washed again before the addition of biotinylated anti-VCAM-1 polyclonal Ab (R&D systems # BAF809) 0.4 ug/ml in 0.1% BSA/PBS, 0.05% Tween-20, 100 ul/well and incubation for a further hour. Plates are washed again before the addition of Streptavidin-HRP (diluted according to manufacturers instructions in 0.1% BSA/PBS, 0.05% Tween), 100 ul/well. Bound streptavidin-HRP is visualised by the addition of Sureblue TMB-1 peroxidase substrate (KPL-#52-00-00) and the reaction is stopped by the addition of 1M HCl. Absorbance is read immediately on a SpectraMax M5$^e$ plate reader (Molecular Devices) at 450 nm.

Raw OD values are exported into Microsoft Excel and background OD values (cells incubated with media only) are subtracted from all data points. To calculate inhibition of TNF-α induced VCAM-1 upregulation by the cells, the percentage inhibition of maximal VCAM-1 expression (as shown by the positive control) at each concentration of dAb is calculated using the following formula;

% inhibition of Maximal VCAM-1 upregulation=100− (OD value at a particular dAb dilution/OD value of positive control)*100.

dAb concentration values are then plotted against percentage inhibition in GraphPad Prism and concentration effect curves and potency ($EC_{50}$) values are determined using a sigmoidal dose response curve with variable slope.

The concentration of TNF-α used to stimulate the cells is approximately 70% (EC70) of the maximal response to TNF-α by the cells.

REFERENCES

Aon J C, Caimi R J, Taylor A H, Lu Q, Oluboyede F, Dally J, Kessler M D, Kerrigan J J, Lewis T S, Wysocki L A, Patel P S. Suppressing posttranslational gluconoylation of heterologous proteins by metabolic engineering of *Escherichia coli*. Appl Environ Microbiol. 2008 February; 74(4): 950-8. Epub 2007 Dec. 14.

SEQUENCE LISTING

All nucleotide sequences are written 5' to 3' and all amino acid sequences are written N- to C-terminally.

DOM1h-131-206 is disclosed in WO2008149148 (the amino acid sequence of which and the nucleotide sequence of which, as disclosed in that PCT application, are expressly incorporated herein by reference as though explicitly written herein and for use with the present invention, and it is contemplated that any part of such disclosure can be incorporated into one or more claims herein).

Oligonucleotides used:

AS9: CAGGAAACAGCTATGACCATG (SEQ ID NO: 1)

AS339: TTCAGGCTGCGCAACTGTTG (SEQ ID NO: 2)

AS639: CGCCAAGCTTGCATGCAAATTC (SEQ ID NO: 3)

AS65: TTGTAAAACGACGGCCAGTG (SEQ ID NO: 4)

CE2: CTTAAACAGCTTGATACCG (SEQ ID NO: 5)

CE3: GACAGCCCTCATAGTTAG (SEQ ID NO: 6)

OA154: TTCTTTTGCTAGCGCTCGAGACGGTGACCAGGGTTC (SEQ ID NO: 7)

JAL102: (SEQ ID NO: 8)
GGAATTCCATATGAAATACCTGCTGCCGACCGCTGCTGCTGGTCTGCTGCTC

CTCGCTGCCCAGCCGGCGATGGCCGAGGTGCAGCTGTTGGAGTCTGGGGG

Nucleotide sequences:
>DOM1h-574-188
 (SEQ ID NO: 9)
GAGGTGCAGCTGTTGGAGTCTGGGGGAGGCTTGGTACAGCCTGGGGGGTCC

CTGCGTCTCTCCTGTGCAGCCTCCGGATTCACCTTTGATAAGTATTCAATGG

GGTGGGTCCGCCAGGCTCCAGGGAAGGGTCTAGAGTGGGTCTCACAGATTT

CGGATACTGCTGATCGTACATACTACGCACACTCCGTGAAGGGCCGGTTCA

CCATCTCCCGCGACAATTCCAAGAACACGCTGTATCTGCAAATGAACAGCC

TGCGTGCTGAGGACACCGCGGTATATTACTGTGCGATATATACTGGGCGTTG

GGTGCCTTTTGAGTACTGGGGTCAGGGAACCCTGGTCACCGTCTCGAGC

>DOM1h-574-189
 (SEQ ID NO: 10)
GAGGTGCAGCTGTTGGAGTCTGGGGGAGGCTTGGTACAGCCTGGGGGGTCC

CTGCGTCTCTCCTGTGCAGCCTCCGGATTCACCTTTTTCAAGTATTCGATGGG

GTGGGTCCGCCAGGCTCCAGGGAAGGGTCTAGAGTGGGTCTCACAGATTTC

GGATACTGCTGATCGTACATACTACGCACACTCCGTGAAGGGCCGGTTCAC

CATCTCCCGCGACAATTCCAAGAACACGCTGTATCTGCAAATGAACAGCCT

GCGTGCTGAGGACACCGCGGTTTATTACTGTGCGGTATATACTGGGCGTTGG

GAGCCTTTTGAGTACTGGGGTCAGGGAACCCTGGTCACCGTCTCGAGC

>DOM1h-574-190
 (SEQ ID NO: 11)
GAGGTGCAGCTGTTGGAGTCTGGGGGAGGCTTGGTACAGCCTGGGGGGTCC

CTGCGTCTCTCCTGTGCAGCCTCCGGATTCACCTTTTTCAAGTATTCGATGGG

GTGGATCCGCCAGGCTCCAGGTAAGGGTCTAGAGTGGGTCTCACAGATTTC

GGATACTGCTGATCGTACATACTACGCACACTCCGTGAAGGGCCGGTTCAC

CATCTCCCGCGACAATTCCAAGAACACGCTGTATCTGCAAATGAACAGCCT

GCGTGCCGAGGACACCGCGGTATATTACTGTGCGGTATATACGGGTCGGTG

GGCGCCTTTTGAGTACTGGGGTCAGGGAACCCTGGTCACCGTCTCGAGC

-continued

>DOM1h-574-191
(SEQ ID NO: 12)
GAGGTGCAGCTGTTGGAGTCTGGGGGAGGCTTGGTACAGCCTGGGGGGTCC

CTGCGTCTCTCCTGTGCAGCCTCCGGATTCACATTTTCCAAGTATTCGATGG

GGTGGGTCCGCCAGGCTCCAGGGAAGGGTCTAGAGTGGGTCTCACAGATTT

CGGATACTGCTGATCGTACATACTACGCACACTCCGTGAAGGGCCGGTTCA

CCATCTCCCGCGACAATTCCAAGAACACGCTGTATCTGCAAATGAACAGCC

TGCGTGCTGAGGACACCGCGGTATATTACTGTGCGATATATACTGGGCGTTG

GGTGCCTTTTGAGTACTGGGGTCAGGGAACCCTGGTCACCGTCTCGAGC

>DOM1h-574-192
(SEQ ID NO: 13)
GAGGTGCAGCTGTTGGAGTCTGGGGGAGGCTTGGTACAGCCTGGGGGGTCC

CTGCGTCTCTCCTGTGCAGCCTCCGGATTCACCTTTTCCAAGTATTCGATGG

GGTGGGTCCGCCAGGCTCCAGGGAAGGGTCTAGAGTGGGTCTCACAGATTT

CGGATACTGCTGATCGTACATACTACGCACACTCCGTGAAGGGCCGGTTCA

CCATCTCCCGCGACAATTCCAAGAACACGCTGTATCTGCAAATGAACAGCC

TGCGTGCTGAGGACACCGCGGTATATTACTGTGCGATATATACTGGGCGTTG

GGTGCCTTTTGAGAACTGGGGTCAGGGAACCCTGGTCACCGTCTCGAGC

>DOM1h-574-193
(SEQ ID NO: 14)
GAGGTGCAGCTGTTGGAGTCTGGGGGAGGCTTGGTACAGCCTGGGGGGTCC

CTCCGTCTCTCCTGTGCAGCCTCCGGATTCACCTTTGATAAGTATTCGATGG

GGTGGGTCCGCCAGGCTCCAGGGAAGGGTCCAGAGTGGGTCTCACAGATTT

CGGATACTGCTGATCGTACATACTACGCACACTCCGTGAAGGGCCGGTTCA

CCAACTCCCGCGACAATTCCAAGAACACGCTGTATCTGCAAATGAACAGCC

TGCGTGCTGAGGACACCGCGGTATATTACTGTGCGATATATACTGGGCGTTG

GGAGCCTTTTGAGTACTGGGGTCAGGGAACCCTGGTCACCGTCTCGAGC

>DOM1h-574-194
(SEQ ID NO: 15)
GAGGTGCAGCTGTTGGAGTCTGGGGGAGGCTTGGTACAGCCTGGGGGGTCC

CTGCGTCTCTCCTGTGCAGCCTCCGGATTCACCTTTGTTAAGTATTCGATGG

GGTGGGTCCGCCAGGCTCCAGGGAAGGGTCTAGAGTGGGTCTCACAGATTT

CGGATACTGCTGATCGTACATACTACGCACACGCGGTGAAGGGCCGGTTCA

CCATCTCCCGCGACAATTCCAAGAACACGCTGTATCTGCAAATGAACAGCC

TGCGTGCTGAGGACACCGCGGTATATTACTGTGCGATATATACTGGGCGTTG

GGTGCCATTTGAGTACTGGGGTCAGGGAACCCTGGTCACCGTCTCGAGC

>DOM1h-574-195
(SEQ ID NO: 16)
GAGGTGCAGCTGTTGGAGTCTGGGGGAGGCTTGGTACAGCCTGGGGGGTCC

CTGCGTCTCTCCTGTGCAGCCTCCGGATTCACCTTTTTCAAGTATTCGATGGG

GTGGGTCCGCCAGGCTCCTGGGAAGGGTCTAGAGTGGGTCTCACAGATTTC

GGATACTGCTGATCGTACATACTACGCACACTCCGTGAAGGGCCGGTTCAC

CATCTCCCGCGACAATTCCAAGAACACGCTGTATCTGCAAATGAACAGCCT

GCGTGCTGAGGACACCGCGGTATATTACTGTGCGATATATACTGGGCGCTG

GGAGCCTTTTGAGTACTGGGGACAGGGAACCCTGGTCACCGTCTCGAGC

-continued

>DOM1h-574-196

(SEQ ID NO: 17)

GAGGTGCAGCTGTTGGAGTCTGGGGGAGGCTTGGTACAGCCTGGGGGGTCC

CTGCGTCTCTCCTGTGCAGCCTCCGGATTCACCTTTTCCAAGTATTCGATGG

GGTGGGTCCGCCAGGCTCCAGGGAAGGGTCTAGAGTGGGTCTCACAGATTT

CGGATACTGCTGATCGTACATACTACGCACACTCCGTGAAGGGCCGGTTCA

CCATCTCCCGCGACAATTCCAAGAACACGCTGTATCTGCAAATGAACAGCC

TGCGTGCTGAGGACACCGCGGTATATTACTGTGCGATATATACTGGGCGTTG

GGAGCCTTTTGAGTACTGGGGTCAGGGAACCCTGGTCACCGTCTCGAGC

>DOM1h-574-201

(SEQ ID NO: 18)

GAGGTGCAGCTGTTGGAGTCTGGGGGAGGCTTGGTACAGCCTGGGGGGTCC

CTGCGTCTCTCCTGTGCAGCCTCCGGATTCACCTTTGATAAGAATTCGATGG

GGTGGGTCCGCCAGGCTCCAGGGAAGGGTCTAGAGTGGGTCTCACAGATAT

CGGATACAGCTGATCGTACATACTACGCACACTCACTGAAGGGCCGGTTCA

CCATCTCCCGCGACAATTCCAAGAACACGCTGTATCTGCAAATGAACAGCC

TGCGTGCTGAGGACACCGCGGTATATTACTGTGCGATATATACTGGGCGTTG

GGTGCCTTTTGAGTACTGGGGTCAGGGAACCCTGGTCACCGTCTCGAGC

>DOM1h-574-202

(SEQ ID NO: 19)

GAGGTGCAGCTGTTGGAGTCTGGGGGAGGCTTGGTACAGCCTGGGGGGTCC

CTGCGTCTCTCCTGTGCAGCCTCCGGATTCACCTTTTTCAAGTATTCGATGGG

GTGGGTCCGCCAGGCTCCAGGGAAGGGTCTAGAGTGGGTATCACAGATATC

GGATACTGCTGATCGTACATACTACGCACACTCCGTGAAGGGCCGGTTCAC

CATCTCCCGCGACAATTCCAAGAACACGCTGTATCTGCAAATGAACAGCCT

GCGTGCCGAGGACACCGCGGTATATTACTGTGCGGTATATACGGGTCGGTG

GGCGCCTTTTGAGTACTGGGGTCAGGGAACCCTGGTCACCGTCTCGAGC

>DOM1h-574-203

(SEQ ID NO: 20)

GAGGTGCAGCTGTTGGAGTCTGGGGGAGGCTTGGTACAGCCTGGGGGGTCC

CTGCGTCTCTCCTGTGCAGCCTCCGGATTCACCTTTTTCAAGTATTCGATGGG

GTGGGTCCGCCAGGCTCCAGGGAAGGGTCTAGAGTGGGTCTCACAGATTTC

GGATACTGCTGATCGTACATACTACGCACACTCCGTGAAGGGCCGGTTCAC

CATCTCCCGCGACGATTCCAAGAACACGCTGTATCTGCAAATGAACAGCCT

GCGCGCCGAGGACACCGCGGTATATTACTGCGCGATATATACGGGTCGGTG

GGCGCCTTTTGAGTACTGGGGTCAGGGAACCCTGGTCACCGTCTCGAGC

>DOM1h-574-204

(SEQ ID NO: 21)

GAGGTGCAGCTGTTGGAGTCTGGGGGAGGCTTGGTACAGCCTGGGGGGTCC

CTGCGTCTCTCCTGTGCAGCCTCCGGATTCACCTTTTTCAAGTATTCGATGGG

GTGGGTCCGCCAGGCTCCAGGGAAGGGTCTAGAGTGGGTCTCACAGATTTC

GGATACTGCTGATCGTACATACTACGCACACTCCGTGAAGGGCCGGTTCAC

CATCTCCCGCGACAATTCCAAGAACACGCTGTATCTGCAAATGAACAGCCT

GCGTGTCGAGGACACCGCGGTATATTACTGTGCGATATATACGGGTCAGTG

GGCGCCTTATGAGTACTGGGGTCAGGGAACCCTGGTCACCGTTCGAGCG

>DOM1h-574-205

(SEQ ID NO: 22)
GAGGTGCAGCTGTTGGAGTCTGGGGGAGGCTTGGTACAGCCTGGGGGGTCC

CTGCGTCTCTCCTGTGCAGCCTCCGGATTCACCTTTGATAAGTATTCGATGG

GGTGGGTCCGCCAGGCTCCAGGGAAGGATCTAGAGTGGGTCTCACAGATTT

CGGATACTGCTGACCGTACATACTACGCACACTCCGTGAAGGGCCGGTTCA

CCATCTCCCGCGACAATTCCAAGAACACGCTGTATCTGCAAATGAACAGTCT

GCGTGCTGAGGACACCGCGGTATATTACTGTGCGATATATACTGGGCGTTG

GGTGCCTTTTGAGAACTGGGGTCACGGAACCCTGGTCACCGTCTCGAGC

>DOM1h-574-206

(SEQ ID NO: 23)
GAGGTGCAGTTGTTGGATTCTGGGGGAGGCTTGGTACAGCCTGGGGGGTCC

CTGCGTCTCTCCTGTGCAGCCTCCGGATTCACCTTTTTCAAGTATTCGATGGG

GTGGGTCCGCCAGGCTCCAGGGAAGGGTCTAGAGTGGGTCTCACAGATTTC

GGATACTGCTGATCGTACATACTACTCACCCTCCGTGAAGGGCCGGTTCACC

ATCTCCCGCGACAATTCCGGGAACACGCTGAATCTGCAAATGACCCCCCTG

CGTGCTGAGGACACCGCGGTATATTACTGTGCGATATATACTGGGCGTTGG

GAGCCTTTTGAGTACTGGGGTCAGGGAACCCTGGTCACCGTCTCGAGC

>DOM1h-574-207

(SEQ ID NO: 24)
GAGGTGCAGCTGTTGGAGTCTGGGGGAGGCATGGTACAGCCGGGGGGGTCC

CTGCGTCTCTCCTGTGCATCCTCCGGATTCACCTTTTCCAAGTATTCGATGGG

GTGGGTCCGCCAGGCTCCAGGGAAAGGTCTAGAGTGGGTCTCACAGATTTC

CGATACTGCTGATCTTACATACTACGCACACTCCGTGAAGGGCCGGTTCACC

ATCTCCCGCGACAATTCCAAGAACACGCTGTATCTGCAAATGAACAGCCTG

CGTGCCGAGGACACCGCGGAATATTACTGTGCGATATATACGGGTCGGTGG

GCGCCTTTTGAGTACTGGGGTCAGGGAACCCTGGTCaCCGTCTCGAGC

>DOM1h-574-208

(SEQ ID NO: 25)
GAGGTGCAGCTGTTGGAGTCTGGGGGAGGCTTGGTACAGCCTGGGGGGTCC

CTGCGTCTCTCCTGTGCAGCCTCCGGATTCACCTTTGATAAGTATTCGATGGG

GGTGGGTCCGCCAGGCTCCAGGGAAGGGTCTAGAGTGGGTCTCACAGATTT

CGGATACTGCTGATCGTACATACTACGCACACGCGGTGAAGGGCCGGTTCA

CCATCTCCCGCGACAATTCCAAGAACACGCTGTATCTGCAAATGAACAGCC

TGCGTGCTGAGGACACCGCGGTATATTACTGTGCGATATATACTGGGCGTTG

GGTGCCTTTTGAGTACTGGGGTCAGGGAACCCTGGTCACCGTCTCGAGC

>DOM1h-574-209

(SEQ ID NO: 26)
GAGGTGCAGCTGTTGGAGTCTGGGGGAGGCTTGGTACAGCCTGGGGGGTCC

CTGCGTCTCTCCTGTGCAGCCTCCGGATTCACCTTTTTCAAGTATTCGATGGG

GTGGGTCCGCCAGGCTCCAGGGAAGGGTCTAGAGTGGGTCTCACAGATTTC

GGATACTGCTGATCGTACATACTACGCACACTCCGTGAAGGGCCGGTTCAC

CATCTCCCGCGACAATTCCAAGAACACGCTGTATCTGCAAATGAACAGCCT

GCGTGTCGAGGACACCGCGGTATATTACTGTGCGATATATACGGGTCAGTG

GGCGCCTTATGAGTACTGGGGTCAGGGAACCCTGGTCACCGTCTCGAGC

>DOM1h-574-211
(SEQ ID NO: 27)
GAGGTGCAGCTGTTGGAGTCTGGGGGAGGCTTGGTACAGCCTGGGGGGTCC

CTGCGTCTCTCCTGTGCAGCCTCCGGATTCACCTTTGCTAAGTATTCGATGG

GGTGGGTCCGCCAGGCTCCAGGGAAGGGTCTAGAGTGGGTCTCACAGATTT

CGGATACTGCTGATCGTACATACTACGCACACGCGGTGAAGGGCCGGTTCA

CCATCTCCCGCGACAATTCCAAGAACACGCTGTATCTGCAAATGAACAGCC

TGCGTGCTGAGGACACCGCGGTATATTACTGTGCGATATATACTGGGCGTTG

GGTGCCTTTTGAGTACTGGGGTCAGGGAACCCTGGTCACCGTCTCGAGC

>DOM1h-574-212
(SEQ ID NO: 28)
GAGGTGCAGCTGTTGGAGTCTGGGGGAGGCTTGGTACAGCCTGGGGGGTCC

CTGCGTCTCTCCTGTGCAGCCTCCGGATTCACCTTTTCCAAGTATTCGATGG

GGTGGGTCCGCCAGGCTCCAGGGAAGGGTCTAGAGTGGGTCTCACAGATTT

CGGATACTGCTGATCGTACATACTACGCACACTCCGTGAAGGGCCGGTTCA

CCATCTCCCGCGACAATTCCAAGAACACACTGTACCTGCAAATGAACAGCC

TGCGTGCTGAGGACACCGCGGTATATTACTGTGCGATATATACTGGGCGTTG

GGTGCCTTTTGAGTACTGGGGTCAGGGAACCCTGGTCACCGTCTCGAGC

>DOM1h-574-213
(SEQ ID NO: 29)
GAGGTGCAGCTGTTGGAGTCTGGGGGAGGCTTGGTACAGCCTGGGGGGTCC

CTCCGTCTCTCCTGTGCAGCCTCCGGATTCACCTTTGATAAGTATTCGATGG

GGTGGGTCCGCCAGGCTCCAGGGAAGGGTCTAGAGTGGGTCTCACAGATTT

CGGATACTGCTGATCGTACATACTACGCACACTCCGTAAAGGGCCGGTTCA

CCATCACCCGCGACAATTCCAAGAACACGCTGTATCTGCAAATGAACAGCC

TGCGTGCTGAGGACACCGCGGTATATTACTGTGCGATATATACTGGGCGTTG

GGAGCCTTTTGAGTACTGGGGTCAGGGAACCCTGGTCACCGTCTCGAGC

>DOM1h-574-214
(SEQ ID NO: 30)
GAGGTGCAGCTGTTGGAGTCTGGGGGAGGCTTGGTACAGCCCGGGGGGTCC

CTGCGTCTCTCCTGTGCAGCCTCCGGATTCACCTTTTCCAAGTATTCGATGG

GGTGGGTCCGCCAGGCTCCAGGGAAGGGTCTAGAGTGGGTCTCACAGATTT

CGGATACTGCTGATCGTACATACTACGCAGACTCCGTGAAGGGCCGGTTCA

CCATCTCCCGCGACAATTCCAAGAACACGCTGTATCTGCAAATGAACAGCC

TGCGTGCCGAGGACACCGCGGTATATTACTGTGCGATATACACTGGGCGTT

GGGTGCCTTTTGAGTACTGGGGTCAGGGAACCCTGGTCACCGTCTCGAGC

>DMS5535
(SEQ ID NO: 31)
5GAGGTGCAGCTGTTGGAGTCTGGGGGAGGCTTGGTACAGCCTGGGGGGTCC

CTGCGTCTCTCCTGTGCAGCCTCCGGATTCACCTTTTCCAAGTATTCGATGG

GGTGGGTCCGCCAGGCTCCAGGGAAGGGTCTAGAGTGGGTCTCACAGATTT

CGGATACTGCTGATCGTACATACTACGCACACTCCGTGAAGGGCCGGTTCA

CCATCTCCCGCGACAATTCCAAGAACACGCTGTATCTGCAAATGAACAGCC

TGCGTGCTGAGGACACCGCGGTATATTACTGTGCGATATATACTGGGCGTTG

GGAGCCTTTTGAGTACTGGGGTCAGGGAACCCTGGTCACCGTCTCGAGCGC

TAGCACCGACATCCAGATGACCCAGTCTCCATCCTCCCTGTCTGCATCTGTA

-continued

GGAGACCGTGTCACCATCACTTGCCGGGCAAGTCGTCCGATTGGGACGACG

TTAAGTTGGTACCAGCAGAAACCAGGGAAAGCCCCTAAGCTCCTGATCCTT

TGGAATTCCCGTTTGCAAAGTGGGGTCCCATCACGTTTCAGTGGCAGTGGAT

CTGGGACAGATTTCACTCTCACCATCAGCAGTCTGCAACCTGAAGATTTTGC

TACGTACTACTGTGCGCAGGCTGGGACGCATCCTACGACGTTCGGCCAAGG

GACCAAGGTGGAAATCAAACGG

>DMS5541 (SEQ ID NO: 32)
GAGGTGCAGCTGTTGGAGTCTGGGGGAGGCTTGGTACAGCCTGGGGGGTCC

CTGCGTCTCTCCTGTGCAGCCTCCGGATTCACCTTTGATAAGTATTCGATGG

GGTGGGTCCGCCAGGCTCCAGGGAAGGGTCTAGAGTGGGTCTCACAGATTT

CGGATACTGCTGATCGTACATACTACGCACACGCGGTGAAGGGCCGGTTCA

5CCATCTCCCGCGACAATTCCAAGAACACGCTGTATCTGCAAATGAACAGCC

TGCGTGCTGAGGACACCGCGGTATATTACTGTGCGATATATACTGGGCGTTG

GGTGCCTTTTGAGTACTGGGGTCAGGGAACCCTGGTCACCGTCTCGAGCGCT

AGCACCGACATCCAGATGACCCAGTCTCCATCCTCCCTGTCTGCATCTGTAG

GAGACCGTGTCACCATCACTTGCCGGGCAAGTCGTCCGATTGGGACGACGT

TAAGTTGGTACCAGCAGAAACCAGGGAAAGCCCCTAAGCTCCTGATCCTGT

GGAATTCCCGTTTGCAAAGTGGGGTCCCATCACGTTTCAGTGGCAGTGGATC

TGGGACAGATTTCACTCTCACCATCAGCAGTCTGCAACCTGAAGATTTTGCT

ACGTACTACTGTGCGCAGGCTGGGACGCATCCTACGACGTTCGGCCAAGGG

ACCAAGGTGGAAATCAAACGG

>DMS5542 (SEQ ID NO: 33)
GAGGTGCAGCTGTTGGAGTCTGGGGGAGGCTTGGTACAGCCCGGGGGGTCC

CTGCGTCTCTCCTGTGCAGCCTCCGGATTCACCTTTTCCAAGTATTCGATGG

GGTGGGTCCGCCAGGCTCCAGGGAAGGGTCTAGAGTGGGTCTCACAGATTT

CGGATACTGCTGATCGTACATACTACGCAGACTCCGTGAAGGGCCGGTTCA

CCATCTCCCGCGACAATTCCAAGAACACGCTGTATCTGCAAATGAACAGCC

TGCGTGCCGAGGACACCGCGGTATATTACTGTGCGATATACACTGGGCGTT

GGGTGCCTTTTGAGTACTGGGGTCAGGGAACCCTGGTCACCGTCTCGAGCG

CTAGCACCGACATCCAGATGACCCAGTCTCCATCCTCCCTGTCTGCATCTGT

AGGAGACCGTGTCACCATCACTTGCCGGGCAAGTCGTCCGATTGGGACGAC

GTTAAGTTGGTACCAGCAGAAACCAGGGAAAGCCCCTAAGCTCCTGATCCT

TTGGAATTCCCGTTTGCAAAGTGGGGTCCCATCACGTTTCAGTGGCAGTGGA

TCTGGGACAGATTTCACTCTCACCATCAGCAGTCTGCAACCTGAAGATTTTG

CTACGTACTACTGTGCGCAGGCTGGGACGCATCCTACGACGTTCGGCCAAG

GGACCAAGGTGGAAATCAAACGG

>DMS5544 (SEQ ID NO: 34)
GAGGTGCAGCTGTTGGAGTCTGGGGGAGGCTTGGTACAGCCTGGGGGGTCC

CTGCGTCTCTCCTGTGCAGCCTCCGGATTCACCTTTGATAAGTATTCAATGG

GGTGGGTCCGCCAGGCTCCAGGGAAGGGTCTAGAGTGGGTCTCACAGATTT

```
CGGATACTGCTGATCGTACATACTACGCACACTCCGTGAAGGGCCGGTTCA

CCATCTCCCGCGACAATTCCAAGAACACGCTGTATCTGCAAATGAACAGCC

TGCGTGCTGAGGACACCGCGGTATATTACTGTGCGATATATACTGGGCGTTG

GGTGCCTTTTGAGTACTGGGGTCAGGGAACCCTGGTCACCGTCTCGAGCGCT

AGCACCGACATCCAGATGACCCAGTCTCCATCCTCCCTGTCTGCATCTGTAG

GAGACCGTGTCACCATCACTTGCCGGGCAAGTCGTCCGATTGGGACGACGT

TAAGTTGGTACCAGCAGAAACCAGGGAAAGCCCCTAAGCTCCTGATCCTTT

GGAATTCCCGTTTGCAAAGTGGGGTCCCATCACGTTTCAGTGGCAGTGGATC

TGGGACAGATTTCACTCTCACCATCAGCAGTCTGCAACCTGAAGATTTTGCT

ACGTACTACTGTGCGCAGGCTGGGACGCATCCTACGACGTTCGGCCAAGGG

ACCAAGGTGGAAATCAAACGG

>DOM1h-574-72
                                                  (SEQ ID NO: 35)
GAGGTGCAGCTGTTGGAGTCTGGGGGAGGCTTGGTACAGCCTGGGGGGTCCCTGCGTC

TCTCCTGTGCAGCCTCCGGATTCACCTTTGTTAAGTATTCGATGGGGTGGGTCCGCCA

GGCTCCAGGGAAGGGTCTAGAGTGGGTCTCACAGATTTCGAATACTGCTGATCGTACA

TACTACGCACACTCCGTGAAGGGCCGGTTCACCATCTCCCGCGACAATTCCAAGAACA

CGCTGTATCTGCAAATGAACAGCCTGCGTGCTGAGGACACCGCGGTATATTACTGTGC

GATATATACTGGGCGTTGGGTGCCTTTTGAGTACTGGGGTCAGGGAACCCTGGTCACC

GTCTCGAGC

>DOM1h-574-109
                                                  (SEQ ID NO: 36)
GAGGTGCAGCTGTTGGAGTCTGGGGGAGGCTTGGTACAGCCTGGGGGGTCCCTGCGTC

TCTCCTGTGCAGCCTCCGGATTCACCTTTGTTAAGTATTCGATGGGGTGGGTCCGCCA

GGCTCCAGGGAAGGGTCTAGAGTGGGTCTCACAGATTTCGGATACTGCTGATCGTACA

TACTACGCACACTCCGTGAAGGGCCGGTTCACCATCTCCCGCGACAATTCCAAGAACA

CGCTGTATCTGCAAATGAACAGCCTGCGTGCTGAGGACACCGCGGTATATTACTGTGC

GATATATACTGGGCGTTGGGTGCCTTTTGAGTACTGGGGTCAGGGAACCCTGGTCACC

GTCTCGAGC

>DOM1h-574-133
                                                  (SEQ ID NO: 37)
GAGGTGCAGCTGTTGGAGTCTGGGGGAGGCTTGGTACAGCCTGGGGGGTCCCTGCGTC

TCTCCTGTGCAGCCTCCGGATTCACCTTTGTTAAGTATTCGATGGGGTGGGTCCGCCA

GGCTCCAGGGAAGGGTCTAGAGTGGGTCTCACAGATTTCGGATACTGCTGATCGTACA

TACTACGATCACTCCGTGAAGGGCCGGTTCACCATCTCCCGCGACAATTCCAAGAACA

CGCTGTATCTGCAAATGAACAGCCTGCGTGCCGAGGACACCGCGGTATATTACTGTGC

GATATATACGGGTCGTTGGGAGCCTTTTGTCTACTGGGGTCAGGGAACCCTGGTCACC

GTCTCGAGC

>DOM1h-574-138
                                                  (SEQ ID NO: 38)
GAGGTGCAGCTGTTGGAGTCTGGGGGAGGCTTGGTACAGCCTGGGGGGTCCCTGCGTC

TCTCCTGTGCAGCCTCCGGATTCACCTTTTTCAAGTATTCGATGGGGTGGGTCCGCCA

GGCTCCAGGGAAGGGTCTAGAGTGGGTCTCACAGATTTCGGATACTGCTGATCGTACA

TACTACGCACACTCCGTGAAGGGCCGGTTCACCATCTCCCGCGACAATTCCAAGAACA

CGCTGTATCTGCAAATGAACAGCCTGCGTGCCGAGGACACCGCGGTATATTACTGTGC
```

-continued

GATATATACGGGTCGGTGGGCGCCTTTTGAGTACTGGGGTCAGGGAACCCTGGTCACC

GTCTCGAGC

>DOM1h-574-156

(SEQ ID NO: 39)

GAGGTGCAGCTGTTGGAGTCTGGGGGAGGCTTGGTACAGCCTGGGGGGTCCCTGCGTC

TCTCCTGTGCAGCCTCCGGATTCACCTTTTTCAAGTATTCGATGGGGTGGGTCCGCCA

GGCTCCAGGGAAGGGTCTAGAGTGGGTCTCACAGATTTCGGATACTGCTGATCGTACA

TACTACGCACACTCCGTGAAGGGCCGGTTCACCATCTCCCGCGACAATTCCAAGAACA

CGCTGTATCTGCAAATGAACAGCCTGCGTGCTGAGGACACCGCGGTATATTACTGTGC

GATATATACTGGGCGTTGGGTGCCTTTTGAGTACTGGGGTCAGGGAACCCTGGTCACC

GTCTCGAGC

>DOM1h-574-180

(SEQ ID NO: 40)

GAGGTGCAGCTGTTGGAGTCTGGGGGAGGCTTGGTACAGCCTGGGGGGTCCCTGCGTC

TCTCCTGTGCAGCCTCCGGATTCACCTTTGTTAAGTATTCGATGGGGTGGGTCCGCCA

GGCTCCAGGGAAGGGTCTAGAGTGGGTCTCACAGATTTCGGATACTGCTGATCGTACA

TACTACGCACACGCGGTGAAGGGCCGGTTCACCATCTCCCGCGACAATTCCAAGAACA

CGCTGTATCTGCAAATGAACAGCCTGCGTGCTGAGGACACCGCGGTATATTACTGTGC

GATATATACTGGGCGTTGGGTGCCTTTTGAGTACTGGGGTCAGGGAACCCTGGTCACC

GTCTCGAGC

>DOM1h-574-162

(SEQ ID NO: 41)

GAGGTGCAGCTGTTGGAGTCTGGGGGAGGCTTGGTACAGCCTGGGGGGTCCCTGCGTC

TCTCCTGTGCAGCCTCCGGATTCACCTTTTTCAAGTATTCGATGGGGTGGGTCCGCCA

GGCTCCAGGGAAGGGTCTAGAGTGGGTCTCACAGATTTCGGATACTGCTGATCGTACA

TACTACTCACACTCCGTGAAGGGCCGGTTCACCATCTCCCGCGACAATTCCAAGAACA

CGCTGTATCTGCAAATGAACAGCCTGCGTGCTGAGGACACCGCGGTATATTACTGTGC

GATATATACTGGGCGTTGGGTGCCTTTTGAGTACTGGGGTCAGGGAACCCTGGTCACC

GTCTCGAGC

DOM7h-11-3

(SEQ ID NO: 42)
GACATCCAGA TGACCCAGTC TCCATCCTCC CTGTCTGCAT CTGTAGGAGA CCGTGT

CACC ATCACTTGCC GGGCAAGTCG TCCGATTGGG ACGACGTTAA GTTGGTACCA
GC

AGAAACCA GGGAAAGCCC CTAAGCTCCT GATCCTTTGG AATTCCCGTT TGCAAAGT

GG GGTCCCATCA CGTTTCAGTG GCAGTGGATC TGGGACAGAT TTCACTCTCA
CCAT

CAGCAG TCTGCAACCT GAAGATTTTG CTACGTACTA CTGTGCGCAG CTGGGACGC

ATCCTACGAC GTTCGGCCAA GGGACCAAGG TGGAAATCAA ACGG

Amino-acid sequences:
>DOM1h-574-188

(SEQ ID NO: 43)
EVQLLESGGGLVQPGGSLRLSCAASGFTFDKYSMGWVRQAPGKGLEWVSQISD

TADRTYYAHSVKGRFTISRDNSKNTLYLQMNSLRAEDTAVYYCAIYTGRWVPF

EYWGQGTLVTVSS

```
>DOM1h-574-189
                                             (SEQ ID NO: 44)
EVQLLESGGGLVQPGGSLRLSCAASGFTFFKYSMGWVRQAPGKGLEWVSQISD

TADRTYYAHSVKGRFTISRDNSKNTLYLQMNSLRAEDTAVYYCAVYTGRWEP

FEYWGQGTLVTVSS

>DOM1h-574-190
                                             (SEQ ID NO: 45)
EVQLLESGGGLVQPGGSLRLSCAASGFTFFKYSMGWIRQAPGKGLEWVSQISD

TADRTYYAHSVKGRFTISRDNSKNTLYLQMNSLRAEDTAVYYCAVYTGRWAP

FEYWGQGTLVTVSS

>DOM1h-574-191
                                             (SEQ ID NO: 46)
EVQLLESGGGLVQPGGSLRLSCAASGFTFSKYSMGWVRQAPGKGLEWVSQISD

TADRTYYAHSVKGRFTISRDNSKNTLYLQMNSLRAEDTAVYYCAIYTGRWVPF

EYWGQGTLVTVSS

>DOM1h-574-192
                                             (SEQ ID NO: 47)
EVQLLESGGGLVQPGGSLRLSCAASGFTFSKYSMGWVRQAPGKGLEWVSQISD

TADRTYYAHSVKGRFTISRDNSKNTLYLQMNSLRAEDTAVYYCAIYTGRWVPF

ENWGQGTLVTVSS

>DOM1h-574-193
                                             (SEQ ID NO: 48)
EVQLLESGGGLVQPGGSLRLSCAASGFTFDKYSMGWVRQAPGKGPEWVSQISD

TADRTYYAHSVKGRFTNSRDNSKNTLYLQMNSLRAEDTAVYYCAIYTGRWEP

FEYWGQGTLVTVSS

>DOM1h-574-194
                                             (SEQ ID NO: 49)
EVQLLESGGGLVQPGGSLRLSCAASGFTFVKYSMGWVRQAPGKGLEWVSQISD

TADRTYYAHAVKGRFTISRDNSKNTLYLQMNSLRAEDTAVYYCAIYTGRWVP

FEYWGQGTLVTVSS

>DOM1h-574-195
                                             (SEQ ID NO: 50)
EVQLLESGGGLVQPGGSLRLSCAASGFTFFKYSMGWVRQAPGKGLEWVSQISD

TADRTYYAHSVKGRFTISRDNSKNTLYLQMNSLRAEDTAVYYCAIYTGRWEPF

EYWGQGTLVTVSS

>DOM1h-574-196
                                             (SEQ ID NO: 51)
EVQLLESGGGLVQPGGSLRLSCAASGFTFSKYSMGWVRQAPGKGLEWVSQISD

TADRTYYAHSVKGRFTISRDNSKNTLYLQMNSLRAEDTAVYYCAIYTGRWEPF

EYWGQGTLVTVSS

>DOM1h-574-201
                                             (SEQ ID NO: 52)
EVQLLESGGGLVQPGGSLRLSCAASGFTFDKNSMGWVRQAPGKGLEWVSQISD

TADRTYYAHSLKGRFTISRDNSKNTLYLQMNSLRAEDTAVYYCAIYTGRWVPF

EYWGQGTLVTVSS

>DOM1h-574-202
                                             (SEQ ID NO: 53)
EVQLLESGGGLVQPGGSLRLSCAASGFTFFKYSMGWVRQAPGKGLEWVSQISD

TADRTYYAHSVKGRFTISRDNSKNTLYLQMNSLRAEDTAVYYCAVYTGRWAP
```

FEYWGQGTLVTVSS

>DOM1h-574-203
(SEQ ID NO: 54)
EVQLLESGGGLVQPGGSLRLSCAASGFTFFKYSMGWVRQAPGKGLEWVSQISD

TADRTYYAHSVKGRFTISRDDSKNTLYLQMNSLRAEDTAVYYCAIYTGRWAPF

EYWGQGTLVTVSS

>DOM1h-574-204
(SEQ ID NO: 55)
EVQLLESGGGLVQPGGSLRLSCAASGFTFFKYSMGWVRQAPGKGLEWVSQISD

TADRTYYAHSVKGRFTISRDNSKNTLYLQMNSLRVEDTAVYYCAIYTGQWAP

YEYWGQGTLVTVRA

>DOM1h-574-205
(SEQ ID NO: 56)
EVQLLESGGGLVQPGGSLRLSCAASGFTFDKYSMGWVRQAPGKDLEWVSQISD

TADRTYYAHSVKGRFTISRDNSKNTLYLQMNSLRAEDTAVYYCAIYTGRWVPF

ENWGHGTLVTVSS

>DOM1h-574-206
(SEQ ID NO: 57)
EVQLLDSGGGLVQPGGSLRLSCAASGFTFFKYSMGWVRQAPGKGLEWVSQISD

TADRTYYSPSVKGRFTISRDNSGNTLNLQMTPLRAEDTAVYYCAIYTGRWEPFE

YWGQGTLVTVSS

>DOM1h-574-207
(SEQ ID NO: 58)
EVQLLESGGGMVQPGGSLRLSCASSGFTFSKYSMGWVRQAPGKGLEWVSQISD

TADLTYYAHSVKGRFTISRDNSKNTLYLQMNSLRAEDTAEYYCAIYTGRWAPF

EYWGQGTLVTVSS

>DOM1h-574-208
(SEQ ID NO: 59)
EVQLLESGGGLVQPGGSLRLSCAASGFTFDKYSMGWVRQAPGKGLEWVSQISD

TADRTYYAHAVKGRFTISRDNSKNTLYLQMNSLRAEDTAVYYCAIYTGRWVP

FEYWGQGTLVTVSS

>DOM1h-574-209
(SEQ ID NO: 60)
EVQLLESGGGLVQPGGSLRLSCAASGFTFFKYSMGWVRQAPGKGLEWVSQISD

TADRTYYAHSVKGRFTISRDNSKNTLYLQMNSLRVEDTAVYYCAIYTGQWAP

YEYWGQGTLVTVSS

>DOM1h-574-211
(SEQ ID NO: 61)
EVQLLESGGGLVQPGGSLRLSCAASGFTFAKYSMGWVRQAPGKGLEWVSQISD

TADRTYYAHAVKGRFTISRDNSKNTLYLQMNSLRAEDTAVYYCAIYTGRWVP

FEYWGQGTLVTVSS

>DOM1h-574-212
(SEQ ID NO: 62)
EVQLLESGGGLVQPGGSLRLSCAASGFTFSKYSMGWVRQAPGKGLEWVSQISD

TADRTYYAHSVKGRFTISRDNSKNTLYLQMNSLRAEDTAVYYCAIYTGRWVPF

EYWGQGTLVTVSS

>DOM1h-574-213
(SEQ ID NO: 63)
EVQLLESGGGLVQPGGSLRLSCAASGFTFDKYSMGWVRQAPGKGLEWVSQISD

TADRTYYAHSVKGRFTITRDNSKNTLYLQMNSLRAEDTAVYYCAIYTGRWEPF

```
EYWGQGTLVTVSS

>DOM1h-574-214
                                                        (SEQ ID NO: 64)
EVQLLESGGGLVQPGGSLRLSCAASGFTFSKYSMGWVRQAPGKGLEWVSQISD

TADRTYYADSVKGRFTISRDNSKNTLYLQMNSLRAEDTAVYYCAIYTGRWVPF

EYWGQGTLVTVSS

>DMS5535
                                                        (SEQ ID NO: 65)
EVQLLESGGGLVQPGGSLRLSCAASGFTFSKYSMGWVRQAPGKGLEWVSQISD

TADRTYYAHSVKGRFTISRDNSKNTLYLQMNSLRAEDTAVYYCAIYTGRWEPF

EYWGQGTLVTVSSASTDIQMTQSPSSLSASVGDRVTITCRASRPIGTTLSWYQQ

KPGKAPKLLILWNSRLQSGVPSRFSGSGSGTDFTLTISSLQPEDFATYYCAQAGT

HPTTFGQGTKVEIKR

>DMS5541
                                                        (SEQ ID NO: 66)
EVQLLESGGGLVQPGGSLRLSCAASGFTFDKYSMGWVRQAPGKGLEWVSQISD

TADRTYYAHAVKGRFTISRDNSKNTLYLQMNSLRAEDTAVYYCAIYTGRWVP

FEYWGQGTLVTVSSASTDIQMTQSPSSLSASVGDRVTITCRASRPIGTTLSWYQ

QKPGKAPKLLILWNSRLQSGVPSRFSGSGSGTDFTLTISSLQPEDFATYYCAQAG

THPTTFGQGTKVEIKR

>DMS5542
                                                        (SEQ ID NO: 67)
EVQLLESGGGLVQPGGSLRLSCAASGFTFSKYSMGWVRQAPGKGLEWVSQISD

TADRTYYADSVKGRFTISRDNSKNTLYLQMNSLRAEDTAVYYCAIYTGRWVPF

EYWGQGTLVTVSSASTDIQMTQSPSSLSASVGDRVTITCRASRPIGTTLSWYQQ

KPGKAPKLLILWNSRLQSGVPSRFSGSGSGTDFTLTISSLQPEDFATYYCAQAGT

HPTTFGQGTKVEIKR

>DMS5544
                                                        (SEQ ID NO: 68)
EVQLLESGGGLVQPGGSLRLSCAASGFTFDKYSMGWVRQAPGKGLEWVSQISD

TADRTYYAHSVKGRFTISRDNSKNTLYLQMNSLRAEDTAVYYCAIYTGRWVPF

EYWGQGTLVTVSSASTDIQMTQSPSSLSASVGDRVTITCRASRPIGTTLSWYQQ

KPGKAPKLLILWNSRLQSGVPSRFSGSGSGTDFTLTISSLQPEDFATYYCAQAGT

HPTTFGQGTKVEIKR

>DOM1h-574-72
                                                        (SEQ ID NO: 69)
EVQLLESGGGLVQPGGSLRLSCAASGFTFVKYSMGWVRQAPGKGLEWVSQISNTADRT

YYAHSVKGRFTISRDNSKNTLYLQMNSLRAEDTAVYYCAIYTGRWVPFEYWGQGTLVT

VSS

>DOM1h-574-109
                                                        (SEQ ID NO: 70)
EVQLLESGGGLVQPGGSLRLSCAASGFTFVKYSMGWVRQAPGKGLEWVSQISDTADRT

YYAHSVKGRFTISRDNSKNTLYLQMNSLRAEDTAVYYCAIYTGRWVPFEYWGQGTLVT

VSS

>DOM1h-574-133
                                                        (SEQ ID NO: 71)
EVQLLESGGGLVQPGGSLRLSCAASGFTFVKYSMGWVRQAPGKGLEWVSQISDTADRT

YYDHSVKGRFTISRDNSKNTLYLQMNSLRAEDTAVYYCAIYTGRWEPFVYWGQGTLVT

VSS
```

-continued

>DOM1h-574-138
(SEQ ID NO: 72)
EVQLLESGGGLVQPGGSLRLSCAASGFIFFKYSMGWVRQAPGKGLEWVSQISDTADRT

YYAHSVKGRFTISRDNSKNTLYLQMNSLRAEDTAVYYCAIYTGRWAPFEYWGQGTLVT

VSS

>DOM1h-574-156
(SEQ ID NO: 73)
EVQLLESGGGLVQPGGSLRLSCAASGFIFFKYSMGWVRQAPGKGLEWVSQISDTADRT

YYAHSVKGRFTISRDNSKNTLYLQMNSLRAEDTAVYYCAIYTGRWVPFEYWGQGTLVT

VSS

>DOM1h-574-180
(SEQ ID NO: 74)
EVQLLESGGGLVQPGGSLRLSCAASGFTFVKYSMGWVRQAPGKGLEWVSQISDTADRT

YYAHAVKGRFTISRDNSKNTLYLQMNSLRAEDTAVYYCAIYTGRWVPFEYWGQGTLVT

VSS

>DOM1h-574-162
(SEQ ID NO: 75)
EVQLLESGGGLVQPGGSLRLSCAASGFIFFKYSMGWVRQAPGKGLEWVSQISDTADRT

YYSHSVKGRFTISRDNSKNTLYLQMNSLRAEDTAVYYCAIYTGRWVPFEYWGQGTLVT

VSS

DOM7h-11-3
(SEQ ID NO: 76)
DIQMTQSPSSLSASVGDRVTITCRASRPIGTTLSWYQQKPGKAPKLLILWNSRLQSGV

PSRFSGSGSGTDFTLTISSLQPEDFATYYCAQAGTHPTTFGQGTKVEIKR

---

The invention claimed is:

1. An anti-TNFα receptor type 1 (TNFR1; p55) immunoglobulin single variable domain comprising an amino acid sequence that is 100% identical to the amino acid sequence of DOM1h-574-208, wherein the single variable domain has an $OD_{320}$<1.0, <0.9, <0.8, <0.7, <0.6, <0.5, or <0.4 after incubation in PBS at 40° C. for 40 hours.

2. A multispecific ligand comprising an immunoglobulin single variable domain of claim 1 and optionally at least one immunoglobulin single variable domain that specifically binds serum albumin (SA).

3. A multispecific ligand according to claim 2, wherein the ligand comprises (i) an anti-TNFα receptor type 1 (TNFR1; p55) immunoglobulin single variable domain according to claim 1, (ii) at least one anti-serum albumin (SA) immunoglobulin single variable domain that specifically binds SA, wherein the anti-SA single variable domain comprises an amino acid sequence that is at least 80, 85, 90, 95, 96, 97, 98 or 99% identical (or 100% identical) to the sequence of DOM7h-11-3, and (iii) optionally wherein a linker is provided between the anti-TNFR1 single variable domain and the anti-SA single variable domain.

4. The ligand of claim 3, wherein the linker comprises the amino acid sequence AST, (optionally ASTSGPS), or wherein the linker is $AS(G_4S)_n$, where n is 1, 2, 3, 4, 5, 6, 7 or 8, for example $AS(G_4S)_3$.

5. A TNFR1 antagonist comprising a single variable domain or multispecific ligand of claim 1.

6. A TNFα receptor type 1 (TNFR1; p55) antagonist according to claim 5, for oral delivery, delivery to the GI tract of a patient, pulmonary delivery, delivery to the lung of a patient or systemic delivery.

7. A TNFα receptor type 1 (TNFR1; p55) antagonist according to claim 5, for treating and/or prophylaxis of an inflammatory condition.

8. A multispecific ligand comprising DOM1h-574-208, an Ala-Ser-Thr linker, and DOM7h-11-3.

* * * * *